(12) United States Patent
Gavai

(10) Patent No.: US 9,133,126 B2
(45) Date of Patent: Sep. 15, 2015

(54) FLUOROALKYL DIBENZOAZEPINONE COMPOUNDS

(71) Applicant: BRISTOL-MYERS SQUIBB COMPANY, Princeton, NJ (US)

(72) Inventor: Ashvinikumar V. Gavai, Princeton Junction, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 14/429,951

(22) PCT Filed: Sep. 20, 2013

(86) PCT No.: PCT/US2013/060783
§ 371 (c)(1),
(2) Date: Mar. 20, 2015

(87) PCT Pub. No.: WO2014/047370
PCT Pub. Date: Mar. 27, 2014

(65) Prior Publication Data
US 2015/0218104 A1 Aug. 6, 2015

Related U.S. Application Data

(60) Provisional application No. 61/703,918, filed on Sep. 21, 2012.

(51) Int. Cl.
C07D 223/18 (2006.01)
A61K 31/55 (2006.01)
A61K 45/06 (2006.01)

(52) U.S. Cl.
CPC .............. *C07D 223/18* (2013.01); *A61K 31/55* (2013.01); *A61K 45/06* (2013.01)

(58) Field of Classification Search
CPC ................................................... C07D 223/18
See application file for complete search history.

(56) References Cited

U.S. PATENT DOCUMENTS

| | | | |
|---|---|---|---|
| 4,981,847 A | 1/1991 | Sato et al. | |
| 5,322,842 A | 6/1994 | Sato et al. | |
| 5,324,726 A | 6/1994 | Bock et al. | |
| 5,852,010 A | 12/1998 | Graham et al. | |
| 5,998,407 A | 12/1999 | Graham et al. | |
| 6,331,408 B1 | 12/2001 | Zaczek et al. | |
| 6,495,540 B2 | 12/2002 | Thompson | |
| 6,503,901 B1 | 1/2003 | Thompson et al. | |
| 6,503,902 B2 | 1/2003 | Olson et al. | |
| 6,509,333 B2 | 1/2003 | Olson | |
| 6,525,044 B2 | 2/2003 | Olson et al. | |
| 6,544,978 B2 | 4/2003 | Wu et al. | |
| 6,632,812 B2 | 10/2003 | Han et al. | |
| 6,653,303 B1 | 11/2003 | Wu et al. | |
| 6,713,476 B2 | 3/2004 | Yang et al. | |
| 6,737,038 B1 | 5/2004 | Zaczek et al. | |
| 6,756,511 B2 | 6/2004 | Castro Pineiro et al. | |
| 6,759,404 B2 | 7/2004 | Olson et al. | |
| 6,794,381 B1 | 9/2004 | Olson et al. | |
| 6,878,363 B2 | 4/2005 | Zaczek et al. | |
| 6,900,199 B2 | 5/2005 | Han et al. | |
| 6,958,329 B2 | 10/2005 | Olson | |
| 6,960,576 B2 | 11/2005 | Olson et al. | |
| 6,962,913 B2 | 11/2005 | Olson et al. | |
| 6,984,626 B2 | 1/2006 | Nadin et al. | |
| 7,001,901 B2 | 2/2006 | Yang | |
| 7,053,081 B2 | 5/2006 | Olson et al. | |
| 7,053,084 B1 | 5/2006 | Olson | |
| 7,101,870 B2 | 9/2006 | Olson et al. | |
| 7,105,509 B2 | 9/2006 | Castro Pineiro et al. | |
| 7,112,583 B2 | 9/2006 | Olson et al. | |
| 7,125,866 B1 | 10/2006 | Glick et al. | |
| 7,153,491 B2 | 12/2006 | Zaczek et al. | |
| 7,160,875 B2 | 1/2007 | Flohr et al. | |
| 7,276,495 B2 | 10/2007 | Han et al. | |
| 7,276,496 B2 | 10/2007 | Olson et al. | |
| 7,304,049 B2 | 12/2007 | Olson | |
| 7,304,055 B2 | 12/2007 | Olson et al. | |
| 7,304,056 B2 | 12/2007 | Olson et al. | |
| 7,342,008 B2 | 3/2008 | Olson et al. | |

(Continued)

FOREIGN PATENT DOCUMENTS

| | | |
|---|---|---|
| EP | 0669334 | 8/1995 |
| WO | WO 97/36879 | 10/1997 |

(Continued)

OTHER PUBLICATIONS

U.S. Appl. No. 14/627,573, Feb. 20, 2015, Gavai et al.

Groth, C., et al., "Therapeutic approaches to modulating Notch signaling: Current challenges and future prospects," Seminars in Cell & Developmental Biology, (2012), doi:10.1016/j.semcdb2012.01.016; available online Mar. 7, 2012.

Seiffert, D., et al., "Presenilin-1 and -2 Are Molecular Targets for gamma-Secretase Inhibitors," the Journal of Biological Chemistry, vol. 275, No. 44, pp. 34086-34091 (2000).

Beher, D., et al., "Pharmacological Knock-down of the Presenilin 1 Heterodimer by a Novel gamma-Secretase Inhibitor," The Journal of Biological Chemistry, vol. 276, No. 48, pp. 45394-45402 (2001).

(Continued)

*Primary Examiner* — Bruck Kifle
(74) *Attorney, Agent, or Firm* — Gary D. Greenblatt

(57) ABSTRACT

Disclosed are compounds of Formula (I): wherein $R_1$ is $CH_2CH2CF_3$ or $CH_2CH2CH_3$; R2 is $CH_2CH_2CF_3$, $CH_2CH_2CH_3$, $CH_2(cyclopropyl)$, phenyl, or; $R_3$ is H; $R_a$, $R_b$, y, and z are defined herein. Also disclosed are methods of using such compounds to inhibit the Notch receptor, and pharmaceutical compositions comprising such compounds. These compounds are useful in treating, preventing, or slowing the progression of diseases or disorders in a variety of therapeutic areas, such as cancer.

8 Claims, No Drawings

(56) References Cited

U.S. PATENT DOCUMENTS

| | | |
|---|---|---|
| 7,354,914 B2 | 4/2008 | Olson |
| 7,375,099 B2 | 5/2008 | Galley et al. |
| 7,390,802 B2 | 6/2008 | Han et al. |
| 7,390,896 B2 | 6/2008 | Olson et al. |
| 7,423,033 B2 | 9/2008 | Olson et al. |
| 7,456,172 B2 | 11/2008 | Olson |
| 7,456,278 B2 | 11/2008 | Olson |
| 7,498,324 B2 | 3/2009 | Han et al. |
| 7,528,249 B2 | 5/2009 | Olson et al. |
| 7,544,679 B2 | 6/2009 | Flohr et al. |
| 7,582,624 B2 | 9/2009 | Carter et al. |
| 7,655,647 B2 | 2/2010 | Han et al. |
| 7,718,795 B2 | 5/2010 | Olson |
| 8,629,136 B2 | 1/2014 | Gavai et al. |
| 8,822,454 B2 | 9/2014 | Gavai et al. |
| 8,999,918 B2 | 4/2015 | Gavai et al. |
| 2007/0185094 A1 | 8/2007 | Lattmann et al. |
| 2009/0181944 A1 | 7/2009 | Boylan et al. |
| 2014/0357805 A1 | 12/2014 | Gavai et al. |

FOREIGN PATENT DOCUMENTS

| | | |
|---|---|---|
| WO | WO 01/74796 | 10/2001 |
| WO | WO 01/90084 | 11/2001 |
| WO | WO 2007/067048 | 6/2007 |
| WO | WO 2009/023453 | 2/2009 |
| WO | WO 2014/047369 | 3/2014 |
| WO | WO 2014/047374 | 3/2014 |
| WO | WO 2014/047390 | 3/2014 |
| WO | WO 2014/047391 | 3/2014 |
| WO | WO 2014/047392 | 3/2014 |
| WO | WO 2014/047393 | 3/2014 |
| WO | WO 2014/047397 | 3/2014 |

OTHER PUBLICATIONS

Iben, L.G., et al., "Signal Peptide Peptidase and gamma-Secretase Share Equivalent Inhibitor Binding Pharmacology," The Journal of Biological Chemistry, vol. 282, No. 51, pp. 36829-36836 (2007).

Meredith, Jere, "Characterization of APP Activity and Notch Toxicity with gamma-Secretase Inhibitors," 8th International AD/PD Meeting, Salzberg, Austria, Mar. 17, 2007.

Prasad, C.V.C., et al., "Discovery of (S)-2-((S)-2(3,5-difluorophenyl)-2-hydroxyacetamido)-N-((S,Z)-3-methyl-4-oxo-4,5-dihydro-3H-benzo[d][1,2]diazepin-5-yl)propanamide (BMS-433796): A gamma-secretase inhibitor with A beta lowering activity in a transgenic mouse model of Alzheimer's disease," Bioorganic & Medicinal Chemistry Letters 17 pp. 4006-4011 (2007).

Jun, H.T., et al., "Top Notch Targets: Notch Signaling in Cancer," Drug Development Research, 69, pp. 319-328 (2008).

Meredith, J.E., et al., Gamma-Secretase activity is not involved in presenilin-mediated regulation of beta-catenin, Biochemical and Biophysical Research Communications 299 pp. 744-750 (2002).

Shih, L., et al., Notch Signaling, gamma-Secretase Inhibitors, and Cancer Therapy, Cancer Res. 67, pp. 1879-1882 (2007).

Olson, Richard, "Optimizing gamma-secretase Inhibitors for safety and efficacy," 8th International AD/PD Meeting, Mar. 14-18, 2007, Salzberg, Austria.

PCT/US2013/060783 International Search Report mailed Oct. 30, 2013.

PCT/US2013/060783 Preliminary Report on Patentability issued Mar. 24, 2015.

FLUOROALKYL DIBENZOAZEPINONE COMPOUNDS

CROSS REFERENCE TO RELATED APPLICATIONS

This application is a national phase application under 35 U.S.C. §371 of International Patent Application No. PCT/US2013/060783, filed Sep. 20, 2013, which claims priority to U.S. Provisional Application 61/703,918, filed Sep. 21, 2012, which are expressly incorporated fully herein by reference.

The present invention generally relates to dibenzoazepinone compounds useful as Notch inhibitors. The invention further pertains to pharmaceutical compositions comprising at least one compound according to the invention that is useful for the treatment of conditions related to the Notch pathway, such as cancer and other proliferative diseases.

Notch signaling has been implicated in a variety of cellular processes, such as cell fate specification, differentiation, proliferation, apoptosis, and angiogenesis. (Bray, *Nature Reviews Molecular Cell Biology*, 7:678-689 (2006); Fortini, *Developmental Cell*, 16:633-647 (2009)). The Notch proteins are single-pass heterodimeric transmembrane molecules. The Notch family includes 4 receptors, NOTCH 1-4, which become activated upon binding to ligands from the DSL family (Delta-like 1, 3, 4 and Jagged 1 and 2).

The activation and maturation of NOTCH requires a series of processing steps, including a proteolytic cleavage step mediated by gamma secretase, a multiprotein complex containing Presenilin 1 or Presenilin 2, nicastrin, APH1, and PEN2. Once NOTCH is cleaved, NOTCH intracellular domain (NICD) is released from the membrane. The released NICD translocates to the nucleus, where it functions as a transcriptional activator in concert with CSL family members (RBPSUH, "suppressor of hairless", and LAG1). NOTCH target genes include HES family members, such as HES-1. HES-1 functions as transcriptional repressors of genes such as HERP1 (also known as HEY2), HERP2 (also known as HEY1), and HATH1 (also known as ATOH1).

The aberrant activation of the Notch pathway contributes to tumorigenesis. Activation of Notch signaling has been implicated in the pathogenesis of various solid tumors including ovarian, pancreatic, as well as breast cancer and hematologic tumors such as leukemias, lymphomas, and multiple myeloma. The role of Notch inhibition and its utility in the treatment of various solid and hematological tumors are described in Miele, L. et al., *Current Cancer Drug Targets*, 6:313-323 (2006); Bolos, V. et al., *Endocrine Reviews*, 28:339-363 (2007); Shih, I-M. et al., *Cancer Research*, 67:1879-1882 (2007); Yamaguchi, N. et al., *Cancer Research*, 68:1881-1888 (2008); Miele, L., *Expert Review Anticancer Therapy*, 8:1197-1201 (2008); Purow, B., *Current Pharmaceutical Biotechnology*, 10:154-160 (2009); Nefedova, Y. et al., *Drug Resistance Updates*, 11:210-218 (2008); Dufraine, J. et al., *Oncogene*, 27:5132-5137 (2008); and Jun, H. T. et al., *Drug Development Research*, 69:319-328 (2008).

There remains a need for compounds that are useful as Notch inhibitors and that have sufficient metabolic stability to provide efficacious levels of drug exposure. Further, there remains a need for compounds useful as Notch inhibitors that can be orally or intravenously administered to a patient.

U.S. Pat. No. 7,053,084 B1 discloses succinoylamino benzodiazepine compounds useful for treating neurological disorders such as Alzheimer's Disease. The reference discloses that these succinoylamino benzodiazepine compounds inhibit gamma secretase activity and the processing of amyloid precursor protein linked to the formation of neurological deposits of amyloid protein.

Applicants have found potent compounds that have activity as Notch inhibitors and have sufficient metabolic stability to provide efficacious levels of drug exposure upon intravenous or oral administration. These compounds are provided to be useful as pharmaceuticals with desirable stability, bioavailability, therapeutic index, and toxicity values that are important to their drugability.

SUMMARY OF THE INVENTION

The present invention fills the foregoing need by providing fluoroalkyl dibenzoazepinone compounds that are useful as selective inhibitors of Notch signaling pathway.

The present invention also provides pharmaceutical compositions comprising a pharmaceutically acceptable carrier; and at least one compound of Formula (I).

The present invention also provides a method of treating a disease or disorder associated with the activity of the Notch receptor, the method comprising administering to a mammalian patient at least one compound of Formula (I).

The present invention also provides processes and intermediates for making the compounds of Formula (I).

The present invention also provides the compounds of Formula (I) for use in therapy.

The present invention also provides the use of the compounds of Formula (I) for the manufacture of a medicament for the treatment of cancer.

The compounds of Formula (I) and compositions comprising the compounds are Notch inhibitors that may be used in treating, preventing or curing various Notch receptor-related conditions. Pharmaceutical compositions comprising these compounds are useful in treating, preventing, or slowing the progression of diseases or disorders in a variety of therapeutic areas, such as cancer.

These and other features of the invention will be set forth in expanded form as the disclosure continues.

DETAILED DESCRIPTION

The first aspect of the present invention provides at least one compound of Formula (I):

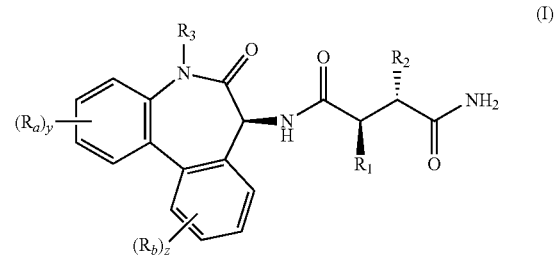

or at least one prodrug thereof, wherein:

$R_1$ is —$CH_2CH_2CF_3$ or —$CH_2CH_2CH_3$;

$R_2$ is —$CH_2CH_2CF_3$, —$CH_2CH_2CH_3$, —$CH_2$(cyclopropyl), phenyl, or

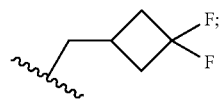

$R_3$ is H;

each $R_a$ is independently F, Cl, —CN, —OH, —CH$_3$, —CH$_2$OH, cyclopropyl, —CF$_3$, —CH$_2$CF$_3$, —OCH$_3$, —OCF$_3$, and/or —O(cyclopropyl);

each $R_b$ is independently F, Cl, —CH$_3$, —CF$_3$, —CN, and/or —OCH$_3$;

y is zero, 1, or 2; and z is zero, 1, or 2;

with the proviso that $R_1$ and $R_2$ are not each —CH$_2$CH$_2$CH$_3$ simultaneously.

One embodiment provides at least one compound of Formula (I) wherein $R_1$ is —CH$_2$CH$_2$CF$_3$; and $R_2$, $R_3$, $R_a$, $R_b$, y, and z are defined in the first aspect. Included in this embodiment are compounds in which y is zero or 1 Also included in this embodiment are compounds in which $R_a$ is F and y is zero or 1.

One embodiment provides at least one compound of Formula (I) wherein $R_1$ is —CH$_2$CH$_2$CH$_3$; $R_2$ is —CH$_2$CH$_2$CF$_3$, —CH$_2$(cyclopropyl), phenyl, or

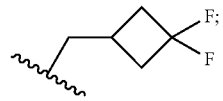 [SMILES: *CC1CC(F)(F)C1]

and $R_3$, $R_a$, $R_b$, y, and z are defined in the first aspect. Included in this embodiment are compounds in which y is zero or 1. Also included in this embodiment are compounds in which $R_a$ is F and y is zero or 1.

One embodiment provides at least one compound of Formula (I) wherein $R_2$ is —CH$_2$CH$_2$CF$_3$; and $R_1$, $R_3$, $R_a$, $R_b$, y, and z are defined in the first aspect. Included in this embodiment are compounds in which y is zero or 1. Also included in this embodiment are compounds in which $R_a$ is F and y is zero or 1.

One embodiment provides at least one compound of Formula (I) wherein $R_2$ is —CH$_2$CH$_2$CH$_3$; $R_1$ is —CH$_2$CH$_2$CF$_3$; and $R_3$, $R_a$, $R_b$, y, and z are defined in the first aspect. Included in this embodiment are compounds in which y is zero or 1. Also included in this embodiment are compounds in which $R_a$ is F and y is zero or 1.

One embodiment provides at least one compound of Formula (I) wherein $R_2$ is —CH$_2$(cyclopropyl); and $R_1$, $R_3$, $R_a$, $R_b$, y, and z are defined in the first aspect. Included in this embodiment are compounds in which y is zero or 1. Also included in this embodiment are compounds in which $R_a$ is F and y is zero or 1.

One embodiment provides at least one compound of Formula (I) wherein $R_2$ is phenyl; and $R_1$, $R_3$, $R_a$, $R_b$, y, and z are defined in the first aspect. Included in this embodiment are compounds in which y is zero or 1. Also included in this embodiment are compounds in which $R_a$ is F and y is zero or 1.

One embodiment provides at least one compound of Formula (I) wherein $R_2$ is

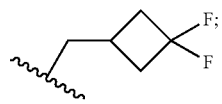 [SMILES: *CC1CC(F)(F)C1]

and $R_1$, $R_3$, $R_a$, $R_b$, y, and z are defined in the first aspect. Included in this embodiment are compounds in which y is zero or 1. Also included in this embodiment are compounds in which $R_a$ is F and y is zero or 1.

One embodiment provides at least one compound of Formula (I) wherein y is zero or 1; and $R_1$, $R_2$, $R_3$, $R_a$, $R_b$, and z are defined in the first aspect. Included in this embodiment are compounds in which $R_a$ is F, Cl, —CH$_3$, or —CH$_2$OH. Also included are compounds in which $R_a$ is F, Cl, or —CH$_3$.

One embodiment provides at least one compound of Formula (I) having the structure:

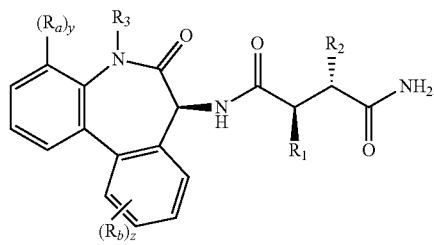

wherein y is zero or 1; and $R_1$, $R_2$, $R_3$, $R_a$, $R_b$, and z are defined in the first aspect. Included in this embodiment are compounds in which $R_a$ is F, Cl, or —CH$_3$. Also included are compounds in which $R_a$ is F, Cl, or —CH$_3$; and $R_b$ is F.

One embodiment provides at least one compound of Formula (I) having the structure:

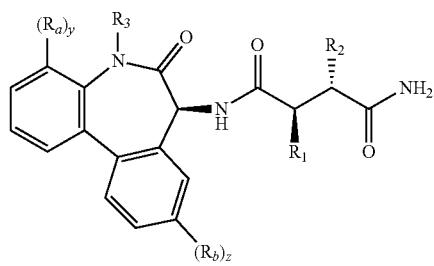

wherein y is zero or 1; z is zero or 1; and $R_1$, $R_2$, $R_3$, $R_a$, and $R_b$ are defined in the first aspect. Included in this embodiment are compounds in which $R_a$ is F, Cl, or —CH$_3$. Also included are compounds in which $R_a$ is F, Cl, or —CH$_3$; and $R_b$ is F.

One embodiment provides at least one compound of Formula (I) wherein y is zero; z is zero; and $R_1$, $R_2$, $R_3$, $R_a$, and $R_b$ are defined in the first aspect.

One embodiment provides at least one compound of Formula (I) wherein $R_3$ is H; and $R_1$, $R_2$, $R_a$, $R_b$, y, and z are defined in the first aspect. Included in this embodiment are compounds in which $R_3$ is deuterium (D) or tritium (T).

One embodiment provides a compound of Formula (I) selected from: (2R,3S)-N-((7S)-6-oxo-6,7-dihydro-5h-dibenzo[b,d]azepin-7-yl)-2,3-bis(3,3,3-trifluoropropyl)succinamide (1); (2R,3S)-N-((7S)-6-oxo-6,7-dihydro-5H-dibenzo[b,d]azepin-7-yl)-3-propyl-2-(3,3,3-trifluoropropyl)succinamide (2); (2R,3S)-3-(cyclopropylmethyl)-N-((7S)-6-oxo-6,7-dihydro-5H-dibenzo[b,d]azepin-7-yl)-2-(3,3,3- trifluoropropyl)succinamide (3); (2R,3S)-N-((7S)-6-oxo-6,7-dihydro-5H-dibenzo[b,d]azepin-7-yl)-2-propyl-3-(3,3,3-trifluoropropyl)succinamide (4); (2R,3S)-3-(cyclopropylmethyl)-N-((7S)-4-fluoro-6-oxo-6,7-dihydro-5H-dibenzo[b,d]azepin-7-yl)-2-(3,3,3-trifluoropropyl) succinamide (5); (2R,3R)-N-((7S)-6-oxo-6,7-dihydro-5H-dibenzo[b,d]azepin-7-yl)-3-phenyl-2-(3,3,3-trifluoropropyl) succinamide (6); (2R,3S)-3-((3,3-difluorocyclobutyl) methyl)-N-((7S)-6-oxo-6,7-dihydro-5H-dibenzo[b,d] azepin-7-yl)-2-(3,3,3-trifluoropropyl)succinamide (7); (2R,3S)-N-(4-chloro-6-oxo-6,7-dihydro-5H-dibenzo[b,d]azepin-7-yl)-2,3-bis(3,3,3-trifluoropropyl)succinamide (8); (2R,3S)-N-(4-fluoro-6-oxo-6,7-dihydro-5H-dibenzo[b,d]azepin-7-yl)-3-propyl-2-(3,3,3-trifluoropropyl)succinamide (9); (2R,3S)-N-((7S)-9-fluoro-4-methyl-6-oxo-6,7-dihydro-5H-dibenzo[b,d]azepin-7-yl)-2,3-bis(3,3,3-trifluoropropyl) succinamide (10); and (2R,3S)-3-(cyclopropylmethyl)-N-((7S)-9-fluoro-4-methyl-6-oxo-6,7-dihydro-5H-dibenzo[b,d]azepin-7-yl)-2-(3,3,3-trifluoropropyl)succinamide (11).

One embodiment provides at least one compound of Formula (I) having a metabolic half life value of at least 45 minutes as measured in the human metabolic stability half-life assay described herein.

One embodiment provides at least one compound of Formula (I) having a metabolic half life value of at least 60 minutes as measured in the human metabolic stability half-life assay described herein.

The present invention may be embodied in other specific forms without departing from the spirit or essential attributes thereof. This invention encompasses all combinations of the aspects and/or embodiments of the invention noted herein. It is understood that any and all embodiments of the present invention may be taken in conjunction with any other embodiment or embodiments to describe addition more embodiments. It is also to be understood that each individual element of the embodiments is meant to be combined with any and all other elements from any embodiment to describe an additional embodiment.

DEFINITIONS

The features and advantages of the invention may be more readily understood by those of ordinary skill in the art upon reading the following detailed description. It is to be appreciated that certain features of the invention that are, for clarity reasons, described above and below in the context of separate embodiments, may also be combined to form a single embodiment. Conversely, various features of the invention that are, for brevity reasons, described in the context of a single embodiment, may also be combined so as to form sub-combinations thereof. Embodiments identified herein as exemplary or preferred are intended to be illustrative and not limiting.

Unless specifically stated otherwise herein, references made in the singular may also include the plural. For example, "a" and "an" may refer to either one, or one or more.

Unless otherwise indicated, any heteroatom with unsatisfied valences is assumed to have hydrogen atoms sufficient to satisfy the valences.

The definitions set forth herein take precedence over definitions set forth in any patent, patent application, and/or patent application publication incorporated herein by reference.

Listed below are definitions of various terms used to describe the present invention. These definitions apply to the terms as they are used throughout the specification (unless they are otherwise limited in specific instances) either individually or as part of a larger group.

Throughout the specification, groups and substituents thereof may be chosen by one skilled in the field to provide stable moieties and compounds.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The compounds of Formula (I) can be provided as amorphous solids or crystalline solids. Lyophilization can be employed to provide the compounds of Formula (I) as a solid.

It should further be understood that solvates (e.g., hydrates) of the Compounds of Formula (I) are also within the scope of the present invention. The term "solvate" means a physical association of a compound of Formula (I) with one or more solvent molecules, whether organic or inorganic. This physical association includes hydrogen bonding. In certain instances the solvate will be capable of isolation, for example when one or more solvent molecules are incorporated in the crystal lattice of the crystalline solid. "Solvate" encompasses both solution-phase and isolable solvates. Exemplary solvates include hydrates, ethanolates, methanolates, isopropanolates, acetonitrile solvates, and ethyl acetate solvates. Methods of solvation are known in the art.

Any compound that can be converted in vivo to provide the bioactive agent (i.e., the compound of Formula (I)) is a prodrug within the scope and spirit of the invention.

Various forms of prodrugs are well known in the art and are described in:
a) Wermuth, C. G. et al., *The Practice of Medicinal Chemistry*, Chapter 31, Academic Press (1996);
b) Bundgaard, H. ed., Design of Prodrugs, Elsevier (1985);
c) Bundgaard, H., Chapter 5, "Design and Application of Prodrugs", Krogsgaard-Larsen, P. et al., eds., *A Textbook of Drug Design and Development*, pp. 113-191, Harwood Academic Publishers (1991); and
d) Testa, B. et al., *Hydrolysis in Drug and Prodrug Metabolism*, Wiley-VCH (2003).

In addition, compounds of Formula (I), subsequent to their preparation, can be isolated and purified to obtain a composition containing an amount by weight equal to or greater than 99% of a compound of Formula (I) ("substantially pure"), which is then used or formulated as described herein. Such "substantially pure" compounds of Formula (I) are also contemplated herein as part of the present invention.

"Stable compound" and "stable structure" are meant to indicate a compound that is sufficiently robust to survive isolation to a useful degree of purity from a reaction mixture, and formulation into an efficacious therapeutic agent. The present invention is intended to embody stable compounds.

"Therapeutically effective amount" is intended to include an amount of a compound of the present invention alone or an amount of the combination of compounds claimed or an amount of a compound of the present invention in combination with other active ingredients effective to act as an inhibitor to a NOTCH receptor, or effective to treat or prevent proliferative diseases such as cancer.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting its development; and/or (c) relieving the disease-state, i.e., causing regression of the disease state.

The compounds of the present invention are intended to include all isotopes of atoms occurring in the present compounds. Isotopes include those atoms having the same atomic number but different mass numbers. By way of general example and without limitation, isotopes of hydrogen include deuterium (D) and tritium (T). Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed.

Compounds in accordance with Formula (I) can be administered by any means suitable for the condition to be treated, which can depend on the need for site-specific treatment or quantity of Formula (I) compound to be delivered.

Also embraced within this invention is a class of pharmaceutical compositions comprising at least one compound of Formula (I); and one or more non-toxic, pharmaceutically-acceptable carriers and/or diluents and/or adjuvants (collectively referred to herein as "carrier" materials) and, if desired, other active ingredients. The compounds of Formula (I) may be administered by any suitable route, preferably in the form of a pharmaceutical composition adapted to such a route, and in a dose effective for the treatment intended. The compounds and compositions of the present invention may, for example, be administered orally, mucosally, or parentally including intravascularly, intravenously, intraperitoneally, subcutaneously, intramuscularly, and intrasternally in dosage unit formulations containing conventional pharmaceutically acceptable carriers, adjuvants, and vehicles. For example, the pharmaceutical carrier may contain a mixture of mannitol or lactose and microcrystalline cellulose. The mixture may contain additional components such as a lubricating agent, e.g., magnesium stearate and a disintegrating agent such as crospovidone. The carrier mixture may be filled into a gelatin capsule or compressed as a tablet. The pharmaceutical composition may be administered as an oral dosage form or an infusion, for example.

For oral administration, the pharmaceutical composition may be in the form of, for example, a tablet, capsule, liquid capsule, suspension, or liquid. The pharmaceutical composition is preferably made in the form of a dosage unit containing a particular amount of the active ingredient. For example, the pharmaceutical composition may be provided as a tablet or capsule comprising an amount of active ingredient in the range of from about 1 to 2000 mg, preferably from about 1 to 500 mg, and more preferably from about 5 to 150 mg. A suitable daily dose for a human or other mammal may vary widely depending on the condition of the patient and other factors, but, can be determined using routine methods.

Any pharmaceutical composition contemplated herein can, for example, be delivered orally via any acceptable and suitable oral preparations. Exemplary oral preparations, include, but are not limited to, for example, tablets, troches, lozenges, aqueous and oily suspensions, dispersible powders or granules, emulsions, hard and soft capsules, syrups, and elixirs. Pharmaceutical compositions intended for oral administration can be prepared according to any methods known in the art for manufacturing pharmaceutical compositions intended for oral administration. In order to provide pharmaceutically palatable preparations, a pharmaceutical composition in accordance with the invention can contain at least one agent selected from sweetening agents, flavoring agents, coloring agents, demulcents, antioxidants, and preserving agents.

A tablet can, for example, be prepared by admixing at least one compound of Formula (I) with at least one non-toxic pharmaceutically acceptable excipient suitable for the manufacture of tablets. Exemplary excipients include, but are not limited to, for example, inert diluents, such as, for example, calcium carbonate, sodium carbonate, lactose, calcium phosphate, and sodium phosphate; granulating and disintegrating agents, such as, for example, microcrystalline cellulose, sodium croscarmellose, corn starch, and alginic acid; binding agents, such as, for example, starch, gelatin, polyvinyl-pyrrolidone, and acacia; and lubricating agents, such as, for example, magnesium stearate, stearic acid, and talc. Additionally, a tablet can either be uncoated, or coated by known techniques to either mask the bad taste of an unpleasant tasting drug, or delay disintegration and absorption of the active ingredient in the gastrointestinal tract thereby sustaining the effects of the active ingredient for a longer period. Exemplary water soluble taste masking materials, include, but are not limited to, hydroxypropyl-methylcellulose and hydroxypropyl-cellulose. Exemplary time delay materials, include, but are not limited to, ethyl cellulose and cellulose acetate butyrate.

Hard gelatin capsules can, for example, be prepared by mixing at least one compound of Formula (I) with at least one inert solid diluent, such as, for example, calcium carbonate; calcium phosphate; and kaolin.

Soft gelatin capsules can, for example, be prepared by mixing at least one compound of Formula (I) with at least one water soluble carrier, such as, for example, polyethylene glycol; and at least one oil medium, such as, for example, peanut oil, liquid paraffin, and olive oil.

An aqueous suspension can be prepared, for example, by admixing at least one compound of Formula (I) with at least one excipient suitable for the manufacture of an aqueous suspension. Exemplary excipients suitable for the manufacture of an aqueous suspension, include, but are not limited to, for example, suspending agents, such as, for example, sodium carboxymethylcellulose, methylcellulose, hydroxypropylmethyl-cellulose, sodium alginate, alginic acid, polyvinyl-pyrrolidone, gum tragacanth, and gum acacia; dispersing or wetting agents, such as, for example, a naturally-occurring phosphatide, e.g., lecithin; condensation products of alkylene oxide with fatty acids, such as, for example, polyoxyethylene stearate; condensation products of ethylene oxide with long chain aliphatic alcohols, such as, for example heptadecaethylene-oxycetanol; condensation products of ethylene oxide with partial esters derived from fatty acids and hexitol, such as, for example, polyoxyethylene sorbitol monooleate; and condensation products of ethylene oxide with partial esters derived from fatty acids and hexitol anhydrides, such as, for example, polyethylene sorbitan monooleate. An aqueous suspension can also contain at least one preservative, such as, for example, ethyl and n-propyl p-hydroxybenzoate; at least one coloring agent; at least one flavoring agent; and/or at least one sweetening agent, including but not limited to, for example, sucrose, saccharin, and aspartame.

Oily suspensions can, for example, be prepared by suspending at least one compound of Formula (I) in either a vegetable oil, such as, for example, arachis oil; olive oil; sesame oil; and coconut oil; or in mineral oil, such as, for example, liquid paraffin. An oily suspension can also contain at least one thickening agent, such as, for example, beeswax; hard paraffin; and cetyl alcohol. In order to provide a palatable oily suspension, at least one of the sweetening agents already described hereinabove, and/or at least one flavoring agent can be added to the oily suspension. An oily suspension can further contain at least one preservative, including, but not limited to, for example, an anti-oxidant, such as, for example, butylated hydroxyanisol, and alpha-tocopherol.

Dispersible powders and granules can, for example, be prepared by admixing at least one compound of Formula (I) with at least one dispersing and/or wetting agent; at least one suspending agent; and/or at least one preservative. Suitable dispersing agents, wetting agents, and suspending agents are as already described above. Exemplary preservatives include, but are not limited to, for example, anti-oxidants, e.g., ascorbic acid. In addition, dispersible powders and granules can also contain at least one excipient, including, but not limited to, for example, sweetening agents; flavoring agents; and coloring agents.

An emulsion of at least one compound of Formula (I) can, for example, be prepared as an oil-in-water emulsion. The oily phase of the emulsions comprising compounds of Formula (I) may be constituted from known ingredients in a known manner. The oil phase can be provided by, but is not limited to, for example, a vegetable oil, such as, for example, olive oil and arachis oil; a mineral oil, such as, for example, liquid paraffin; and mixtures thereof. While the phase may comprise merely an emulsifier, it may comprise a mixture of at least one emulsifier with a fat or an oil or with both a fat and an oil. Suitable emulsifying agents include, but are not limited to, for example, naturally-occurring phosphatides, e.g., soy bean lecithin; esters or partial esters derived from fatty acids and hexitol anhydrides, such as, for example, sorbitan monooleate; and condensation products of partial esters with ethylene oxide, such as, for example, polyoxyethylene sorbitan monooleate. Preferably, a hydrophilic emulsifier is included together with a lipophilic emulsifier which acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base which forms the oily dispersed phase of the cream formulations. An emulsion can also contain a sweetening agent, a flavoring agent, a preservative, and/or an antioxidant. Emulsifiers and emulsion stabilizers suitable for use in the formulation of the present invention include Tween 60, Span 80, cetostearyl alcohol, myristyl alcohol, glyceryl monostearate, sodium lauryl sulfate, glyceryl distearate alone or with a wax, or other materials well known in the art.

The compounds of Formula (I) can, for example, also be delivered intravenously, subcutaneously, and/or intramuscularly via any pharmaceutically acceptable and suitable injectable form. Exemplary injectable forms include, but are not limited to, for example, sterile aqueous solutions comprising acceptable vehicles and solvents, such as, for example, water, Ringer's solution, and isotonic sodium chloride solution; sterile oil-in-water microemulsions; and aqueous or oleaginous suspensions.

Formulations for parenteral administration may be in the form of aqueous or non-aqueous isotonic sterile injection solutions or suspensions. These solutions and suspensions may be prepared from sterile powders or granules using one or more of the carriers or diluents mentioned for use in the formulations for oral administration or by using other suitable dispersing or wetting agents and suspending agents. The compounds may be dissolved in water, polyethylene glycol, propylene glycol, ethanol, corn oil, cottonseed oil, peanut oil, sesame oil, benzyl alcohol, sodium chloride, tragacanth gum, and/or various buffers. Other adjuvants and modes of administration are well and widely known in the pharmaceutical art.

The active ingredient may also be administered by injection as a composition with suitable carriers including saline, dextrose, or water, or with cyclodextrin (i.e., CAPTISOL®), cosolvent solubilization (i.e., propylene glycol) or micellar solubilization (i.e., Tween 80).

The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

A sterile injectable oil-in-water microemulsion can, for example, be prepared by 1) dissolving at least one compound of Formula (I) in an oily phase, such as, for example, a mixture of soybean oil and lecithin; 2) combining the Formula (I) containing oil phase with a water and glycerol mixture; and 3) processing the combination to form a microemulsion.

A sterile aqueous or oleaginous suspension can be prepared in accordance with methods already known in the art. For example, a sterile aqueous solution or suspension can be prepared with a non-toxic parenterally-acceptable diluent or solvent, such as, for example, 1,3-butane diol; and a sterile oleaginous suspension can be prepared with a sterile non-toxic acceptable solvent or suspending medium, such as, for example, sterile fixed oils, e.g., synthetic mono- or diglycerides; and fatty acids, such as, for example, oleic acid.

Pharmaceutically acceptable carriers, adjuvants, and vehicles that may be used in the pharmaceutical compositions of this invention include, but are not limited to, ion exchangers, alumina, aluminum stearate, lecithin, self-emulsifying drug delivery systems (SEDDS) such as d-alpha-tocopherol polyethyleneglycol 1000 succinate, surfactants used in pharmaceutical dosage forms such as Tweens, polyethoxylated castor oil such as CREMOPHOR® surfactant (BASF), or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as alpha-, beta-, and gamma-cyclodextrin, or chemically modified derivatives such as hydroxyalkylcyclodextrins, including 2- and 3-hydroxypropyl-cyclodextrins, or other solubilized derivatives may also be advantageously used to enhance delivery of compounds of the formulae described herein.

The pharmaceutically active compounds of this invention can be processed in accordance with conventional methods of pharmacy to produce medicinal agents for administration to patients, including humans and other mammals. The pharmaceutical compositions may be subjected to conventional pharmaceutical operations such as sterilization and/or may contain conventional adjuvants, such as preservatives, stabilizers, wetting agents, emulsifiers, buffers etc. Tablets and pills can additionally be prepared with enteric coatings. Such compositions may also comprise adjuvants, such as wetting, sweetening, flavoring, and perfuming agents.

The amounts of compounds that are administered and the dosage regimen for treating a disease condition with the compounds and/or compositions of this invention depends on a variety of factors, including the age, weight, sex, the medical condition of the subject, the type of disease, the severity of the disease, the route and frequency of administration, and the particular compound employed. Thus, the dosage regimen may vary widely, but can be determined routinely using standard methods. A daily dose of about 0.001 to 100 mg/kg body weight, preferably between about 0.005 and about 50 mg/kg body weight and most preferably between about 0.01 to 10 mg/kg body weight, may be appropriate. The daily dose can be administered in one to four doses per day.

For therapeutic purposes, the active compounds of this invention are ordinarily combined with one or more adjuvants appropriate to the indicated route of administration. If administered orally, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose.

Pharmaceutical compositions of this invention comprise the compound of Formula (I), or a prodrug thereof, and optionally an additional agent selected from any pharmaceutically acceptable carrier, adjuvant, and vehicle. Alternate compositions of this invention comprise a compound of the Formula (I) described herein, or a prodrug thereof, and a pharmaceutically acceptable carrier, adjuvant, or vehicle.

Utility

The compounds of Formula (I) are useful for the treatment of cancer, for example, cancers dependent upon Notch activation. Notch activation has been implicated in the pathogenesis of various solid tumors including ovarian, pancreatic, as well as breast cancer and hematologic tumors such as leukemias, lymphomas, and multiple myeloma.

In one embodiment, a method is provided for treating cancer comprising administering to a mammal in need thereof a compound of Formula (I). The method of this embodiment can be used to treat a variety of cancers, including, but not limited to, bladder cancer, breast cancer, colorectal cancer, gastric cancer, head and neck cancer, kidney cancer, liver cancer, lung cancer including non-small cell lung cancer (NSCLC), ovarian cancer, pancreatic cancer, gall bladder cancer, prostate cancer, thyroid cancer, osteosarcoma, rhabdomyosarcoma, malignant fibrous histiocytoma (MFH), fibrosarcoma, glioblastomas/astrocytomas, neuroblastoma, melanoma, T-cell acute lymphoblastic leukemia (T-ALL), and mesothelioma. For example, the method of this embodiment is used to treat breast cancer, colon cancer, or pancreatic cancer. Preferably, the mammal is a human. For example, a therapeutically effective amount for treating cancer may be administered in the method of the present embodiment. Routes of administration in the present embodiment include parenteral administration and oral administration.

In one embodiment, a method is provided for treating cancer comprising administering to a mammal in need thereof at least one compound of Formula (I) wherein said cancer is colorectal cancer. Preferably, the mammal is a human. For example, a therapeutically effective amount for treating cancer may be administered in the method of the present embodiment. Routes of administration in the present embodiment include parenteral administration and oral administration.

In one embodiment, a method is provided for treating cancer comprising administering to a mammal in need thereof at least one compound of Formula (I) wherein said cancer is triple negative breast cancer. Preferably, the mammal is a human. For example, a therapeutically effective amount for treating cancer may be administered in the method of the present embodiment. Routes of administration in the present embodiment include parenteral administration and oral administration.

In one embodiment, a method is provided for treating cancer comprising administering to a mammal in need thereof at least one compound of Formula (I) wherein said cancer is non-small cell lung cancer. Preferably, the mammal is a human. For example, a therapeutically effective amount for treating cancer may be administered in the method of the present embodiment. Routes of administration in the present embodiment include parenteral administration and oral administration.

In one embodiment, a method is provided for treating cancer comprising administering to a mammal in need thereof at least one compound of Formula (I) wherein said cancer is pancreatic cancer. Preferably, the mammal is a human. For example, a therapeutically effective amount for treating cancer may be administered in the method of the present embodiment. Routes of administration in the present embodiment include parenteral administration and oral administration.

In one embodiment, a method is provided for treating cancer comprising administering to a mammal in need thereof at least one compound of Formula (I) wherein said cancer is ovarian cancer. Preferably, the mammal is a human. For example, a therapeutically effective amount for treating cancer may be administered in the method of the present embodiment. Routes of administration in the present embodiment include parenteral administration and oral administration.

In one embodiment, a method is provided for treating cancer comprising administering to a mammal in need thereof at least one compound of Formula (I) wherein said cancer is melanoma. Preferably, the mammal is a human. For example, a therapeutically effective amount for treating cancer may be administered in the method of the present embodiment. Routes of administration in the present embodiment include parenteral administration and oral administration.

In one embodiment, the use of at least one compound of Formula (I) in the manufacture of a medicament for the treatment of cancer is provided. Preferably, in the present embodiment, cancers subject to treatment include one or more of bladder cancer, breast cancer, colorectal cancer, gastric cancer, head and neck cancer, kidney cancer, liver cancer, lung cancer including non-small cell lung cancer (NSCLC), ovarian cancer, pancreatic cancer, gall bladder cancer, prostate cancer, thyroid cancer, osteosarcoma, rhabdomyosarcoma, malignant fibrous histiocytoma (MFH), fibrosarcoma, glioblastomas/astrocytomas, neuroblastoma, melanoma, T-cell acute lymphoblastic leukemia (T-ALL), and mesothelioma. Suitable medicaments of the present embodiment include medicaments for parenteral administration, such as, for example, solutions and suspensions and medicaments for oral administration, such as, for example, tablets, capsules, solutions, and suspensions.

One embodiment at least one compound of Formula (I) for use in therapy in treating cancer. In the present embodiment, cancers subject to treatment include one or more of bladder cancer, breast cancer, colorectal cancer, gastric cancer, head and neck cancer, kidney cancer, liver cancer, lung cancer including non-small cell lung cancer (NSCLC), ovarian cancer, pancreatic cancer, gall bladder cancer, prostate cancer, thyroid cancer, osteosarcoma, rhabdomyosarcoma, malignant fibrous histiocytoma (MFH), fibrosarcoma, glioblastomas/astrocytomas, neuroblastoma, melanoma, T-cell acute lymphoblastic leukemia (T-ALL), and mesothelioma.

In one embodiment, a method is provided for treating cancer in a mammal wherein the cancer is dependent upon Notch activation, comprising administering to the patient at least one compound of Formula (I). The method of this embodiment can be used to treat a variety of cancers, including, but not limited to, bladder cancer, breast cancer, colorectal cancer, gastric cancer, head and neck cancer, kidney cancer, liver cancer, lung cancer including non-small cell lung cancer (NSCLC), ovarian cancer, pancreatic cancer, gall bladder cancer, prostate cancer, thyroid cancer, osteosarcoma, rhabdomyosarcoma, malignant fibrous histiocytoma (MFH), fibrosarcoma, glioblastomas/astrocytomas, neuroblastoma, melanoma, T-cell acute lymphoblastic leukemia (T-ALL), and mesothelioma. Preferably, the method of this embodiment is used to treat breast cancer, colon cancer, or pancreatic cancer. Preferably, the mammal is a human. For example, a therapeutically effective amount for treating cancer may be administered in the method of the present embodiment. Suitable routes of administration include parenteral administration and oral administration.

In treating cancer, a combination of chemotherapeutic agents and/or other treatments (e.g., radiation therapy) is often advantageous. The second (or third) agent may have the same or different mechanism of action than the primary therapeutic agent. For example, drug combinations may be employed wherein the two or more drugs being administered act in different manners or in different phases of the cell cycle, and/or where the two or more drugs have nonoverlapping toxicities or side effects, and/or where the drugs being combined each has a demonstrated efficacy in treating the particular disease state manifested by the patient.

In one embodiment, a method is provided for treating cancer comprising administering to a mammal in need thereof at least one compound of Formula (I); and administering one or more additional anticancer agents.

The phrase "additional anticancer agent" refers to a drug selected from any one or more of the following: alkylating agents (including nitrogen mustards, alkyl sulfonates, nitrosoureas, ethylenimine derivatives, and triazenes); anti-angiogenics (including matrix metalloproteinase inhibitors); antimetabolites (including adenosine deaminase inhibitors, folic acid antagonists, purine analogues, and pyrimidine analogues); antibiotics or antibodies (including monoclonal antibodies, CTLA-4 antibodies, anthracyclines); aromatase inhibitors; cell-cycle response modifiers; enzymes; farnesyl-protein transferase inhibitors; hormonal and antihormonal agents and steroids (including synthetic analogs, glucocorticoids, estrogens/anti-estrogens [e.g., SERMs], androgens/anti-androgens, progestins, progesterone receptor agonists, and luteinizing hormone-releasing [LHRH] agonists and antagonists); insulin-like growth factor (IGF)/insulin-like growth factor receptor (IGFR) system modulators (including IGFR1 inhibitors); integrin-signaling inhibitors; kinase inhibitors (including multi-kinase inhibitors and/or inhibitors of Src kinase or Src/abl, cyclin dependent kinase [CDK] inhibitors, panHer, Her-1 and Her-2 antibodies, VEGF inhibitors, including anti-VEGF antibodies, EGFR inhibitors, mitogen-activated protein [MAP] inhibitors, MET inhibitors, MEK inhibitors, Aurora kinase inhibitors, PDGF inhibitors, and other tyrosine kinase inhibitors or serine/threonine kinase inhibitors; microtubule-disruptor agents, such as ecteinascidins or their analogs and derivatives; microtubule-stabilizing agents such as taxanes, and the naturally-occurring epothilones and their synthetic and semi-synthetic analogs; microtubule-binding, destabilizing agents (including vinca alkaloids); topoisomerase inhibitors; prenyl-protein transferase inhibitors; platinum coordination complexes; signal transduction inhibitors; and other agents used as anti-cancer and cytotoxic agents such as biological response modifiers, growth factors, and immune modulators.

Accordingly, the compounds of the present invention may be administered in combination with other anti-cancer treatments useful in the treatment of cancer or other proliferative diseases. The invention herein further comprises use of at least one compound of Formula (I) in preparing medicaments for the treatment of cancer, and/or it comprises the packaging of a compound of Formula (I) herein together with instructions that the compound be used in combination with other anti-cancer or cytotoxic agents and treatments for the treatment of cancer. The present invention further comprises combinations of at least one compound of Formula (I); and one or more additional agents in kit form, e.g., where they are packaged together or placed in separate packages to be sold together as a kit, or where they are packaged to be formulated together.

In one embodiment, a method is provided for treating cancer comprising administering to a mammal in need thereof at least one compound of Formula (I); administering dasatinib; and optionally, one or more additional anticancer agents.

In one embodiment, a method is provided for treating cancer comprising administering to a mammal in need thereof at least one compound of Formula (I); administering paclitaxel; and optionally, one or more additional anticancer agents.

In one embodiment, a method is provided for treating cancer comprising administering to a mammal in need thereof at least one compound of Formula (I); administering tamoxifen; and optionally, one or more additional anticancer agents.

In one embodiment, a method is provided for treating cancer comprising administering to a mammal in need thereof at least one compound of Formula (I); administering a glucocorticoid; and optionally, one or more additional anticancer agents. An example of a suitable glucocorticoid is dexamethasone.

In one embodiment, a method is provided for treating cancer comprising administering to a mammal in need thereof at least one compound of Formula (I); administering carboplatin; and optionally, one or more additional anticancer agents.

The compounds of the present invention can be formulated or co-administered with other therapeutic agents that are selected for their particular usefulness in addressing side effects associated with the aforementioned conditions. For example, compounds of the invention may be formulated with agents to prevent nausea, hypersensitivity and gastric irritation, such as antiemetics, and $H_1$ and $H_2$ antihistaminics.

In one embodiment, pharmaceutical compositions are provided comprising at least one compound of Formula (I); one or more additional agents selected from a kinase inhibitory agent (small molecule, polypeptide, and antibody), an immunosuppressant, an anticancer agent, an anti-viral agent, anti-inflammatory agent, antifungal agent, antibiotic, or an anti-vascular hyperproliferation compound; and any pharmaceutically acceptable carrier, adjuvant or vehicle.

The above other therapeutic agents, when employed in combination with the compounds of the present invention, may be used, for example, in those amounts indicated in the *Physicians' Desk Reference* (PDR) or as otherwise determined by one of ordinary skill in the art. In the methods of the present invention, such other therapeutic agent(s) may be administered prior to, simultaneously with, or following the administration of the inventive compounds.

The specific dose level and frequency of dosage for any particular subject however, may be varied and generally depends on a variety of factors, including, but not limited to, for example, the bioavailability of the specific compound of Formula (I) in the administered form, metabolic stability and length of action of the specific compound of Formula (I), species, body weight, general health, sex, diet of subject, mode and time of administration, rate of excretion, drug combination, and severity of the particular condition. For example, a daily dose of about 0.001 to 100 mg/kg body weight, preferably between about 0.005 and about 50 mg/kg body weight and most preferably between about 0.01 to 10 mg/kg body weight, may be appropriate. The daily dose can be administered in one to four doses per day.

The administration can be continuous, i.e., every day, or intermittently. The terms "intermittent" or "intermittently" as used herein mean stopping and starting at either regular or irregular intervals. For example, intermittent administration includes administration one to six days per week; administration in cycles (e.g., daily administration for two to eight consecutive weeks followed by a rest period with no administration for up to one week); or administration on alternate days.

In one embodiment, the at least one compound of Formula (I) is administered continuously to a patient in need thereof, one or more times daily. For example, a therapeutically effective amount of the compound of Formula (I) is administered to a patient in need thereof, one or more times daily for continuous days.

In one embodiment, the at least one compound of Formula (I) is administered intermittently to a patient in need thereof, one or more times daily. For example, a therapeutically effective amount of the compound of Formula (I) is administered to a patient in need thereof, one or more times daily according to an intermittent schedule.

In one embodiment, the at least one compound of Formula (I) is administered to a patient in need thereof, one or more times daily for continuous days followed by one or more days without administration. Preferably, a therapeutically effective amount of the compound of Formula (I) is administered. Examples of continuous dosing with a drug holiday are cycles of: 7 days on treatment followed by 7 days off treatment; 14 days on treatment followed by 7 days off treatment; and 7 days on treatment followed by 14 days off treatment. A cycle of on treatment/off treatment can be repeated multiple times as required to treat a patient.

In one embodiment, the at least one compound of Formula (I) is administered to a patient in need thereof, according to an intermittent dosing schedule. Intermittent dosing schedules are repeating schedules including days in which the patient is administered the compound of Formula (I) and days in which the patient is not administered the compound of Formula (I). Examples of intermittent dosing schedules are: dosing four days each week for three continuous weeks followed by a week without dosing, and repeating on a four week interval; dosing five days each week for two continuous weeks followed by a week without dosing, and repeating on a three week interval; and dosing four days each week for one week followed by two weeks without dosing, and repeating on a three week interval. Preferably, a therapeutically effective amount of the compound of Formula (I) is administered.

In one embodiment, at least one compound of Formula (I) is administered on one day, followed by 6 days of rest, and repeated on a weekly schedule.

In one embodiment, at least one compound of Formula (I) is administered on one day, followed by 6 days of rest, and repeated on a weekly schedule for 1 to 4 weeks, and then followed by one week or rest. For example, the compound of Formula (I) is administered on one day, followed by 6 days of rest for three weeks, and then followed by one week of rest. This four week cycle can be repeated one or more times.

In one embodiment, at least one compound of Formula (I) is administered on two consecutive days, followed by 5 days of rest, and repeated on a weekly schedule.

In one embodiment, at least one compound of Formula (I) is administered on three consecutive days followed by four days of rest, and repeated on a weekly schedule.

In one embodiment, at least one compound of Formula (I) is administered on one day, followed by 10 to 13 days of rest.

In one embodiment, at least one compound of Formula (I) is administered once each day (QD). This embodiment includes once daily oral administration.

In one embodiment, at least one compound of Formula (I) is administered twice each day (BID). This embodiment includes twice daily oral administration.

In one embodiment, at least one compound of Formula (I) is administered on alternate days: one day on followed by one day of rest. This two day cycle can be repeated one or more times.

Methods of Preparation

The compounds of the present invention can be prepared in a number of ways well known to one skilled in the art of organic synthesis. The compounds of the present invention can be synthesized using the methods described below, together with synthetic methods known in the art of synthetic organic chemistry, or variations thereon as appreciated by those skilled in the art. Preferred methods include, but are not limited to, those described below. All references cited herein are hereby incorporated in their entirety by reference.

The compounds of this invention may be prepared using the reactions and techniques described in this section. The reactions are performed in solvents appropriate to the reagents and materials employed and are suitable for the transformations being effected. Also, in the description of the synthetic methods described below, it is to be understood that all proposed reaction conditions, including choice of solvent, reaction atmosphere, reaction temperature, duration of the experiment and work up procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents that are compatible with the reaction conditions will be readily apparent to one skilled in the art and alternate methods must then be used. This will sometimes require a judgment to modify the order of the synthetic steps or to select one particular process scheme over another in order to obtain a desired compound of the invention. It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene et al. (*Protective Groups in Organic Synthesis*, Third Edition, Wiley and Sons (1999)).

Compounds of Formula (I) may be prepared by reference to the methods illustrated in the following Schemes. As shown therein the end product is a compound having the same structural formula as Formula (I). It will be understood that any compound of Formula (I) may be produced by the schemes by the suitable selection of reagents with appropriate substitution. Solvents, temperatures, pressures, and other reaction conditions may readily be selected by one of ordinary skill in the art. Starting materials are commercially available or readily prepared by one of ordinary skill in the art. Constituents of compounds are as defined herein or elsewhere in the specification.

The synthesis of the compounds of Formula (I) can be made using the methods summarized in Schemes 1 to 7.

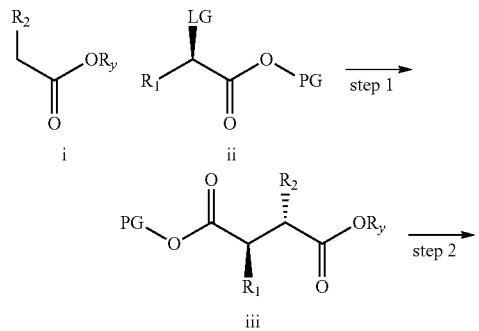

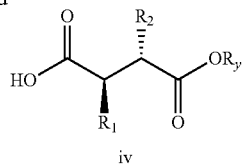

Step 1: A suitably protected acid (i) may be alkylated with compound (ii) having a suitable leaving group, such as a triflate (LG=OTf), in the presence of a base such as KHMDS to give compound (iii) as the predominant diastereomer. Compound (iii) could be used as a diastereomeric mixture or can be separated using an appropriate separation technique, such as chiral preparative chromatography, to give the pure diastereomer compound.

Step 2. The protecting group of Compound (iii) may be removed via many methods known to one skilled in the art. For example, a benzyl group may be removed by subjecting it to hydrogenation conditions using a palladium catalyst in a solvent such as methanol to provide Compound (iv).

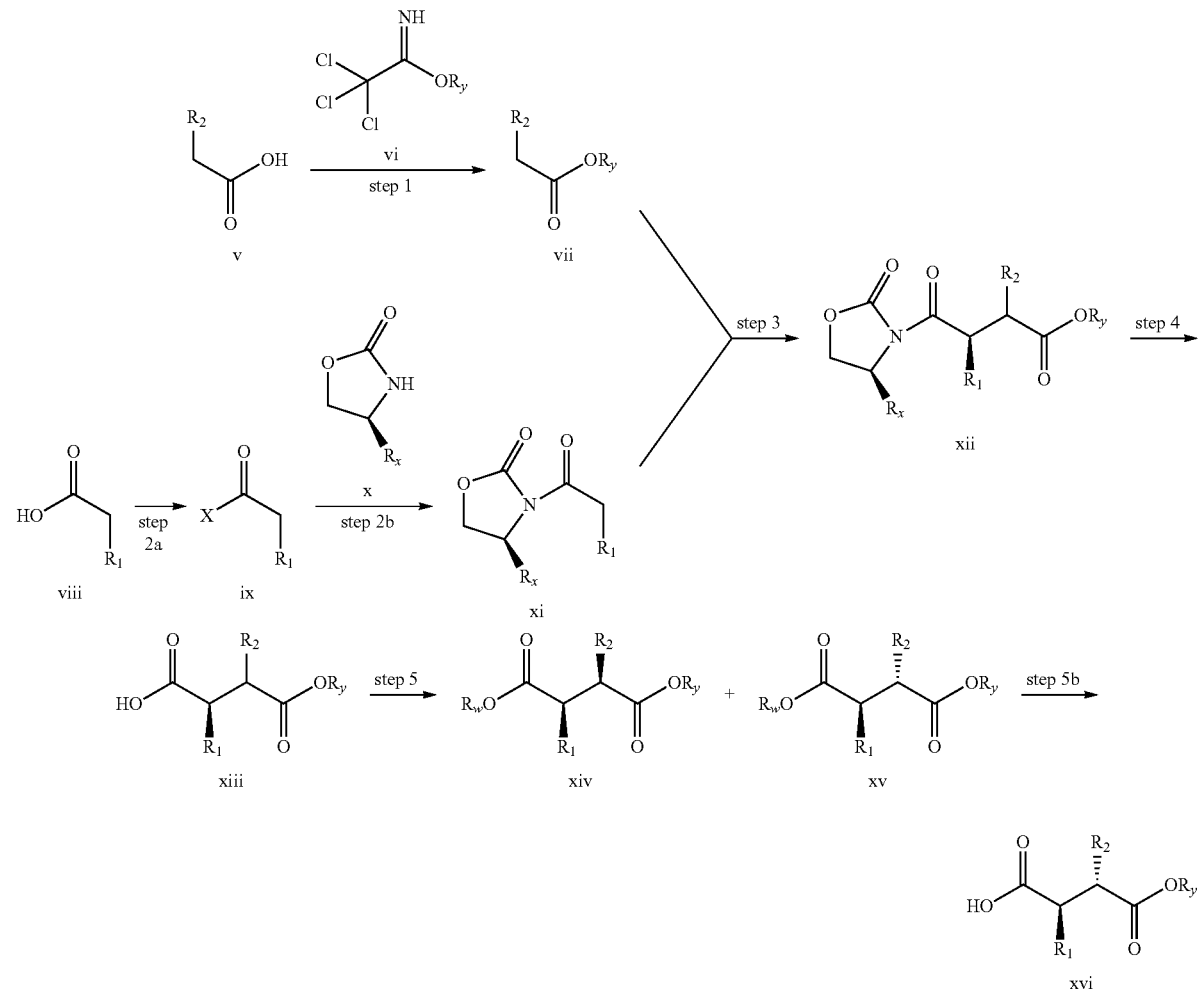

Step 1: The first step of Scheme 2 is accomplished by converting compound (v) to the ester (vii), employing one of the multiple ways known to one skilled in the art, such as treatment with a substituted acetimidate such as compound (vi) in the presence of a reagent such as boron trifluoride etherate at an appropriate temperature in a solvent such as THF.

Step 2: Acid (viii) can be converted to compound (xi) in multiple ways known to one skilled in the art. For example, treatment of acid (viii) with a reagent such as oxalyl chloride in a solvent such as DCM gives the acid chloride (ix, X=Cl). Compound (ix) can be treated with an oxazolidinone (x) under standard conditions to give compound (xi) (Evans, D. A. et al., *J. Am. Chem. Soc.*, 112:4011 (1990)).

Step 3: Compound (xi) can be converted to compound (xii) in multiple ways (Baran, P. et al., *J. Am. Chem. Soc.*, 130(34): 11546 (2008)). For example, compound (vii) is treated with a base such as LDA in a solvent such as toluene, at low temperature such as −78° C. under an inert atmosphere such as $N_2$. The resulting mixture is added to a solution of compound (xi) treated with lithium chloride and a base such as LDA in a solvent such as toluene under an inert atmosphere such as $N_2$. To the resulting mixture of the enolates of compounds (vii) and (xi) is added bis(2-ethylhexanoyloxy)copper at a low temperature such as −78° C. under an inert atmosphere such as $N_2$ and warmed to room temperature to provide compound (xii).

Step 4: Conversion of compound (xii) to (xiii) may be accomplished by treating it with hydrogen peroxide and lithium hydroxide at an appropriate temperature using a mixture of solvents such as THF/water. If necessary, the diastereomers may be separated at this point via silica gel chromatography or preparative HPLC. Alternately, the mixture may be subjected to epimerization conditions, for example by treatment with LDA and diethylaluminum chloride followed by quenching with methanol or acetic acid to enrich the desired diastereomer.

Step 5: If desired, the desired (R,S)-diastereomer may be obtained in pure form by a series of steps involving protection of the carboxylic acid, separation of the diastereomers and deprotection, common steps known to one skilled in the art. For example, the mixture of diastereomers (xiii) can be protected as the benzyl ester by treating with a reagent such as benzyl bromide in the presence of base such as potassium carbonate in a solvent such as DMF. This diastereomeric mixture can then be subjected to purification procedures, for example Preparative HPLC or silica gel chromatography. The diastereomerically pure material obtained can then be subjected to deprotection conditions (step 5b). For example, if R=Bn, the material can be treated under hydrogenation conditions using a catalyst such as palladium on carbon in a solvent such as MeOH under a hydrogen atmosphere to give acid (xvi).

Scheme 3

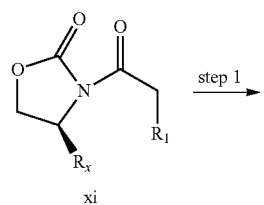

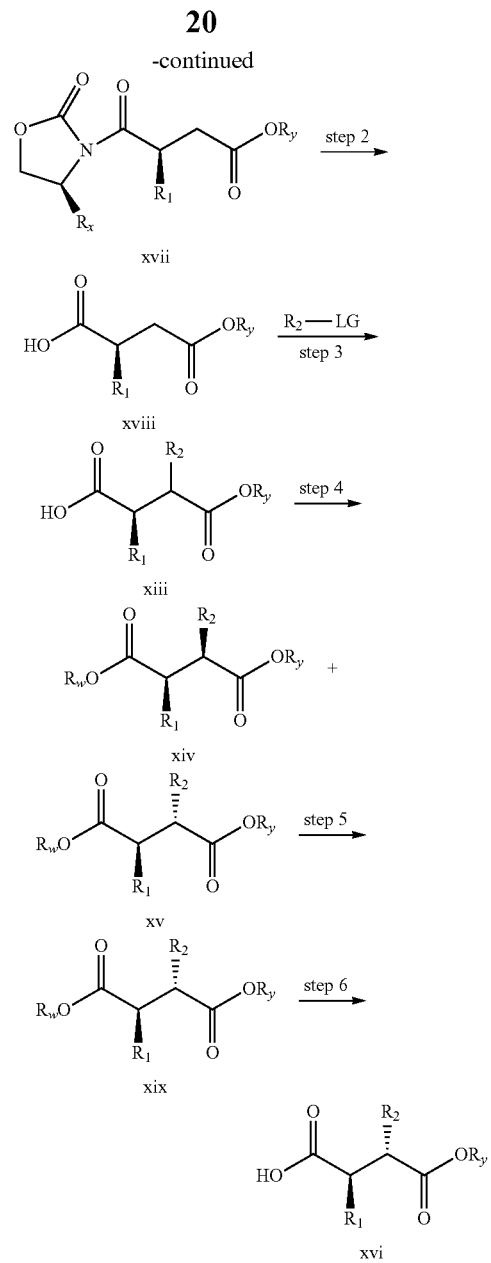

Compound (xiii) in Scheme 4 may also be prepared from compound (xi) by a synthetic sequence outlined in Scheme 3.

Step 1: The first step of Scheme 3 is accomplished by treating compound (xi) with a base such as sodium bis(trimethylsilyl)-amide in a solvent such as THF at low temperature such as −78° C. under an inert atmosphere. The resulting enolate of (xi) is treated with a reagent such as tert-butyl bromoacetate to provide compound (xvii).

Step 2: Conversion of compound (xvii) to (xviii) may be accomplished by treating compound (xvii) with hydrogen peroxide and lithium hydroxide at an appropriate temperature using a mixture of solvents such as THF/water.

Step 3: Compound (xviii) can be converted to compound (xiii) by generating the enolate of (xviii) with a base such as LDA in a solvent such as THF at low temperature such as −78° C. under an inert atmosphere and further treatment with a reagent ($R_2$-LG) bearing an appropriate leaving group (e.g., LG=triflate). Compound (xiii) may then be utilized, for example, in step 7 of Scheme 4. Alternately, the mixture may be subjected to epimerization conditions, for example by treatment with LDA and diethylaluminum chloride followed by quenching with methanol or acetic acid to enrich the desired diastereomer. Moreover, a preferred embodiment entails the installation of a moiety that may later be transformed to another substituent. For example, using a different reactant ($R_2$-LG), such as allyl bromide, installs a suitable grouping for future modifications. Epimerization conditions, as noted above, may also be employed on this compound if desired.

Step 4: The fourth step of Scheme 4 is similar to that of step 5 in Scheme 3 and may be omitted if compound (xiii) will be used directly in, for example, step 7 of Scheme 4. However, if further manipulation of, for example, $R_2$ of compound (xiii) is desired, the carboxylic acid moiety of compound (xiii) may be protected with a suitable protecting group, for example a benzyl group. Hence, compound (xiii) may be treated with a reactant such as benzyl bromide, in the presence of a base such as potassium carbonate in a suitable solvent such as DMF. The resulting mixture of diastereoisomers may be separated if desired, employing suitable conditions such as preparative HPLC, preparative chiral HPLC or silica gel chromatography, and the resulting pure desired diastereoisomer compound (xv) used in the subsequent steps.

Step 5: If the $R_2$ group in compound (xv) is the desired moiety, then step 5 may be omitted. However, if the $R_2$ group is a moiety on which further modifications is desired, this may be done at this time. For example, if $R_2$=allyl, treatment of compound (xv) under cyclopropanation conditions may provide a functional group of a preferred embodiment. Consequently, compound (xv) where $R_2$=allyl may be treated with a reagent such as diazomethane, in the presence of a catalyst such as palladium acetate in a suitable solvent such as diethyl ether at a suitable temperature such as 0° C. to afford compound (xix).

Step 6: The last step of Scheme 3 is a deprotection step, similar to step 5 of Scheme 2, and may be accomplished in several ways known to one skilled in the art. For example, for $R_w$=benzyl in compound (xix), treatment under hydrogenation conditions using a catalyst such as palladium on carbon in a solvent such as MeOH under a hydrogen atmosphere may provide compound (xvi) that may subsequently be utilized, for example, in step 7 of Scheme 4.

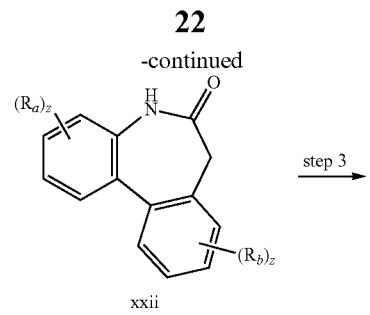

xxii

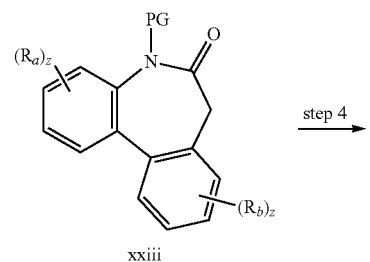

xxiii

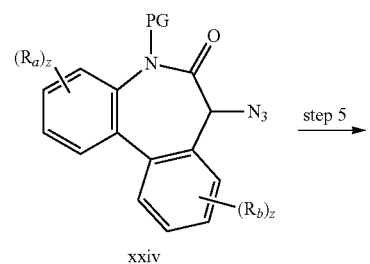

xxiv

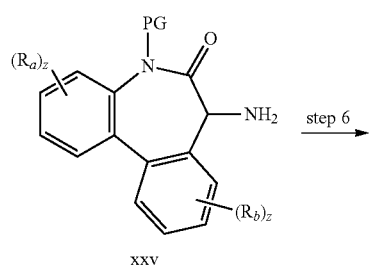

xxv

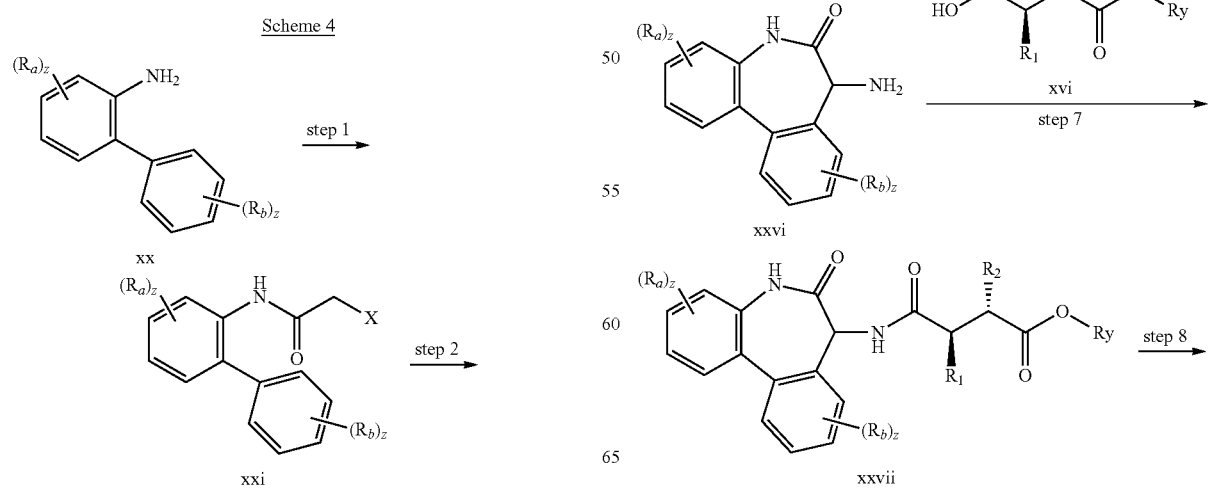

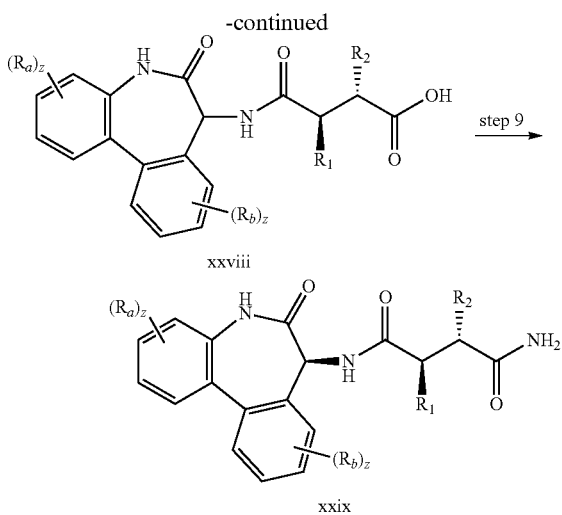

Step 1 of Scheme 4 may be accomplished by reaction of an appropriately substituted amino biphenyl (xx) with a suitably substituted acetate or acetate equivalent under a variety of conditions well known to one skilled in the art. For example, reaction of aminobiphenyl (xx) with chloroacetyl chloride in a suitable solvent such as DCM in the presence of a base such as triethylamine gives intermediate (xxi), where X=Cl.

Step 2 of Scheme 4 can be accomplished by reacting intermediate (xxi) with a suitable Lewis acid at an appropriate temperature in an appropriate solvent. For example, heating intermediate (xxi), where X=Cl, to a temperature such as 170° C. with a Lewis acid such as aluminum chloride in a solvent such as 1,2-dichlorobenzene provides intermediate (xxii).

Step 3: For further manipulation of intermediate (xxii), it may be necessary or desirable to protect the lactam nitrogen. This can be accomplished in a number of ways known to one skilled in the art. For example, intermediate (xxii) may be reacted with 4-methoxybenzyl chloride in a solvent such as THF in the presence of a base such as potassium hydroxide and a catalyst such as tetrabutylammonium bromide to give intermediate (xxiii), where PG=PMB.

Step 4: Conversion of compound (xxiii) to compound (xxiv) may be accomplished by treatment with an appropriate base in an appropriate solvent followed by treatment with an azide transfer reagent. For example, treatment of intermediate (xxiii) with LDA in THF at −78° C. followed by the addition of 2,4,6-triisopropylbenzenesulfonyl azide gives intermediate (xxiv). Alternatively, compound (xxiii) may be converted to compound (xxiv) in a two step procedure involving the installation of an appropriate leaving group and the displacement of this leaving group by azide. For example, treatment of (xxiii) with TMSI and iodine gives an intermediate iodide, which may be displaced by treatment with tetrabutylammonium azide to give (xxiv).

Step 5: The reduction of the azide functionality in intermediate (xxiv) can be accomplished by a number of methods known to one skilled in the art. Treatment of azide (xxiv) with hydrogen in the presence of an appropriate catalyst, such as palladium hydroxide on carbon, in an appropriate solvent, such as ethyl acetate, will effect reduction to amine (xxv).

Step 6: The removal of the protecting group from intermediate (xxv) can be accomplished by a number of methods apparent to one skilled in the art. When PG=PMB, the removal of the protecting group can be accomplished under acidic conditions. For example, treatment of intermediate (xxv) with a suitable acid or mixture of acids, such methanesulfonic acid in trifluoroacetic acid, at an appropriate temperature such as 70° C., will effect the transformation of compound (xxv) to compound (xxvi). Compound (xxvi) may be used as a mixture of enantiomers, or the enantiomers may be separated by a number of means known to one skilled in the art, such as chiral preparative chromatography.

Step 7: Dibenzopinone (xxvi) may be coupled to either pure diastereomer compound (xvi) or diastereomeric mixture compound (xiii) in the presence of a coupling reagent such as TBTU and a base such as TEA, in a solvent such as DMF to provide compound (xxvii) as either a diastereomerically pure compound or as a mixture of diastereoisomers, as appropriate. This mixture may be used as such in the subsequent step, or if desired, may be purified using an appropriate separation technique, such as chiral preparative chromatography to provide the diastereomerically pure compounds.

Step 8: Treatment of compound (xxvii) with an acid such as TFA at an appropriate temperature such as 0° C., in a solvent such as DCM provides compound (xxviii) as either a diastereomerically pure compound or as a mixture of diastereoisomers. This mixture may be used as such in the subsequent step, or if desired, may be purified using an appropriate separation technique, such as chiral preparative chromatography to provide the diastereomerically pure compounds.

Step 9: Conversion of compound (xxviii) to compound (xxix) may be accomplished via coupling of compound (xxviii) with an appropriate amine source such as ammonium chloride, a carbodiimide such as EDC, HOBT and a base such as TEA in a solvent such as DMF. If necessary the diastereomeric mixture can be separated using an appropriate separation technique, such as chiral preparative chromatography.

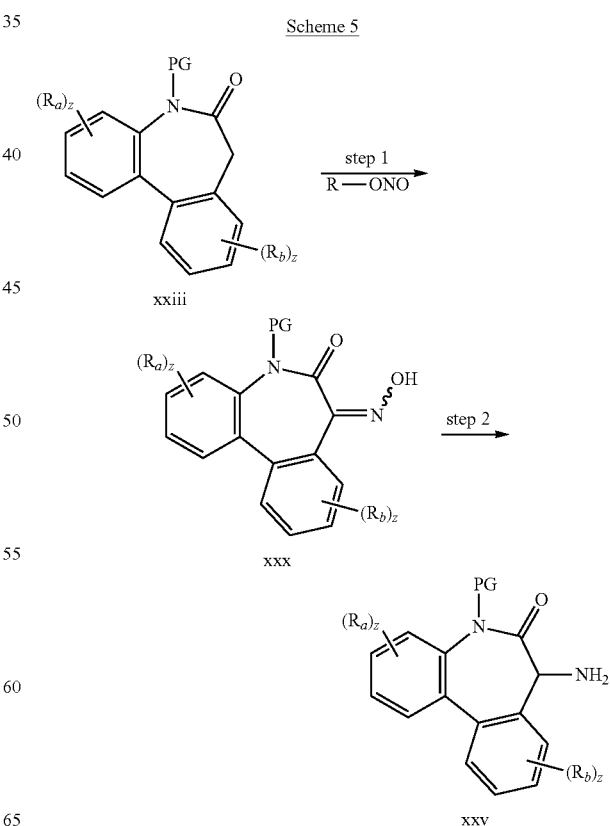

Alternatively, intermediate (xxiii) may be transformed to intermediate (xxv) as shown in Scheme 5. In step 1 of Scheme 5, intermediate (xxiii) is treated with a suitable base and an alkyl nitrite. For example, treatment of intermediate (xxiii) with potassium tert-butoxide in a solvent such as THF at a temperature such as 0° C. followed by treatment with isopentylnitrite gives intermediate (xxx).

Step 2: Reduction of the oxime in intermediate (xxx) may be accomplished by several methods, as known to one skilled in the art. For example, treatment of (xxx) with a catalyst such as palladium on carbon under a hydrogen atmosphere in a solvent such as methanol gives amine (xxv), which may be used in, for example, step 7 of Scheme 4. If an acid such as hydrochloric acid is included in the reaction, then amine (xxv) will be obtained as the corresponding salt.

Scheme 6

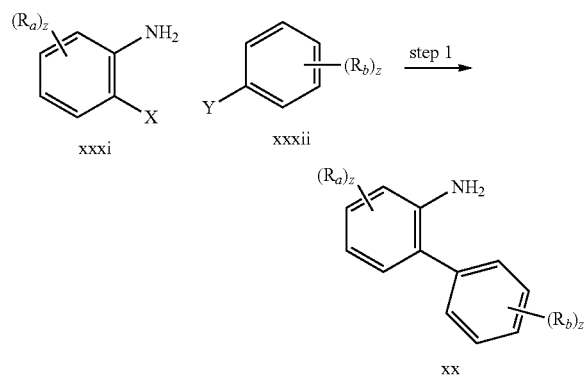

Intermediate (xx) in Scheme4 may be obtained by a transition metal mediated coupling of suitably substituted intermediates (xxxi) and (xxxii), where the groups X and Y are appropriately matched partners for a coupling reaction. For example intermediate (xxxi), where X=Br, may be coupled to intermediate (xxxii), where Y is B(OH)$_2$, in the presence of a suitable catalyst, such as palladium(II) acetate, and a suitable base, such as sodium carbonate in an appropriate mixture of solvents, such as water and poly(ethylene glycol) 2000 at a suitable temperature, such as 120° C. to give intermediate (xx), which may be used, for example, in step 1 of Scheme 4

Scheme 7

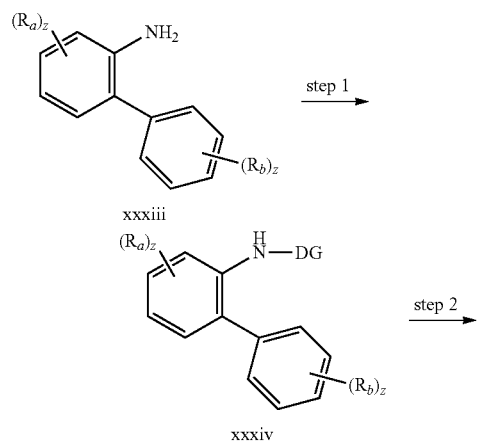

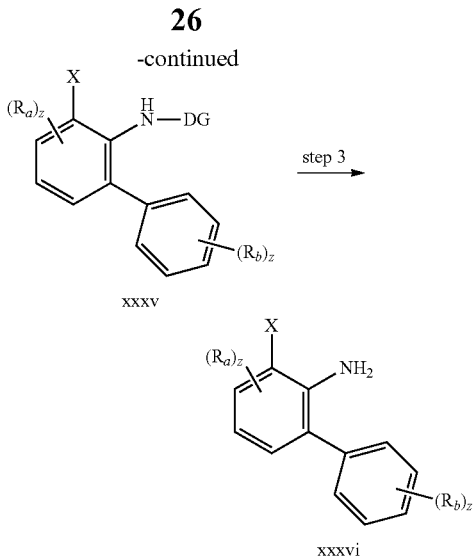

Intermediate (xx) from Scheme 4 may also be prepared by functionalization of a simpler aminobiphenyl (xxxiii), as shown in Scheme 7. It may be necessary or desirable to install a directing group prior to other manipulations, as shown in step 1. This transformation may be effected using a variety of conditions known to one skilled in the art. For example, for DG=Boc, the transformation may be accomplished by reacting intermediate (xxxiii) with di-t-butyl dicarbonate in an appropriate solvent such as dichloroethane at an appropriate temperature, such as 70° C., to give intermediate (xxxiv).

Step 2: Installation of the desired functional group(s) on intermediate (xxxiv) may be accomplished by a number of methods known to one skilled in the art. For example, when X=Boc, deprotonation of intermediate (xxxiv) may be accomplished by the use of t-butyllithium in a solvent such as diethyl ether at an appropriate temperature, such as −30° C. Reaction of the resulting anion with an appropriate electrophile, as known to one skilled in the art, gives intermediate (xxxv). For example, use of hexachloroethane as the electrophile at room temperature provides intermediate (xxxv), where DG=Boc and X=Cl.

Step 3: If a directing group was installed in step 1, it may be necessary or desirable to remove it at this point, using a variety of conditions appropriate to the nature of the directing group, as known to one skilled in the art. For example, when DG=Boc, exposure of intermediate (xxxv) to an acid such as trifluoroacetic acid will provide intermediate (xxxvi), which can be used, for example, in step 1 of Scheme 4.

EXAMPLES

The invention is further defined in the following Examples. It should be understood that the Examples are given by way of illustration only. From the above discussion and the Examples, one skilled in the art can ascertain the essential characteristics of the invention, and without departing from the spirit and scope thereof, can make various changes and modifications to adapt the invention to various uses and conditions. As a result, the invention is not limited by the illustrative examples set forth hereinbelow, but rather is defined by the claims appended hereto.

Abbreviations

AcOH acetic acid
Bn benzyl

Boc tert-butoxycarbonyl
DAST (diethylamino)sulfur trifluoride
DCM dichloromethane
DMF dimethylformamide
DMSO dimethyl sulfoxide
EDC 1-(3-dimethylaminopropyl)-3-ethylcarbodiimide hydrochloride
Et$_2$AlCl diethyl aluminum chloride
Et$_3$N triethyl amine
Et$_2$O diethyl ether
EtOH ethanol
EtOAc ethyl acetate
equiv. equivalence
g gram
h or hr hour(s)
HOBt hydroxybenzotriazole
HPLC high pressure liquid chromatography
KHMDS potassium bis(trimethylsilyl)amide
LCMS Liquid Chromatography-Mass Spectroscopy
LDA lithium diisopropylamide
MeCN acetonitrile
MeOH methanol
min minute(s)
mL milliliter
mmol millimolar
MTBE methyl tertiary butyl ether
NaHMDS sodium bis(trimethylsilyl)amide
n-BuLi n-butyl lithium
NH$_4$OAc ammonium acetate
PdCl$_2$(dppf) [1,1'-bis(diphenylphosphino)ferrocene]dichloropalladium(II)
Pd(OAc)$_2$ palladium acetate
RT retention time
t-Bu tertiary butyl
tBuOAc tertiary butyl acetate
tBuOH tertiary butyl alcohol
TBTU O-(1H-benzotriazol-1-yl)-N,N,N',N'-tetramethyluronium tetrafluoroborate
TEA triethylamine
TFA trifluoroacetic acid
Tf$_2$O trifluoromethylsulfonic anhydride
THF tetrahydrofuran
TMS trimethylsilyl Example 1

(2R,3S)-N-((7S)-6-Oxo-6,7-dihydro-5h-dibenzo[b,d]azepin-7-yl)-2,3-bis(3,3,3-trifluoropropyl)succinamide

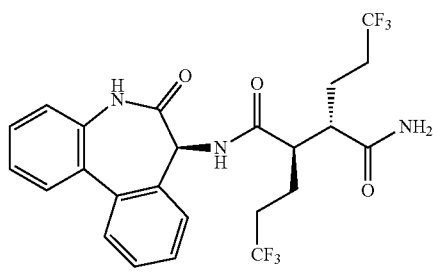

(1)

Preparation 1A: 3,3,3-Trifluoropropyl trifluoromethanesulfonate

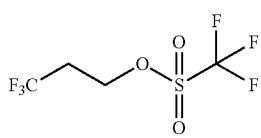

(1A)

To a cold (−25° C.), stirred solution of 2,6-lutidine (18.38 mL, 158 mmol) in DCM (120 mL) was added Tf$_2$O (24.88 mL, 147 mmol) over 3 min, and the mixture was stirred for 5 min. To the reaction mixture was added 3,3,3-trifluoropropan-1-ol (12 g, 105 mmol) over an interval of 3 min. After 2 hour, the reaction mixture was warmed to room temperature and stirred for 1 hour. The reaction mixture was concentrated to half its volume, then purified by loading directly on a silica gel column (330 g ISCO). The product was eluted with DCM to afford Preparation 1A (13.74 g, 53%) as a colorless oil.

$^1$H NMR (400 MHz, CDCl$_3$) δ ppm 4.71 (2H, t, J=6.15 Hz), 2.49-2.86 (2H, m).

Preparation 1B: (4S)-4-Benzyl-3-(5,5,5-trifluoropentanoyl)-1,3-oxazolidin-2-one

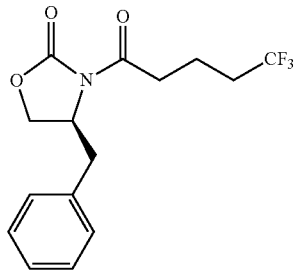

(1B)

To a stirring solution of 5,5,5-trifluoropentanoic acid (14.76 g, 95 mmol) and DMF (0.146 mL) in DCM (50 mL) was slowly added oxalyl chloride (8.27 mL, 95 mmol). After 2 h, the mixture was concentrated to dryness. A separate flask was changed with (S)-4-benzyloxazolidin-2-one (16.75 g, 95 mmol) in THF (100 mL) and then cooled to −78° C. To the solution was slowly added n-BuLi (2.5M, 37.8 mL, 95 mmol) over 10 min, stirred for 10 min, and then a solution of the above acid chloride in THF (50 mL) was slowly added over 5 min. The mixture was stirred for 30 min, and then warmed to room temperature. The mixture was quenched with saturated aqueous NH$_4$Cl, then 10% aq LiCl was then added, and the mixture was extracted with Et$_2$O. The organic layer was washed with saturated aqueous NaHCO$_3$, then with brine, then dried with MgSO$_4$, filtered and concentrated to dryness. The residue was purified by SiO$_2$ chromatography (ISCO, 330 g column, eluting with a gradient from 100% hexane to 100% EtOAc) to afford the product Preparation 1B; (25.25 g, 85%): $^1$H NMR (400 MHz, CDCl$_3$) δ ppm 7.32-7.39 (2H, m), 7.30 (1H, d, J=7.05 Hz), 7.18-7.25 (2H, m), 4.64-4.74 (1H, m), 4.17-4.27 (2H, m), 3.31 (1H, dd, J=13.35, 3.27 Hz), 3.00-3.11 (2H, m), 2.79 (1H, dd, J=13.35, 9.57 Hz), 2.16-2.28 (2H, m), 1.93-2.04 (2H, m).

Preparation 1C: tert-Butyl (3R)-3-(((4S)-4-benzyl-2-oxo-1,3-oxazolidin-3-yl)carbonyl)-6,6,6-trifluorohexanoate

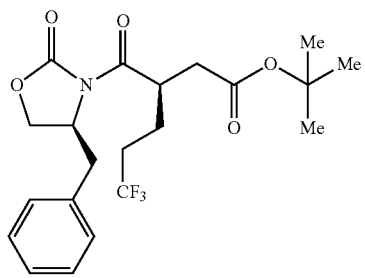

(1C)

To a cold (−78° C.), stirred solution of Preparation 1B (3.03 g, 9.61 mmol) in THF (20 mL) was added NaHMDS (1.0M in THF) (10.6 mL, 10.60 mmol) under a nitrogen atmosphere. After 2 hours, tert-butyl 2-bromoacetate (5.62 g, 28.8 mmol) was added neat via syringe at −78° C., and stirring was maintained at the same temperature. After 6 hours, the reaction mixture was warmed to room temperature. The reaction mixture was partitioned between saturated NH$_4$Cl and EtOAc. The organic phase was separated, and the aqueous phase was extracted with EtOAc (3×). The combined organics were washed with brine, dried with Na$_2$SO$_4$, filtered and concentrated under reduced pressure. The residue was purified by flash chromatography (Teledyne ISCO CombiFlash Rf, 5% to 100% solvent A/B=hexanes/EtOAc, REDISEP® SiO$_2$ 120 g). Concentration of the appropriate fractions provided Preparation 1C (2.79 g, 67.6%) as a colorless viscous oil: $^1$H NMR (400 MHz, CDCl$_3$) δ ppm 7.34 (2H, d, J=7.30 Hz), 7.24-7.32 (3H, m), 4.62-4.75 (1H, m, J=10.17, 6.89, 3.43, 3.43 Hz), 4.15-4.25 (3H, m), 3.35 (1H, dd, J=13.60, 3.27 Hz), 2.84 (1H, dd, J=16.62, 9.57 Hz), 2.75 (1H, dd, J=13.35, 10.07 Hz), 2.47 (1H, dd, J=16.62, 4.78 Hz), 2.11-2.23 (2H, m), 1.90-2.02 (1H, m), 1.72-1.84 (1H, m), 1.44 (9H, s).

Preparation 1D: (2R)-2-(2-tert-Butoxy-2-oxoethyl)-5,5,5-trifluoropentanoic acid

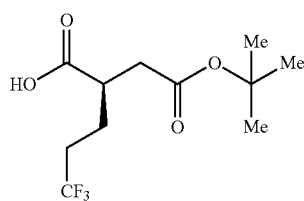

(1D)

To a cool (0° C.), stirred solution of Preparation 1C (2.17 g, 5.05 mmol) in THF (50 mL) and water (15 mL) was added a solution of LiOH (0.242 g, 10.11 mmol) and H$_2$O$_2$ (2.065 mL, 20.21 mmol) in H$_2$O (2 mL). After 10 min, the reaction mixture was removed from the ice bath, stirred for 1 h, and then recooled to 0° C. Saturated aqueous NaHCO$_3$ (25 mL) and saturated aqueous Na$_2$SO$_3$ (25 mL) were added to the reaction, stirred for 10 min, and then partially concentrated. The resulting mixture was extracted with DCM (2×), cooled with ice and made acidic with concentrated HCl to pH 3. The mixture was saturated with solid NaCl, extracted with EtOAc (3×), and then dried over MgSO$_4$, filtered and concentrated to a colorless oil to afford Preparation 1D (1.2514 g, 92%): $^1$H NMR (400 MHz, CDCl$_3$) δ ppm 2.83-2.95 (1H, m), 2.62-2.74 (1H, m), 2.45 (1H, dd, J=16.62, 5.79 Hz), 2.15-2.27 (2H, m), 1.88-2.00 (1H, m), 1.75-1.88 (1H, m), 1.45 (9H, s).

Preparation 1E: (2R,3S)-3-(tert-Butoxycarbonyl)-6,6,6-trifluoro-2-(3,3,3-trifluoropropyl)hexanoic acid, and Preparation 1F: (2R,3R)-3-(tert-Butoxycarbonyl)-6,6,6-trifluoro-2-(3,3,3-trifluoropropyl)hexanoic acid

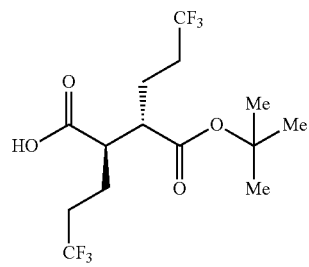

(1E)

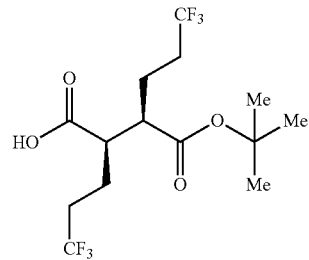

(1F)

To a cold (−78° C.), stirred solution of Preparation 1D (5 g, 18.50 mmol) in THF (60 mL) was slowly added LDA (22.2 mL, 44.4 mmol, 2.0M) over 7 min. After stirring for 2 hr, Preparation 1A (6.38 g, 25.9 mmol) was added to the reaction mixture over 3 min. After 60 min, the reaction mixture was warmed to −25° C. (ice/MeOH/dry ice) and stirred for an additional 60 min at which time saturated aqueous NH$_4$Cl was added. The separated aqueous phase was acidified with 1N HCl aq to pH 3, then extracted with Et$_2$O, washed the combined organic layers with brine (×2), dried over MgSO$_4$, filtered and concentrated to provide a 1:4 (1E: 1F) mixture (as determined by $^1$H NMR) of Preparation 1E and Preparation 1F (6.00 g, 89%) as a pale yellow solid. $^1$H NMR (500 MHz, CDCl$_3$) δ ppm 2.81 (1H, ddd, J=10.17, 6.32, 3.85 Hz), 2.63-2.76 (1H, m), 2.02-2.33 (4H, m), 1.86-1.99 (2H, m), 1.68-1.85 (2H, m), 1.47 (9H, s).

Preparation 1E: (2R,3S)-3-(tert-Butoxycarbonyl)-6,6,6-trifluoro-2-(3,3,3-trifluoropropyl)hexanoic acid, and Preparation 1F: (2R,3R)-3-(tert-Butoxycarbonyl)-6,6,6-trifluoro-2-(3,3,3-trifluoropropyl)hexanoic acid

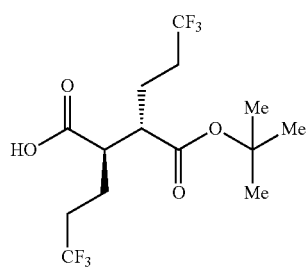

(1E)

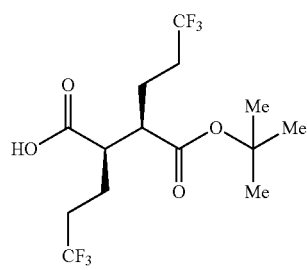

(1F)

To a cold (−78° C.), stirred solution of a mixture of Preparation 1E and Preparation 1F (5.97 g, 16.30 mmol) in THF (91 mL) was added LDA (19 mL, 38.0 mmol, 2.0M in THF/hexane/ethyl benzene) dropwise via syringe over 10 min (internal temperature never exceeded −65° C., J-KEM® probe in reaction solution), stirred for 15 min, warmed to room temperature (24° C. water bath), stirred for 15 min, cooled to −78° C. for 15 min. To the reaction mixture was added Et$_2$AlCl (41 mL, 41.0 mmol, 1M in hexane) via syringe (internal temperature never exceeded −55° C.). The reaction mixture was stirred for 10 min, warmed to room temperature (24° C. bath) for 15 min then cooled to −78° C. for 15 min. Meanwhile, a 1000 mL round bottom flask was charged with MeOH (145 mL) and precooled to −78° C. With vigorous stirring the reaction mixture was transferred via cannula over 5 min to the MeOH. The flask was removed from the bath, then ice was added followed by slow addition of 1N HCl (147 mL, 147 mmol). NOTE: gas evolution was observed as the HCl was added. The reaction mixture was allowed to warm to room temperature during which the gas evolution subsided. The reaction mixture was diluted with EtOAc (750 mL), and the aqueous layer was saturated with NaCl. The organic phase was separated, washed with a solution of potassium fluoride (8.52 g, 147 mmol) and 1N HCl (41 mL, 41.0 mmol) in water (291 mL), then washed with brine (100 mL), dried with Na$_2$SO$_4$, filtered and concentrated under vacuum. $^1$H NMR showed product was 9:1 mixture of Preparation 1E and Preparation 1F. Obtained the enriched mixture of Preparation 1E and Preparation 1F (6.12 g, >99% yield) as a dark amber solid: $^1$H NMR (400 MHz, CDCl$_3$) δ ppm 2.64-2.76 (2H, m), 2.04-2.35 (4H, m), 1.88-2.00 (2H, m), 1.71-1.83 (2H, m), 1.48 (9H, s).

Preparation 1G: (2R,3S)-1-Benzyl 4-tert-butyl 2,3-bis(3,3,3-trifluoropropyl)succinate

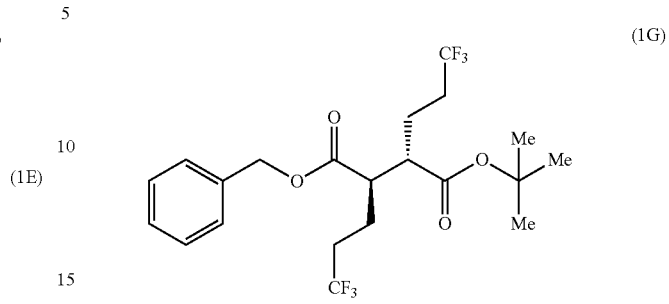

(1G)

To a stirred solution of a 9:1 enriched mixture of Preparation 1E and Preparation 1F (5.98 g, 16.33 mmol) in DMF (63 ml) was added potassium carbonate (4.06 g, 29.4 mmol) and benzyl bromide (2.9 ml, 24.38 mmol), then the reaction mixture was stirred overnight. The reaction mixture was diluted with EtOAc (1000 mL), washed with 10% LiCl (3×200 mL), brine (200 mL), then dried with Na$_2$SO$_4$, filtered and concentrated under vacuum. The residue was purified by SiO$_2$ chromatography using a toluene:hexane gradient. Obtained diastereomerically pure Preparation 1G (4.81 g, 65%) as a colorless solid: $^1$H NMR (400 MHz, chloroform-d) δ 7.32-7.43 (m, 5H), 5.19 (d, J=12.10 Hz, 1H), 5.15 (d, J=12.10 Hz, 1H), 2.71 (dt, J=3.52, 9.20 Hz, 1H), 2.61 (dt, J=3.63, 9.63 Hz, 1H), 1.96-2.21 (m, 4H), 1.69-1.96 (m, 3H), 1.56-1.67 (m, 1H), 1.45 (s, 9H).

Preparation 1E: (2R,3S)-3-(tert-Butoxycarbonyl)-6,6,6-trifluoro-2-(3,3,3-trifluoropropyl)hexanoic acid

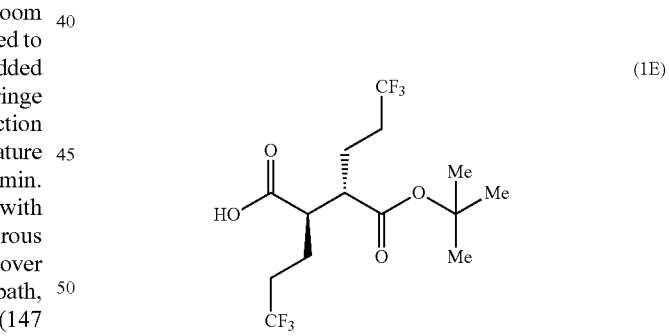

(1E)

To a solution of Preparation 1G (4.81 g, 10.54 mmol) in MeOH (100 mL) was added 10% palladium on carbon (wet, Degussa type, 568.0 mg, 0.534 mmol) in a H$_2$-pressure flask. The vessel was purged with N$_2$ (4×) then with H$_2$ (2×), then pressurized to 50 psi and shaken overnight. The reaction mixture was depressurized and purged, the mixture was filtered through CELITE®, washed with MeOH then concentrated and dried under vacuum. Obtained Preparation 1E (3.81 g, 99% yield)) as a colorless solid: $^1$H NMR (400 MHz, CDCl$_3$) δ 2.62-2.79 (m, 2H), 2.02-2.40 (m, 4H), 1.87-2.00 (m, 2H), 1.67-1.84 (m, 2H), 1.48 (s, 9H).

Preparation 1F: (S)-7-Amino-5H-dibenzo[b,d]azepin-6(7H)-one

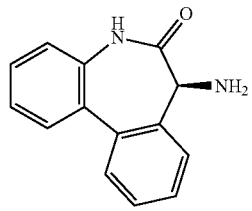

(1H)

Racemic 7-amino-5H-dibenzo[b,d]azepin-6(7H)-one was prepared according to the procedure disclosed in WO 2008/145525 A2. The enantiomers were separated by Preparative SFC chromatography (Berger SFC MGIII Column: OJ-H 5×25 cm; Mobile Phase: 15% MeOH+0.1% diethylamine in $CO_2$; Flow rate: 270 mL/min; Temperature: 35° C.; Detector wavelength: 255 nm). Concentrating the second eluting peak gave the S-enantiomer Preparation 1H as a white solid. HPLC: RT=1.428 min ($H_2O$/MeOH with TFA, CHROMOLITH® SpeedROD, 4.6×50 mm, gradient=4 min, wavelength=220 nm); MS(ES):m/z=225 [M+H$^+$]; $^1$H NMR (500 MHz, DMSO-$d_6$) δ 10.18 (br. s., 1H), 7.69 (d, J=7.8 Hz, 1H), 7.65 (dd, J=7.8, 1.4 Hz, 1H), 7.53 (dd, J=7.6, 1.2 Hz, 1H), 7.48 (td, J=7.6, 1.2 Hz, 1H), 7.46-7.38 (m, 2H), 7.29 (td, J=7.6, 1.2 Hz, 1H), 7.20 (dd, J=8.0, 1.1 Hz, 1H), 4.09 (s, 1H), 2.28 (br. s., 2H).

Preparation 1I: (2S,3R)-tert-Butyl 6,6,6-trifluoro-3-(((S)-6-oxo-6,7-dihydro-5H-dibenzo[b,d]azepin-7-yl)carbamoyl)-2-(3,3,3-trifluoropropyl)hexanoate

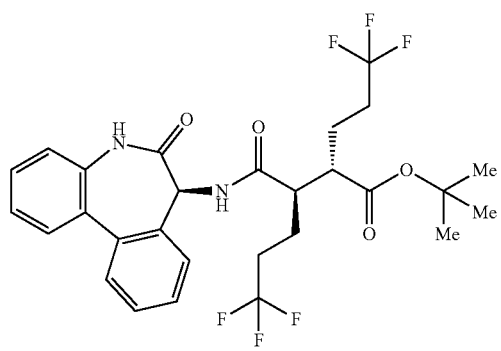

(1I)

In a 10 mL vial, a solution of Preparation 1H (50 mg, 0.223 mmol), $Et_3N$ (0.047 mL, 0.334 mmol), and Preparation 1E (82 mg, 0.223 mmol) in DMF (1 mL) was treated with O-benzotriazol-1-yl-N,N,N',N'-tetramethyluronium tetrafluoroborate (107 mg, 0.334 mmol) and stirred at room temperature for 1 hour. The reaction mixture was diluted with water and saturated aqueous $NaHCO_3$. The off-white precipitate formed was filtered and washed with water. The resulting solid was dried under vacuum to give Preparation 1I (124.8 g, 98% yield) and used without purification; HPLC: RT=3.651 min ($H_2O$/MeOH with TFA, CHROMOLITH® ODS S5 4.6× 50 mm, gradient=4 min, wavelength=220 nm).

Preparation 1J

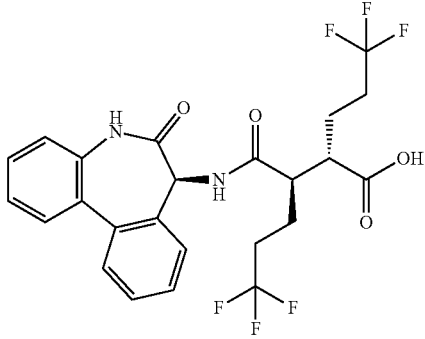

(1J)

In a 5 mL vial, a solution of Preparation 1I (124 mg, 0.217 mmol) in DCM (1.5 mL) was treated with TFA (1.5 mL) and the resulting pale orange solution was stirred at room temperature for 1.5 hours. The reaction mixture was concentrated to give Preparation 1J. This was used in the next reaction without further purification. HPLC: RT=3.016 min ($H_2O$/MeOH with TFA, CHROMOLITH® ODS S5 4.6×50 mm, gradient=4 min, wavelength=220 nm).

Example 1

To a solution of Preparation 1J (112 mg, 5.86 mmol) in THF (2 mL) in a 5 mL vial was added HOBT (66.4 mg, 0.434 mmol) and EDC (83 mg, 0.434 mmol), and then treated with ammonia (2M in iPrOH, 0.976 mL, 1.952 mmol). The resulting white suspension was stirred at room temperature overnight. The reaction mixture was concentrated and the crude material purified on preparative HPLC (Luna C18, 30×100, 40-60% aqueous methanol over 12 minutes containing 0.1% TFA holding at 60% and additional 12 min, 30 mL/min, detecting and monitoring at 220 nm). The fractions containing product were concentrated and the resulting white precipitate was collected by filtration, rinsed with 10% MeOH in water and dried under vacuum to give Example 1 (18.7 mg, 15.9% yield). HPLC: RT=8.859 min ($H_2O$/$CH_3CN$ with TFA, SunFire C18 3.5 μm, 4.6×150 mm, gradient=15 min, wavelength=220 and 254 nm); MS(ES):m/z=516 [M+H$^+$]; $^1$H NMR (500 MHz, DMSO-$d_6$) δ 10.39 (s, 1H), 9.25 (d, J=8.6 Hz, 1H), 7.72 (dd, J=7.8, 1.1 Hz, 1H), 7.62 (d, J=7.8 Hz, 2H), 7.55-7.41 (m, 4H), 7.39-7.33 (m, 1H), 7.26 (d, J=8.0 Hz, 1H), 7.12 (br. s., 1H), 5.26 (d, J=8.6 Hz, 1H), 2.94 (dt, J=10.2, 7.2 Hz, 1H), 2.47 (br. s., 1H), 2.35-2.02 (m, 4H), 1.79-1.67 (m, 1H), 1.65-1.56 (m, 2H), 1.50-1.39 (m, 1H).

Example 2

(2R,3S)-N-((7S)-6-Oxo-6,7-dihydro-5H-dibenzo[b,d]azepin-7-yl)-3-propyl-2-(3,3,3-trifluoropropyl)succinamide

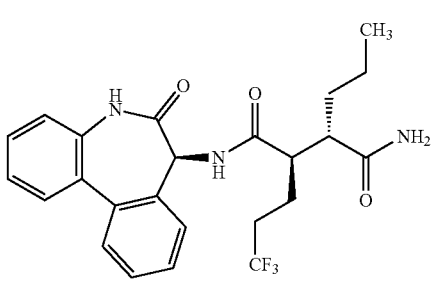
(2)

Preparation 2A: (2R,3S)-3-(tert-Butoxycarbonyl)-2-(3,3,3-trifluoropropyl)hexanoic acid

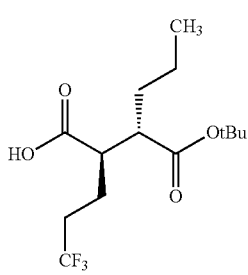
(2A)

Preparation 3N (0.8 g, 1.998 mmol) was dissolved in MeOH (15.37 ml). Palladium on carbon (Degussa, 10%) (0.053 g, 0.050 mmol) was added, then the atmosphere was exchanged with H₂ three times. The reaction mixture was stirred for ca. 6 hours, then filtered with EtOAc rinses. The filtrate was concentrated to give Preparation 2A (627 mg, 100%): $^1$H NMR (400 MHz, CDCl$_3$) δ 2.72-2.65 (m, 1H), 2.64-2.56 (m, 1H), 2.34-2.04 (m, 2H), 1.98-1.86 (m, 1H), 1.82-1.59 (m, 2H), 1.47 (s, 9H), 1.44-1.23 (m, 3H), 0.99-0.86 (m, 3H).

Example 2

Example 2 was prepared from Preparation 1H and Preparation 2A using the general procedure given for Example 1. Example 2: HPLC: RT=1.46 min (Waters Acquity UPLC BEH C18, 2.1×50 mm, 1.7-μm particles; Mobile Phase: A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.11 mL/min); MS(ES):m/z=462 [M+H⁺]; $^1$H NMR (500 MHz, 1:1 CDCl$_3$: methanol-d$_4$) δ 7.74-7.65 (m, 1H), 7.52-7.46 (m, 1H), 7.46-7.40 (m, 3H), 7.36-7.30 (m, 1H), 7.22 (d, J=7.9 Hz, 1H), 5.43 (s, 1H), 4.29 (s, 3H), 3.49-3.39 (m, 1H), 2.75 (td, J=10.0, 5.2 Hz, 1H), 2.43 (td, J=10.8, 2.7 Hz, 1H), 2.24-2.06 (m, 2H), 1.99-1.91 (m, 2H), 1.81-1.67 (m, 2H), 1.67-1.57 (m, 1H), 1.34 (dd, J=7.2, 3.7 Hz, 2H), 1.28-1.12 (m, 1H), 0.85 (t, J=6.9 Hz, 2H).

Example 3

(2R,3S)-3-(Cyclopropylmethyl)-N-((7S)-6-oxo-6,7-dihydro-5H-dibenzo[b,d]azepin-7-yl)-2-(3,3,3-trifluoropropyl)succinamide

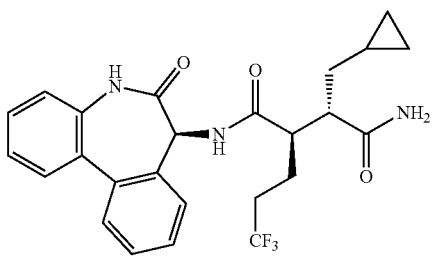
(3)

Preparation 3A: (4S)-4-(Propan-2-yl)-3-(5,5,5-trifluoropentanoyl)-1,3-oxazolidin-2-one

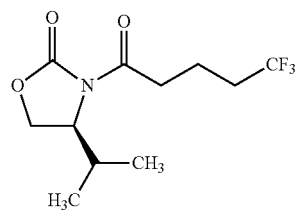
(3A)

To a stirred solution of 5,5,5-trifluoropentanoic acid (5.04 g, 32.3 mmol) in DCM (50 mL) and DMF (3 drops) was added oxalyl chloride (3.4 mL, 38.8 mmol) dropwise over 5 min. The solution was stirred until all bubbling subsided. The reaction mixture was concentrated under reduced pressure to give a pale yellow oil. To a separate flask charged with a solution of (4S)-4-(propan-2-yl)-1,3-oxazolidin-2-one (4.18 g, 32.4 mmol) in THF (100 mL) at −78° C. was added n-BuLi (13.0 mL, 32.5 mmol, 2.5M in hexane) dropwise via syringe over 5 min. After stirring for 10 min, the above acid chloride dissolved in THF (20 mL) was added via cannula over 15 min. The reaction mixture was warmed to 0° C., and was allowed to warm to room temperature as the bath warmed and stirred overnight. To the reaction mixture was added saturated NH$_4$Cl, and then extracted with EtOAc (2×). The combined organics were washed with brine, dried (Na$_2$SO$_4$), filtered and concentrated under reduced pressure. The crude material was purified by silica gel chromatography (hexanes/EtOAc) to provide Preparation 3A (7.39 g, 86%) as a colorless oil: $^1$H NMR (400 MHz, CDCl$_3$) δ 4.44 (1H, dt, J=8.31, 3.53 Hz), 4.30 (1H, t, J=8.69 Hz), 4.23 (1H, dd, J=9.06, 3.02 Hz), 2.98-3.08 (2H, m), 2.32-2.44 (1H, m, J=13.91, 7.02, 7.02, 4.03 Hz), 2.13-2.25 (2H, m), 1.88-2.00 (2H, m), 0.93 (3H, d, J=7.05 Hz), 0.88 (3H, d, J=6.80 Hz).

Preparation 3B: tert-Butyl 3-cyclopropylpropanoate

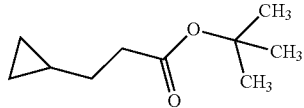

To a cool (0° C., precooled for at least 15 min), stirred solution of 3-cyclopropylpropanoic acid (5 g, 43.8 mmol) in hexane (30.0 mL) and THF (30 mL) under $N_2$ was added tert-butyl 2,2,2-trichloroacetimidate (15.7 mL, 88 mmol) portionwise over 5 min. The reaction mixture was stirred for 15 min. Boron trifluoride ether complex (0.555 mL, 4.38 mmol) was added and the reaction mixture was allowed to warm to room temperature as the bath warmed overnight. To the clear reaction mixture was added $NaHCO_3$ (5 g) and stirred for 60 min. The suspension was filtered through $MgSO_4$ and washed with 300 mL hexane. The filtrate was allowed to sit, then the formed solid was filtered through the same $MgSO_4$ filter, washed with hexane (100 mL). The filtrate was concentrated under vacuo with the water bath not turned on. The residue was purified by silica gel chromatography (hexanes/EtOAc) to provide Preparation 3B (6.05 g, 81%) as clear oil: $^1$H NMR (400 MHz, $CDCl_3$) δ 2.29 (2H, t, J=7.48 Hz), 1.35-1.54 (11H, m), 0.60-0.75 (1H, m), 0.29-0.46 (2H, m), −0.06-0.10 (2H, m).

Preparation 3C: (2S,3R)-tert-Butyl 2-(cyclopropylmethyl)-6,6,6-trifluoro-3-((S)-4-isopropyl-2-oxooxazolidine-3-carbonyl)hexanoate, and

Preparation 3D: (2R,3R)-tert-Butyl 2-(cyclopropylmethyl)-6,6,6-trifluoro-3-((S)-4-isopropyl-2-oxooxazolidine-3-carbonyl)hexanoate

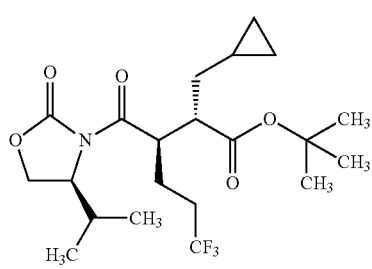

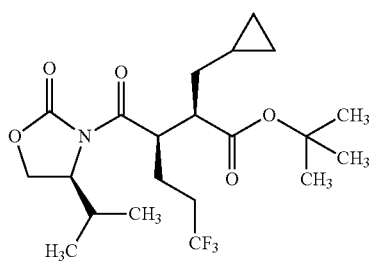

Diisopropylamine (6.64 ml, 46.6 mmol) was dissolved in 71.7 mL of THF and cooled to −78° C., then n-BuLi (18.0 mL, 44.9 mmol, 2.5M in hexane) was added dropwise over a period of 5 minutes. After 5 minutes, the resulting 0.5 M LDA solution was kept at 0° C.

In a separate flask, lithium chloride (2.62 g, 61.7 mmol) was dried under high vacuum with heating and cooled under nitrogen. Preparation 3A (3.0 g, 11.23 mmol), azeotroped once with toluene, was transferred with 15.0 mL toluene to the flask containing LiCl, and cooled to −78° C. To this stirring suspension was added LDA (25.83 mL, 12.91 mmol, 1.15 equiv., 0.5M LDA) dropwise via syringe over 5 min. The reaction mixture was stirred at −78° C. for 15 minutes, then at 0° C. for 10 minutes and cooled to −78° C.

In a separate flask, Preparation 3B (3.44 g, 20.21 mmol) was dissolved in 15.0 mL toluene under $N_2$ and cooled to −78° C. To this solution was added LDA (46.48 mL, 23.24 mmol, 1.15 equiv., 0.5M LDA) dropwise and stirred at −78° C. for 30 minutes, at which time this solution was added via cannula (fast negative pressure, all added within 30 seconds) to the LiCl/oxazolidone solution at −78° C. After 1 minute following transfer, solid bis(2-ethylhexanoyloxy)copper (10.80 g, 30.9 mmol) was added at −78° C., and the flask was transferred to 40° C. water bath and swirled vigorously for 15 minutes, and quenched over 5% $NH_4OH$ solution (20 mL saturated $NH_4OH$ and 100 mL water), and extracted with ethyl acetate (2×100 mL). The pooled organic phases were washed with brine, dried ($Na_2SO_4$), filtered, concentrated and purified by silica gel chromatography (hexanes/EtOAc) to afford a mixture of Preparation 3C and Preparation 3D (1.58 g, 32% yield) as an oil: $^1$H NMR showed this material to be a 1.5:1 mixture of Preparation 3C: Preparation 3D, by integration of the t-Bu peaks: $^1$H NMR of diastereoisomer mixture (400 MHz, $CDCl_3$) δ 4.53-4.41 (m, 2H), 4.39-4.19 (m, 5H), 4.10-4.01 (m, 1H), 2.89-2.77 (m, 2H), 2.47-2.26 (m, 2H), 2.16-1.72 (m, 8H), 1.47 (s, 9H, t-Bu of Preparation 3C, integrates for relative intensity of 1.5), 1.46 (s, 9H, t-Bu of Preparation 3D, integrates for relative intensity of 1), 0.98-0.86 (m, 16H), 0.78-0.64 (m, 2H), 0.56-0.37 (m, 4H), 0.14-0.01 (m, 4H).

Preparation 3E: (R)-2-((S)-1-tert-Butoxy-3-cyclopropyl-1-oxopropan-2-yl)-5,5,5-trifluoropentanoic acid, and

Preparation 3F: (R)-2-((R)-1-tert-Butoxy-3-cyclopropyl-1-oxopropan-2-yl)-5,5,5-trifluoropentanoic acid

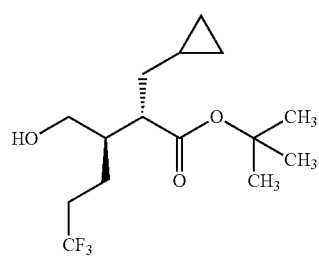

-continued (3F)

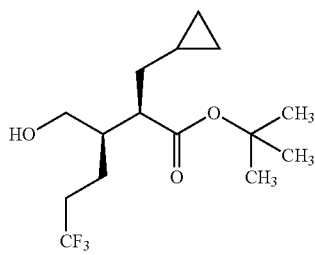

To a cool (0° C.), stirred solution of a mixture of Preparations 3C and 3D (3.4 g, 7.81 mmol) in THF (60 mL) and water (20 mL) was added 30% H$_2$O$_2$ (4.82 mL, 79 mmol) followed by LiOH (0.567 g, 23.66 mmol). The reaction mixture was allowed to gradually warm up to room temperature and stirred at room temperature for 3 h. To the reaction mixture was added saturated Na$_2$SO$_3$ (20 mL) and saturated NaHCO$_3$ (40 mL), and then stirred for 5 min. The reaction mixture was partially concentrated and extracted with DCM (80 mL). The aqueous phase was acidified to pH ~2, saturated with NaCl, extracted with EtOAc (2×). The combined extracts were dried (MgSO$_4$), filtered and concentrated to provide a mixture of Preparation 3E and Preparation 3F (2.01 g, 79%): $^1$H NMR showed this material to be a 1.4:1 mixture of Preparation 3E:Preparation 3F, by integration of the t-Bu peaks: $^1$H NMR of mixture of diastereomers (400 MHz, CDCl$_3$) δ 2.82-2.59 (m, 4H), 2.31-2.03 (m, 4H), 1.95-1.52 (m, 7H), 1.44 (s, 9H, t-Bu of Preparation 3F, integrates for relative intensity of 1.4), 1.42 (s, 9H, t-Bu of Preparation 3F, integrates for relative intensity of 1), 0.93 (d, J=6.6 Hz, 1H), 0.88 (d, J=6.8 Hz, 1H), 0.74-0.57 (m, 2H), 0.43 (t, J=6.8 Hz, 3H), 0.11--0.04 (m, 3H).

Preparation 3E: (R)-2-((S)-1-tert-Butoxy-3-cyclopropyl-1-oxopropan-2-yl)-5,5,5-trifluoropentanoic acid, and Preparation 3F: (R)-2-((R)-1-tert-Butoxy-3-cyclopropyl-1-oxopropan-2-yl)-5,5,5-trifluoropentanoic acid, an enriched mixture (3E)

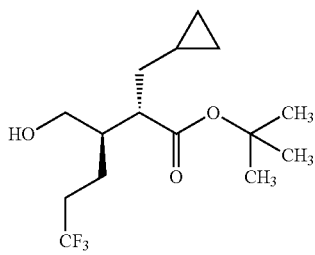

(3F)

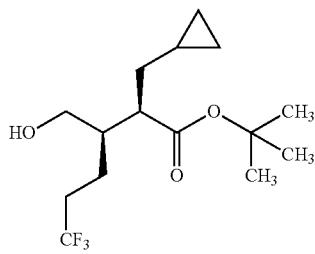

To a cold (−78° C.), stirred solution of a 1.4:1 mixture of Preparation 3E and Preparation 3F (2.00 g, 6.17 mmol) in THF (30 mL) under N$_2$ was added LDA (7.54 mL, 13.57 mmol, 1.8M) via syringe over 5 min, stirred for 15 min, warmed to room temperature (24° C. water bath), stirred for 15 min, cooled to −78° C. for 15 min. To the reaction mixture was added diethylaluminum chloride (12.95 mL, 12.95 mmol, 1M in hexane) via syringe. The reaction was stirred for 10 min, warmed to room temperature (24° C. bath) for 15 min, then cooled back to −78° C. for 25 min. MeOH (38.9 mL, 962 mmol) was rapidly added, the reaction was removed from the cooling bath, then ice and 1N HCl (55.5 mL, 55.5 mmol) were added slowly. Once gas evolution subsided, the mixture was extracted with EtOAc (2×), the combined organics washed with a solution of potassium fluoride (3.26 g, 56.2 mmol) in water (106 mL, 5895 mmol) and 1N HCl (15.72 mL, 15.72 mmol), brine then dried (Na$_2$SO$_4$). The mixture was subsequently filtered and concentrated to afford a ~2:1 (3E:3F, as determined by integration of the t-Bu peaks in the $^1$H NMR) enriched mixture of Preparation 3E and Preparation 3F (1.79 g, 90%): $^1$H NMR of mixture of diastereomers (400 MHz, CDCl$_3$) δ 2.87-2.57 (m, 2H), 2.36-2.06 (m, 2H), 1.97-1.81 (m, 2H), 1.81-1.70 (m, 1H), 1.70-1.56 (m, 1H), 1.47 (s, 9H, t-Bu of 3E, integrates for relative intensity of 2.0), 1.45 (s, 9H, t-Bu of 3F, integrates for relative intensity of 1), 0.99-0.87 (m, 1H), 0.77-0.61 (m, 1H), 0.54-0.38 (m, 2H), 0.16--0.01 (m, 2H).

Preparation 3G: (2R,3S)-1-Benzyl 4-tert-butyl 3-(cyclopropylmethyl)-2-(3,3,3-trifluoropropyl)succinate, and Preparation 3H: (2R,3R)-1-Benzyl 4-tert-butyl 3-(cyclopropylmethyl)-2-(3,3,3-trifluoropropyl)succinate (3G)

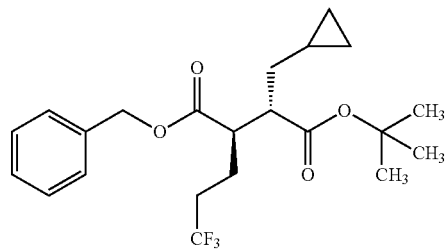

(3H)

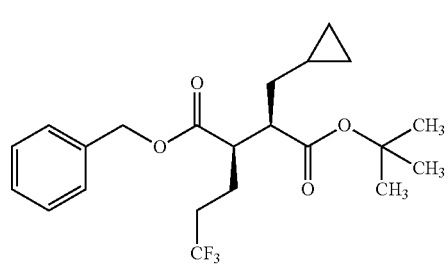

To a stirred solution of a 2.15:1 mixture of Preparation 3E and Preparation 3F (2.22 g, 6.84 mmol) and benzyl bromide (0.98 ml, 8.24 mmol) in DMF (25 ml) was added potassium carbonate (1.41 g, 10.20 mmol). The reaction mixture was then stirred for 5.5 h. The reaction mixture was diluted with EtOAc (300 mL), washed with 10% LiCl (3×100 mL), saturated NaCl, then dried (Na$_2$SO$_4$), filtered and concentrated. The residue was purified by silica gel chromatography (hexane:toluene) to give Preparation 3G (1.5 g, 53%) and Preparation 3H (0.778 g, 27%): Preparation 3G: $^1$H NMR (400 MHz, CDCl$_3$) δ 7.43-7.31 (m, 29H), 5.17 (d, J=11.9 Hz, 6H), 5.13 (d, J=11.9 Hz, 6H), 2.75-2.64 (m, 11H), 2.19-1.94 (m, 12H), 1.93-1.81 (m, 6H), 1.79-1.69 (m, 6H), 1.63-1.56 (m, 4H), 1.46 (s, 47H), 1.14 (ddd, J=13.8, 7.2, 3.5 Hz, 6H), 0.68-0.55 (m, 6H), 0.45-0.37 (m, 11H), −0.02--0.11 (m, 6H). Preparation 3H: $^1$H NMR (400 MHz, CDCl$_3$) δ 7.40-7.32 (m, 5H), 5.16 (d, J=12.3 Hz, 1H), 5.13 (d, J=12.1 Hz, 1H), 2.88-2.79 (m, 1H), 2.74 (ddd, J=8.8, 7.3, 4.4 Hz, 1H), 2.18-1.93 (m, 2H), 1.90-1.79 (m, 2H), 1.70-1.59 (m, 1H), 1.44 (s, 9H), 1.31 (ddd, J=14.1, 7.3, 4.5 Hz, 1H), 0.73-0.61 (m, 1H), 0.49-0.38 (m, 2H), 0.10-0.03 (m, 1H), −0.01--0.07 (m, 1H).

Preparation 3E: (R)-2-((S)-1-tert-Butoxy-3-cyclopropyl-1-oxopropan-2-yl)-5,5,5-trifluoropentanoic acid

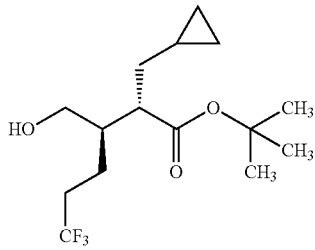

(3E)

Preparation 3G (2.80 g, 6.76 mmol) was dissolved in ethyl acetate (26.0 mL) and methanol (26.0 mL). Palladium on carbon (10% wet Degussa, 0.539 g, 0.507 mmol) was added, then the atmosphere was exchanged for H$_2$ three times. The reaction mixture was stirred about 2 h, then filtered with MeOH washes. The filtrate was concentrated to give Preparation 3E (2.19 g, 100% yield): $^1$H NMR (400 MHz, CDCl$_3$) δ 2.79-2.67 (m, 2H), 2.36-2.21 (m, 1H), 2.18-2.03 (m, 1H), 1.94 (dtd, J=14.6, 9.8, 4.8 Hz, 1H), 1.78 (ddd, J=11.1, 5.3, 3.0 Hz, 1H), 1.63 (ddd, J=13.9, 9.2, 7.0 Hz, 1H), 1.49 (s, 9H), 1.35 (ddd, J=13.8, 7.0, 3.9 Hz, 1H), 0.77-0.63 (m, 1H), 0.48 (dq, J=8.1, 1.7 Hz, 2H), 0.15-0.02 (m, 2H).

An alternate method to prepare Preparation 3G, and hence Preparation 3E:

Preparation 3I: (S)-4-Benzyl-3-(5,5,5-trifluoropentanoyl)oxazolidin-2-one

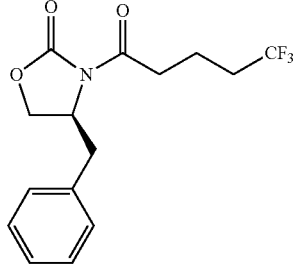

(3I)

To a stirring solution of 5,5,5-trifluoropentanoic acid (71.4 g, 457 mmol) in DCM (315 mL) and 5 drops of DMF was added oxalyl chloride (229 mL, 457 mmol). The reaction mixture was then stirred until gas evolution subsided. The reaction mixture was concentrated, and the material was used below.

A separate flask was charged with (S)-4-benzyloxazolidin-2-one (60 g, 339 mmol) and THF (315 mL), cooled to −78° C., followed by the dropwise addition of n-butyl lithium (183 mL, 2.5M, 457 mmol). A heavy suspension resulted during addition, therefore additional THF (315 mL) was added. Once the addition of BuLi was ended, to the reaction mixture was added a solution of the above acid chloride in THF (150 mL) dropwise, stir for 10 minutes at −78° C., then allowed to warm to room temperature. The reaction was quenched with aqueous saturated NH$_4$Cl solution at 0-5° C. The reaction mixture was extracted with EtOAc, washed with water, brine, dried (Na$_2$SO$_4$), filtered and concentrated. The residue was purified by silica gel chromatography (hexane/EtOAc) to provide Preparation 3I (87 g, 81%): $^1$H NMR (400 MHz, CDCl$_3$) δ 7.32-7.39 (2H, m), 7.30 (1H, d, J=7.05 Hz), 7.18-7.25 (2H, m), 4.64-4.74 (1H, m), 4.17-4.27 (2H, m), 3.31 (1H, dd, J=13.35, 3.27 Hz), 3.00-3.11 (2H, m), 2.79 (1H, dd, J=13.35, 9.57 Hz), 2.16-2.28 (2H, m), 1.93-2.04 (2H, m).

Preparation 3J: tert-Butyl (3R)-3-(((4S)-4-benzyl-2-oxo-1,3-oxazolidin-3-yl) carbonyl)-6,6,6-trifluorohexanoate

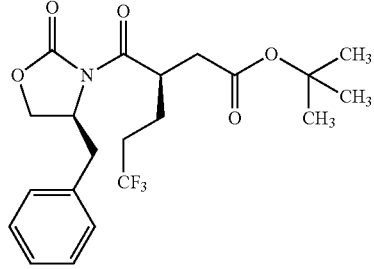

(3J)

To a cold (−78° C.), stirred solution of Preparation 3I (43 g, 136 mmol) in THF (150 mL) was added NaHMDS (150 mL, 1.0M in THF, 150 mmol) under nitrogen atmosphere. After 2 hours, tert-butyl 2-bromoacetate (53.2 g, 273 mmol) in THF (100 mL) was added at −78° C. and stirring was maintained at the same temperature. After 6 hours, the reaction mixture was warmed to room temperature. The reaction mixture was partitioned between saturated NH$_4$Cl and EtOAc. The organic phase was separated, and the aqueous phase was extracted with EtOAc (3×). The combined organics were washed with brine, dried (Na$_2$SO$_4$), filtered and concentrated under reduced pressure. The residue was purified by silica gel chromatography (hexane/EtOAc) to provide Preparation 3J (37 g, 63%): $^1$H NMR (400 MHz, CDCl$_3$) δ 7.34 (2H, d, J=7.30 Hz), 7.24-7.32 (3H, m), 4.62-4.75 (1H, m, J=10.17, 6.89, 3.43, 3.43 Hz), 4.15-4.25 (3H, m), 3.35 (1H, dd, J=13.60, 3.27 Hz), 2.84 (1H, dd, J=16.62, 9.57 Hz), 2.75 (1H, dd, J=13.35, 10.07 Hz), 2.47 (1H, dd, J=16.62, 4.78 Hz), 2.11-2.23 (2H, m), 1.90-2.02 (1H, m), 1.72-1.84 (1H, m), 1.44 (9H, s).

Preparation 3K: (2R)-2-(2-tert-Butoxy-2-oxoethyl)-5,5,5-trifluoropentanoic acid

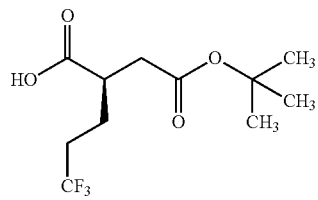
(3K)

To a cool (0° C.), stirred solution of Preparation 3J (26 g, 60.5 mmol) in THF (390 mL) and water (104 mL) was added H$_2$O$_2$ (24.1 mL, 236 mmol) followed by LiOH (2.75 g, 115 mmol) as a solution in water (28 mL). The reaction mixture was allowed to gradually warm to room temperature and stirred at room temperature for 3 h. The reaction mixture was cooled to 0° C., then saturated Na$_2$SO$_3$ and saturated NaHCO$_3$ were added. The reaction mixture was stirred for 5 min, and then partially concentrated and extracted with DCM (20 ml). The aqueous phase was acidified to pH~3, extracted with EtOAc. The extract was dried (Na$_2$SO$_4$), filtered, and concentrated to obtain Preparation 3K (15 g, 92%): $^1$H NMR (400 MHz, CDCl$_3$) δ 2.83-2.95 (1H, m), 2.62-2.74 (1H, m), 2.45 (1H, dd, J=16.62, 5.79 Hz), 2.15-2.27 (2H, m), 1.88-2.00 (1H, m), 1.75-1.88 (1H, m), 1.45 (9H, s).

Preparation 3L: (2R,3S)-3-(tert-Butoxycarbonyl)-2-(3,3,3-trifluoropropyl)hex-5-enoic acid, and Preparation 3M: (2R,3R)-3-(tert-Butoxycarbonyl)-2-(3,3,3-trifluoropropyl)hex-5-enoic acid

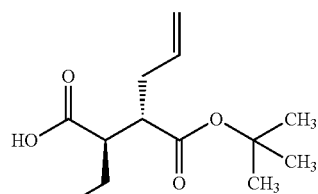
(3L)

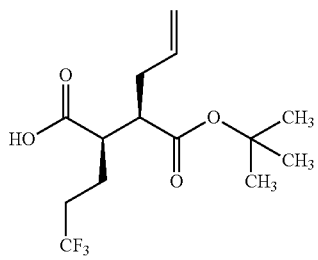
(3M)

A flask was charged with THF (150 ml), then cooled to −20° C., then with stirring n-butyllithium (53.9 ml, 2.5 M in hexane, 135 mmol) was added, followed by diisopropylamine (19.4 ml, 137 mmol) over 55 min while maintaining the internal temperature at less than −8.5° C. After addition was complete, the solution was stirred at 0° C. for 45 min, and then cooled to −78° C. To this was added a solution of Preparation 3K (14.56 g, 53.9 mmol) in THF (15.0 ml) over 20 min, while maintaining internal temperature at less than −72° C. After addition was complete, the mixture was stirred at −78° C. for 100 min. To this was added 3-bromoprop-1-ene (6.38 ml, 75 mmol) over 10 min. The reaction mixture was stirred allowed to slowly warm to room temperature as bath warmed, and stirred overnight. To the solution was added ice, quenched with 1N HCl (215 mL) to pH about 1, saturated with NaCl. The layers were separated. The aqueous layer was extracted with EtOAc (1×250 mL, 1×150 mL). The combined organic phases were washed with brine (1×300 mL), dried (MgSO$_4$), filtered, and evaporated. The residue was treated with benzene (50 mL) and evaporated twice, dried in vacuo to give a mixture of Preparation 3L and Preparation 3M (16.8 g, 100%): $^1$H NMR indicated a ratio 1:2 for Preparation 3L:Preparation 3M: $^1$H NMR of diastereoisomer mixture (400 MHz, CDCl$_3$) δ 5.81-5.66 (m, 1H), 5.17-5.04 (m, 2H), 2.81-2.62 (m, 2H), 2.45-2.38 (m, 2H), 2.33-2.03 (m, 3H), 1.96-1.83 (m, 2H), 1.45 (s, 9H, t-Bu of Preparation 3L, integrates for relative intensity of 1), 1.44 (s, 9H, t-Bu of Preparation 3M, integrates for relative intensity of 2).

Preparation 3L: (2R,3S)-3-(tert-Butoxycarbonyl)-2-(3,3,3-trifluoropropyl)hex-5-enoic acid, and Preparation 3M: (2R,3R)-3-(tert-Butoxycarbonyl)-2-(3,3,3-trifluoropropyl)hex-5-enoic acid, an enriched mixture

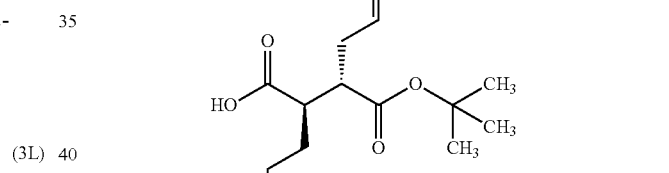
(3L)

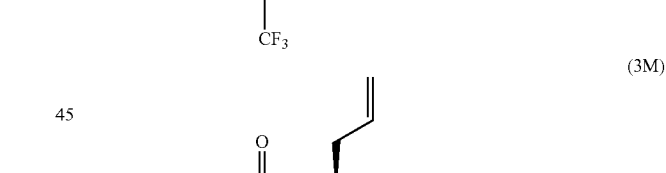
(3M)

To a cold (−78° C.) stirred solution of a mixture of Preparation 3L and Preparation 3M (10 g, 32.2 mmol) in THF (150 mL) was slowly added LDA (39.4 mL, 70.9 mmol, 1.8M in heptane/THF/ethylbenzene). After stirring for 15 min the reaction mixture was placed in a room temperature water bath. After 15 min the reaction mixture was placed back in a −78° C. bath, stirred for 15 min then diethylaluminum chloride (81 mL, 81 mmol, 1M in hexane) was added via addition funnel. The reaction mixture was stirred at −78° C. After 10 min the reaction mixture was placed in a room temperature water bath for 15 min and then cooled back to −78° C. for 15 min. Meanwhile, a separate flask was charged MeOH (300 mL) and cooled to −78° C. The reaction mixture was then transferred to the cold and rapidly stirring MeOH via cannula by nitrogen pressure. After the transfer was complete ice (86 g) was added to the reaction mixture followed by slow addition of 1N HCl (300 mL). The reaction mixture was stirred until all gas evolution subsided. EtOAc (400 mL) was added, the phases separated, and the aqueous phase was extracted with EtOAc (300 mL). The combined EtOAc layers were washed with a mixture of potassium fluoride (17 g) in 600 mL H$_2$O and 1N HCl (86 mL), followed by brine. The organic phase was dried (Na$_2$SO$_4$), filtered and concentrated under reduced pressure to provide a 7:1 (3L:3M) enriched mixture of Preparation 3L and Preparation 3 M (10.0 g, 100%): $^1$H NMR of diastereoisomer mixture (400 MHz, CDCl$_3$) δ 5.81-5.66 (m, 1H), 5.17-5.04 (m, 2H), 2.81-2.62 (m, 2H), 2.45-2.38 (m, 2H), 2.33-2.03 (m, 3H), 1.96-1.83 (m, 2H), 1.45 (s, 9H, t-Bu of 3L, integrates for relative intensity of 7), 1.44 (s, 9H, t-Bu of 3M, integrates for relative intensity of 1).

Preparation 3N: (2S,3R)-4-Benzyl 1-tert-butyl 2-allyl-3-(3,3,3-trifluoropropyl)succinate

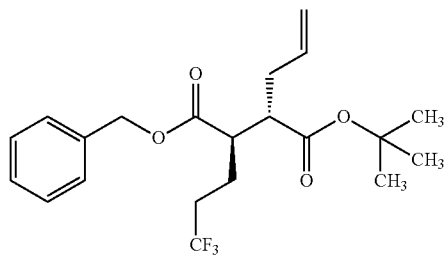

(3N)

To a stirred solution of a 7:1 enriched mixture of Preparation 3L and Preparation 3M (10 g, 32.2 mmol) in DMF (100 ml) was added benzyl bromide (4.6 ml, 38.7 mmol) and potassium carbonate (6.68 g, 48.3 mmol). The reaction mixture was stirred for two hours at room temperature. To the reaction mixture was added Et$_3$N (9.0 mL. 64.5 mmol), followed by stirring for 60 min. The reaction mixture was diluted with Et$_2$O, washed with 10% LiCl (3×100 mL), brine (100 mL), and then dried (Na$_2$SO$_4$), filtered and concentrated. The residue was purified by silica gel chromatography (hexane/toluene) to provide Preparation 3N (8.7 g, 67%): $^1$H NMR (400 MHz, CDCl$_3$) δ 7.40-7.31 (m, 5H), 5.70 (ddt, J=16.9, 10.2, 7.1 Hz, 1H), 5.19-5.11 (m, 2H), 5.09-5.02 (m, 2H), 2.83-2.68 (m, 2H), 2.43-2.32 (m, 2H), 2.19-1.94 (m, 2H), 1.91-1.81 (m, 2H), 1.42 (s, 9H).

Preparation 3G: (2R,3S)-1-Benzyl 4-tert-butyl 3-(cyclopropylmethyl)-2-(3,3,3-trifluoropropyl)succinate

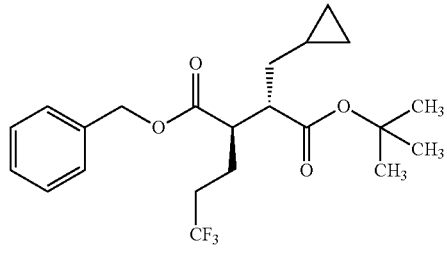

(3G)

To a mixture of 40% KOH [KOH (6 g, 107 mmol) in water (9 mL)] and Et$_2$O (60 mL) cooled to 0° C. was added 1-methyl-3-nitro-1-nitrosoguanidine (1.5 g, 10.20 mmol) portionwise. The obtained solution was swirled several times. The ether layer (yellow solution) was pipetted to a mixture of Preparation 3N (450 mg, 1.124 mmol) and Pd(OAc)$_2$ (25 mg, 0.11 mmol) in Et$_2$O (18 mL) at 0° C. The mixture was stirred at 0° C. for 3 h, and then the reaction was quenched with several drops of acetic acid. The resulting mixture was washed with saturated NaHCO$_3$ and brine, dried over MgSO$_4$, filtered and concentrated. The crude material was purified by silica gel chromatography (hexane/EtOAc) to give Preparation 3G (377 mg, 81%) as a colorless oil: HPLC: RT=3.790 min (H$_2$O/MeOH with TFA, CHROMOLITH® SpeedROD, 4.6×50 mm, gradient=4 min, wavelength=220 nm); MS(ES):m/z=415 [M+H$^+$]; $^1$H NMR (400 MHz, CDCl$_3$) δ 7.43-7.31 (m, 5H), 5.21-5.07 (m, 2H), 2.76-2.62 (m, 2H), 2.18-1.66 (m, 4H), 1.58-1.54 (m, 1H), 1.46 (s, 9H), 1.14 (ddd, J=13.8, 7.1, 3.5 Hz, 1H), 0.71-0.53 (m, 1H), 0.47-0.34 (m, 2H), 0.05--0.10 (m, 2H).

Example 3

Example 3 was prepared from Preparation 1H and Preparation 3E using the general procedure given for Example 1. Example 3: HPLC: RT=1.47 min (Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.11 mL/min); MS(ES):m/z=474 [M+H$^+$]; $^1$H NMR (500 MHz, DMSO-d$_6$) δ 10.40 (s, 1H), 9.14 (d, J=8.4 Hz, 1H), 7.71 (d, J=6.4 Hz, 1H), 7.63-7.59 (m, 2H), 7.56-7.45 (m, 4H), 7.38-7.33 (m, 1H), 7.25 (d, J=7.4 Hz, 1H), 6.99 (br. s, 1H), 5.24-5.21 (m, 1H), 2.87-2.79 (m, 1H), 2.45 (td, J=10.9, 3.0 Hz, 1H), 2.40-2.29 (m, 1H), 2.26-2.14 (m, 1H), 1.64-1.54 (m, 3H), 0.86 (ddd, J=13.5, 7.6, 3.2 Hz, 1H), 0.58-0.46 (m, 1H), 0.37-0.21 (m, 2H), -0.05--0.13 (m, 1H), -0.22 (dq, J=9.1, 4.6 Hz, 1H).

Example 4

(2R,3S)-N-((7S)-6-Oxo-6,7-dihydro-5H-dibenzo[b,d]azepin-7-yl)-2-propyl-3-(3,3,3-trifluoropropyl)succinamide

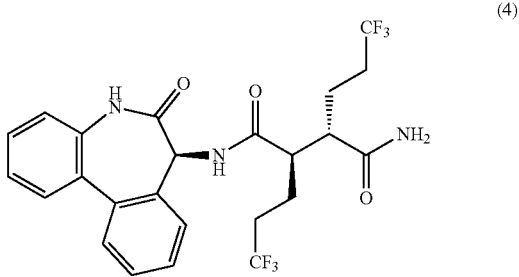

(4)

Preparation 4A:
((S)-4-Isopropyl-3-pentanoyloxazolidin-2-one

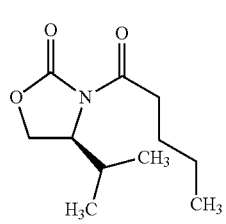

(4A)

To a stirred solution of pentanoic acid (5.98 g, 58.6 mmol) in CH$_2$Cl$_2$ (100 mL) and 10 drops DMF was added oxalyl chloride (5.64 mL, 64.4 mmol) dropwise over 5 min and the solution stirred for 2.75 h, at which time all bubbling subsided. The solution was concentrated in vacuo. In a separate flask, to a cold (−78° C.), stirred solution of (S)-4-isopropyloxazolidin-2-one (7.56 g, 58.6 mmol) in THF (280 mL) was added n-BuLi (2.5M in hexane, 23.42 mL, 58.6 mmol) dropwise via addition funnel over 20 min (temperature never exceeded −68° C.). After stirring 10 min, the above acid chloride dissolved in THF (50 mL) was added via addition funnel over 25 min. After the addition was complete, the reaction mixture was allowed to warm to room temperature as bath warmed and stirred overnight. The reaction was quenched with water and extracted with EtOAc (2×). The combined organic layers were washed with brine, dried (Na$_2$SO$_4$), filtered and concentrated to an amber oil. The residue was purified by flash chromatography (Teledyne ISCO CombiFlash Rf, 0% to 60% solvent A/B=hex/EtOAc, REDISEP® SiO$_2$ 120 g, applied as a DCM solution) to give Preparation 4A (6.51 g, 52%) as a colorless oil: $^1$H NMR (400 MHz, chloroform-d) δ ppm 4.44 (1H, ddd, J=8.16, 3.51, 3.39 Hz), 4.27 (1H, t, J=9.00 Hz), 4.21 (1H, dd, J=9.00, 3.01 Hz), 2.99 (1H, ddd, J=16.60, 8.50, 6.50 Hz), 2.86 (1H, ddd, J=16.60, 8.50, 6.78 Hz), 2.31-2.44 (1H, m), 1.56-1.72 (2H, m), 1.39 (2H, sxt, J=7.43 Hz), 0.94 (3H, t, J=7.28 Hz), 0.92 (3H, d, J=7.03 Hz), 0.88 (3H, d, J=6.78 Hz); HPLC: RT=2.497 min (CHROMOLITH® SpeedROD 4.6×50 mm (4 min grad) eluting with MeOH/H$_2$O/0.1% TFA, 4 mL/min, monitoring at 220 nm).

Preparation 4B: (2S,3R)-tert-Butyl 3-((S)-4-isopropyl-2-oxooxazolidine-3-carbonyl)-2-(3,3,3-trifluoropropyl)hexanoate, and

Preparation 4C: (2R,3R)-tert-Butyl 3-((S)-4-isopropyl-2-oxooxazolidine-3-carbonyl)-2-(3,3,3-trifluoropropyl)hexanoate

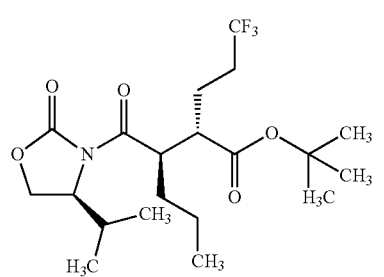

(4B)

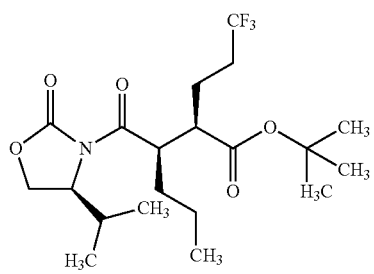

(4C)

To a cold (−78° C.), stirred solution of diisopropylamine (5.4 mL, 37.9 mmol) in THF (60 mL) under nitrogen atmosphere was added n-BuLi (2.5M in hexane, 15 mL, 37.5 mmol), then warmed to 0° C. to give a 0.5M solution of LDA. A separate vessel was charged with Preparation 4A (1.99 g, 9.33 mmol), then toluene (15.3 mL) was added. This solution was added to a flask containing dry lithium chloride (2.05 g, 48.4 mmol). To the resultant mixture, cooled to −78° C., was added LDA solution (21.5 mL, 10.75 mmol). The mixture was stirred at −78° C. for 10 min, warmed to 0° C. for 10 min, and then recooled to −78° C. To a separate reaction vessel containing tert-butyl 5,5,5-trifluoropentanoate (3.46 g, 16.30 mmol) was added toluene (15.3 mL). The solution was cooled to −78° C., and LDA (37.5 mL, 18.75 mmol) was added. The resulting solution was stirred at −78° C. for 25 min. At this time the enolate derived from the ester was transferred via cannula into the solution of the oxazolidinone enolate and stirred at −78° C. for an additional 5 min. The septum was removed, and solid powdered bis(2-ethylhexanoyloxy)copper (9.04 g, 25.8 mmol) was rapidly added to the reaction vessel, and the septum replaced. The vessel was immediately removed from the cold bath and immersed into a warm water bath (40° C.) with rapid swirling. The reaction mixture was stirred for 25 min, then poured into 5% aqueous NH$_4$OH (360 mL) and extracted with EtOAc (2×). The combined organics were washed with brine, dried (Na$_2$SO$_4$), filtered and concentrated under reduced pressure. The residue was purified by flash chromatography (Teledyne ISCO CombiFlash Rf, 0% to 60% solvent A/B=hexanes/EtOAc, REDISEP® SiO$_2$ 120 g). Concentration of appropriate fractions provided a mixture of Preparations 4B and 4C (1.92 g, 49%) as pale yellow viscous oil:

$^1$H NMR (400 MHz, CDCl$_3$) δ 4.48 (dt, J=7.8, 3.5 Hz, 1H), 4.44 (dt, J=7.7, 3.4 Hz, 1H), 4.33-4.19 (m, 3H), 4.06 (ddd, J=10.3, 7.0, 3.5 Hz, 1H), 2.83 (td, J=8.3, 4.4 Hz, 1H), 2.67 (ddd, J=10.5, 7.0, 3.9 Hz, 1H), 2.49-1.93 (m, 8H), 1.91-1.80 (m, 2H), 1.79-1.55 (m, 5H), 1.47 (s, 9H, major diastereomer), 1.44 (s, 9H, minor diastereomer), 0.98-0.85 (m, 18H).

Preparation 4D: (2R,3S)-3-(tert-Butoxycarbonyl)-6,6,6-trifluoro-2-propylhexanoic acid, and

Preparation 4E: (2R,3R)-3-(tert-Butoxycarbonyl)-6,6,6-trifluoro-2-propylhexanoic acid

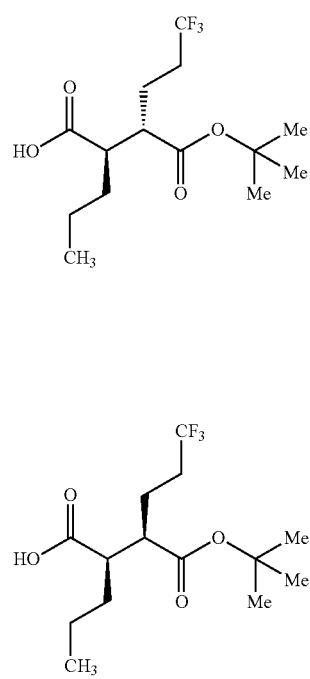

To a cool (0° C.), stirred solution of Preparation 4B and Preparation 4C (1.92 g, 4.53 mmol) in THF (67 mL) and water (20 mL) was added H$_2$O$_2$ (30% in water, 4.93 g, 43.5 mmol) followed by LiOH (329 mg, 13.7 mmol). After 60 min, the reaction mixture was warmed to room temperature. After an additional 60 min, to the reaction mixture was added ice (to control exotherm), saturated aqueous NaHCO$_3$ (15 mL) and saturated aqueous Na$_2$SO$_3$ (15 mL). The mixture was partially concentrated in vacuo and extracted with DCM (2×100 mL). The organic layers were discarded. The aqueous phase was acidified (to pH~1-2) with 1N HCl, saturated with NaCl, extracted with DCM (3×100) and EtOAc (1×100), the organic extracts were combined, dried (MgSO$_4$), filtered and concentrated. Obtained a mixture of Preparation 4D and Preparation 4E (666 mg, 47%) as a colorless oil: $^1$H NMR (400 MHz, CDCl$_3$) δ 2.78-2.54 (m, 4H), 2.29-1.99 (m, 4H), 1.97-1.79 (m, 3H), 1.78-1.49 (m, 5H), 1.47 (s, 9H, minor diastereomer), 1.45 (s, 9H, major diastereomer), 1.44-1.17 (m, 4H), 0.98-0.85 (m, 6H).

Preparation 4D: (2R,3S)-3-(tert-Butoxycarbonyl)-6,6,6-trifluoro-2-propylhexanoic acid, and

Preparation 4E: (2R,3R)-3-(tert-Butoxycarbonyl)-6,6,6-trifluoro-2-propylhexanoic acid, an enriched mixture

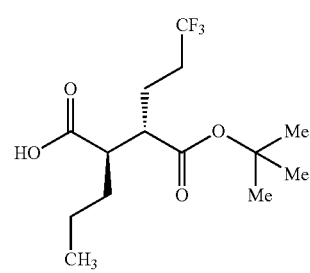

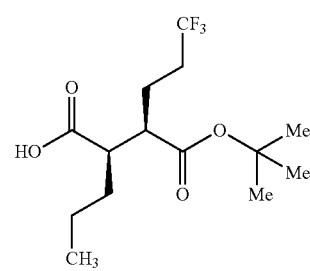

To a cold (~−78° C.), stirred solution of Preparation 4D and Preparation 4E (4.75 g, 15.21 mmol) in THF (84 mL) under N$_2$ was added LDA (1.8M, 20.3 mL, 36.5 mmol) dropwise over 10 min (internal temperature never exceeded −68° C.). The reaction mixture was stirred for 15 min, warmed to room temperature in a water bath, stirred for 15 min, and then cooled to −78° C. for 15 min. To the reaction mixture was added Et$_2$AlCl (1M in hexane, 32.0 mL, 32.0 mmol) via syringe. The reaction mixture was stirred for 10 min, warmed to room temperature in a water bath for 15 min then cooled to −78° C. for 25 min. Meanwhile, a flask containing MeOH (140 mL) was cooled to −78° C. The reaction solution was rapidly transferred to the MeOH via cannula. The flask removed from the cooling bath, then ice and 1N HCl (137 mL, 137 mmol) (CAUTION: much gas evolution/bubbling/foaming occurred) was added slowly. The reaction mixture was extracted with EtOAc (2×300 mL), the combined organics were washed successively with a solution of potassium fluoride (7.95 g, 137 mmol) in water (300 mL), 1N HCl (38 mL, 38.0 mmol), then brine. The organic layer was dried (Na$_2$SO$_4$), filtered and concentrated to a golden yellow oil. 1H NMR showed product was a 7.58:1 mixture of Preparation 4D to Preparation 4E. Obtained a mixture of Preparation 4D and Preparation 4E (4.70 g, 99%) as a dark amber viscous oil: $^1$H NMR (400 MHz, CDCl$_3$) δ 2.78-2.54 (m, 4H), 2.29-1.99 (m, 4H), 1.97-1.79 (m, 3H), 1.78-1.49 (m, 5H), 1.47 (s, 9H, minor diastereomer), 1.45 (s, 9H, major diastereomer), 1.44-1.17 (m, 4H), 0.98-0.85 (m, 6H).

Preparation 4F: (2R,3S)-1-Benzyl 4-tert-butyl 2-propyl-3-(3,3,3-trifluoropropyl)succinate

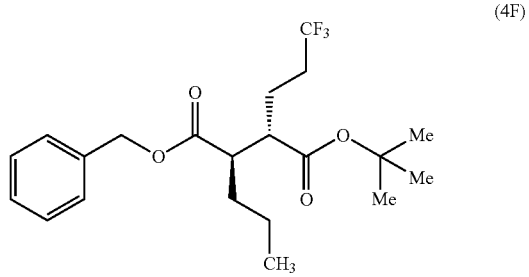 [SMILES: CCC[C@@H](C(=O)OCc1ccccc1)[C@H](CCC(F)(F)F)C(=O)OC(C)(C)C]

(4F)

To a stirred solution of Preparation 4D and Preparation 4E (4.70 g, 15.05 mmol) and benzyl bromide (2.2 mL, 18.50 mmol) in DMF (55 mL) was added potassium carbonate (3.16 g, 22.86 mmol). After 8.5 h, the reaction mixture was diluted with EtOAc (300 mL), then washed with 10% LiCl (3×100 mL) and brine. The organic layer was dried (Na$_2$SO$_4$), filtered and concentrated. The residue was purified by flash chromatography (Teledyne ISCO CombiFlash Rf, 50% to 80% solvent A/B=hexanes/toluene, REDISEP® SiO$_2$ 330 g Gold). Obtained the Preparation 4F (4.9 g, 81%): $^1$H NMR (400 MHz, CDCl$_3$) δ 7.30-7.42 (m, 5H), 5.17 (d, J=12.10 Hz, 1H), 5.13 (d, J=12.10 Hz, 1H), 2.65-2.73 (m, 1H), 2.57 (dt, J=3.52, 9.79 Hz, 1H), 1.93-2.17 (m, 2H), 1.80 (dtd, J=5.17, 10.51, 13.64 Hz, 1H), 1.58-1.73 (m, 2H), 1.45 (s, 9H), 1.16-1.43 (m, 3H), 0.85-0.91 (m, 3H).

Preparation 4D: (2R,3S)-3-(tert-Butoxycarbonyl)-6,6,6-trifluoro-2-propylhexanoic acid

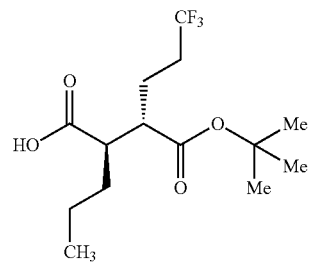

(4D)

A solution of Preparation 4F (4.9 g, 12.18 mmol) in MeOH (60 ml) was treated with activated carbon, filtered through CELITE®, and washed with MeOH (60 ml). The reaction mixture was placed under vacuum and backfilled with N$_2$ three times, then 10% palladium on carbon (wet, Degussa type, 328.1 mg, 0.308 mmol) was added. The atmosphere was exchange for N$_2$ three more times, then exchanged three times with H$_2$. After 4.5 h, the reaction mixture was purged with N$_2$ (3×), then filtered through CELITE®, washing with MeOH. The filtrate was concentrated, and dried under vacuum overnight. Obtained the Preparation 4D (3.45 g, 91%) as a colorless oil: $^1$H NMR (400 MHz, chloroform-d) δ 2.71-2.64 (m, 1H), 2.63-2.56 (m, 1H), 2.26-2.00 (m, 2H), 1.90 (dtd, J=13.7, 10.3, 5.3 Hz, 1H), 1.78-1.61 (m, 2H), 1.48 (s, 9H), 1.46-1.38 (m, 2H), 1.37-1.23 (m, 1H), 0.93 (t, J=7.0 Hz, 3H).

Example 4

Example 4 was prepared from Preparation 1H and Preparation 4D using the general method given for Example 1. Example 4: HPLC: RT=2.150 min (SUPELCO® Ascentis Express C18, 4.6×50 mm, 2.7-μm particles; Mobile Phase A: 5:95 acetonitrile:water with 10 mM ammonium acetate; Mobile Phase B: 95:5 acetonitrile:water with 10 mM ammonium acetate; Temperature: 35° C.; Gradient: 0-100% B over 4 minutes, then a 1-minute hold at 100% B; Flow: 4 mL/min); MS(ES):m/z=462 [M+H$^+$]; $^1$H NMR (500 MHz, DMSO-d$_6$) δ 10.36 (s, 1H), 9.17 (d, J=8.9 Hz, 1H), 7.72 (d, J=7.4 Hz, 1H), 7.61 (d, J=7.4 Hz, 1H), 7.55 (d, J=2.0 Hz, 1H), 7.53-7.44 (m, 3H), 7.43-7.38 (m, 1H), 7.38-7.33 (m, 1H), 7.25 (d, J=7.9 Hz, 1H), 7.02 (br. s., 1H), 5.26 (d, J=8.4 Hz, 1H), 2.84 (td, J=10.8, 3.2 Hz, 1H), 2.41-2.34 (m, 1H), 2.23-1.99 (m, 2H), 1.80-1.68 (m, 1H), 1.47-1.16 (m, 5H), 0.83 (t, J=7.2 Hz, 3H).

Example 5

(2R,3S)-3-(Cyclopropylmethyl)-N-((7S)-4-fluoro-6-oxo-6,7-dihydro-5H-dibenzo[b,d]azepin-7-yl)-2-(3,3,3-trifluoropropyl)succinamide

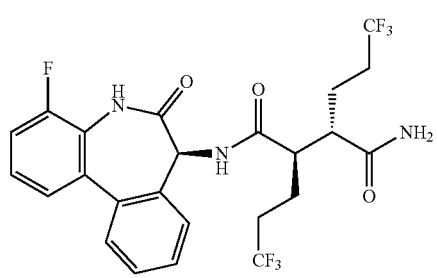

(5)

Preparation 5A: 3-Fluoro-[1,1'-biphenyl]-2-amine

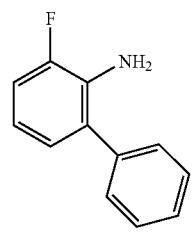

(5A)

To a solution of Na$_2$CO$_3$ (1.116 g, 10.53 mmol) in water (15 ml) was added poly(ethylene glycol) 2000 (17 g, 5.26 mmol) followed by palladium(II) acetate (0.024 g, 0.105 mmol). The suspension was heated to 50° C. Once the mixture became clear, phenylboronic acid (0.963 g, 7.89 mmol) followed by 2-bromo-6-fluoroaniline (1 g, 5.26 mmol) were added and heated at 120° C. for 30 min. The mixture was cooled, diluted with EtOAc, washed with water, dried and concentrated. The crude material was purified by ISCO (24 g REDISEP® silica column, gradient elution, 0-15% ethyl acetate in hexanes) to give Preparation 5A (800 mg, 81%): LCMS: HPLC: RT=2.016 min (MeCN/H$_2$O with HCOONH$_4$, Ascentis Express C8 2.7 μm 5×2.1 mm, gradient=4 min, wavelength=220 nm); MS(ES): m/z=188 [M+H]+; 1H NMR (CDCl3) δ 7.43-7.48 (m, 4H), 7.35-7.40 (m, 1H), 6.97-7.02 (m, 1H), 6.92 (dt, J=7.6, 1.2 Hz, 1H), 6.71-6.77 (m, 1H), 3.82 (br s, 2H).

Preparation 5B: 2-Chloro-N-(3-fluoro-[1,1'-biphenyl]-2-yl)acetamide

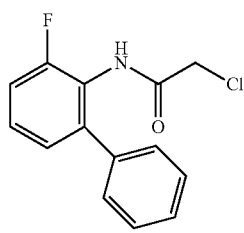

(5B)

To a solution of Preparation 5A (800 mg, 4.27 mmol) in DCM (8 mL) and Et3N (0.893 mL, 6.41 mmol) at 0° C. was added chloroacetyl chloride (0.359 mL, 4.49 mmol). The reaction mixture was stirred at room temperature for 48 hours, then the mixture was diluted with DCM and washed successively with 10% NaHCO3, water, brine. The organic layers were dried and concentrated. The crude material was purified by ISCO (24 g REDISEP® column, gradient elution, 0-25% ethyl acetate in hexanes) to give Preparation 5B (800 mg, 71%): LCMS: HPLC: RT=1.908 min (MeCN/H2O with HCOONH4, Ascentis Express C8 2.7 μm (5×2.1) mm, gradient=4 min, wavelength=220 nm); MS(ES): m/z=262 [M–H]+; 1H NMR (CDCl3) δ 7.72 (br s, 1H), 7.33-7.41 (m, 6H), 7.15-7.20 (m, 2H), 4.08 (s, 2H).

Preparation 5C: 4-Fluoro-5H-dibenzo[b,d]azepin-6(7H)-one

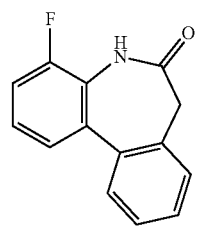

(5C)

A solution of Preparation 5B (700 mg, 2.65 mmol) and aluminum chloride (1416 mg, 10.62 mmol) in 1,2-dichlorobenzene (7 mL) was heated at 170° C. for 24 h. The mixture was diluted with DCM and washed with water and brine, then dried and concentrated. Purification by ISCO (24 g REDISEP® column, gradient elution, 0-30% ethyl acetate in hexanes) gave Preparation 5C (580 mg, 96%): LCMS: RT=1.501 min (H2O/MeOH with TFA, ZORBAX® C-18 5 μm (4.6×50) mm, gradient=3 min, wavelength=220 nm); MS(ES):m/z=228 [M+H]+, 1H NMR (300 MHZ, CDCl3) δ 7.41-7.46 (m, 6H), 7.18-7.30 (m, 2H), 3.58 (m, 2H).

Preparation 5D: 4-Fluoro-5-(4-methoxybenzyl)-5H-dibenzo[b,d]azepin-6(7H)-one

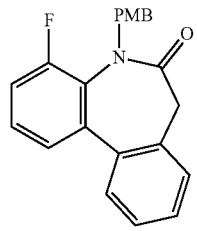

(5D)

To a solution of Preparation 5C (270 mg, 1.188 mmol) in THF (5.4 mL) was added tetrabutylammonium bromide (38.3 mg, 0.119 mmol), KOH (74.7 mg, 1.331 mmol) and 4-methoxybenzyl chloride (0.162 mL, 1.188 mmol). The reaction mixture was stirred at room temperature for 3 hours, then diluted with DCM and half saturated NaCl solution. The aqueous layer was extracted with DCM twice. The combined extracts were dried and concentrated. The residue was purified by ISCO (12 g REDISEP® column, gradient elution, 0-15% ethyl acetate in hexanes) to give Preparation 5D (370 mg, 90%): LCMS: HPLC: RT=2.105 min (MeCN/H2O with HCOONH4, Ascentis Express C8 2.7 μm (5×2.1) mm, gradient=4 min, wavelength=220 nm); MS(ES): m/z=348 [M+H]+; 1H NMR (CDCl3) δ 7.36-7.46 (m, 4H), 7.18-7.22 (m, 2H), 7.07-7.12 (m, 1H), 6.43-6.52 (m, 4H), 5.59 (d, J=14.8 Hz, 1H), 4.33 (dd, J=14.8, 0.8 Hz, 1H), 3.65 (s, 3H), 3.52 (dd, J=52.4, 12.4 Hz, 2H).

Preparation 5E: 7-Azido-4-fluoro-5-(4-methoxybenzyl)-5H-dibenzo[b,d]azepin-6(7H)-one

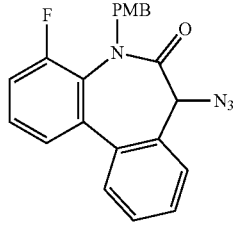

(5E)

LDA (2.0 M in THF/heptane/ethylbenzene, 1.727 mL, 3.45 mmol) was added to a solution of Preparation 5D (1 g, 2.88 mmol) in THF (10 mL) at –78° C. and stirred for 1.5 hours. A solution of 2,4,6-triisopropylbenzenesulfonyl azide (1.069 g, 3.45 mmol) in THF (10 mL) was added to the reaction mixture at –78° C. and stirred for 1 hour. AcOH (3 mL) was added, and stirring was continued at –78° C. After 60 min, the reaction mixture was brought to room temperature slowly and stirred overnight. The reaction was quenched with 10% NaHCO3 solution. The reaction mixture was extracted with EtOAc, dried and concentrated. The residue was purified by ISCO (24 g REDISEP® column, gradient elution, 0-25% ethyl acetate in hexanes) to give Preparation 5E (1 g, 80%): LCMS: RT=1.17 min (H2O/MeCN with NH4OAc, Xbridge BEH C18 2.5 μm (2.1×50) mm, gradient=2.5 min, wavelength=220 nm); MS(ES):m/z=389 [M+H+], 1H NMR (CDCl3) δ 7.40-7.42 (m, 4H), 7.12-7.25 (m, 3H), 6.54 (d, J=9.2 Hz, 2H), 6.45 (d, J=9.2 Hz, 2H), 5.58 (d, J=14.8 Hz, 1H), 5.46 (s, 1H), 4.44 (d, J=14.8 Hz, 1H), 3.65 (s, 3H);

19F NMR (CDCl3) δ –116.6 ppm.

Preparation 5F: 7-Amino-4-fluoro-5-(4-methoxybenzyl)-5H-dibenzo[b,d]azepin-6(7H)-one

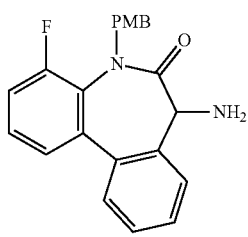

(5F)

To a solution of Preparation 5E (1 g, 2.57 mmol) in ethyl acetate (12 mL) was added palladium hydroxide on carbon (0.155 g, 1.107 mmol). The atmosphere was exchanged for $H_2$, and the reaction mixture was stirred overnight. The mixture was filtered through CELITE® and the filtrate was concentrated. The residue was purified by ISCO (24 g REDISEP® column, gradient elution, 0-70% ethyl acetate in hexanes) to give Preparation 5F (600 mg, 64%): LCMS: RT=1.434 min ($H_2O$/MeOH with TFA, ZORBAX® C-18 5 μm (4.6×50) mm, gradient=3 min, wavelength=220 nm); MS(ES):m/z=363 [M+H$^+$]; $^1$H NMR (CDCl$_3$) δ 7.36-7.39 (m, 4H), 7.08-7.24 (m, 3H), 6.45-6.57 (m, 4H), 5.61 (d, J=14.8 Hz, 1H), 4.93 (s, 1H), 4.42 (d, J=14.8 Hz, 1H), 3.64 (s, 3H); $^{19}$F NMR (CDCl$_3$) δ −117.2 ppm.

Preparation 5G: 7-Amino-4-fluoro-5H-dibenzo[b,d]azepin-6(7H)-one

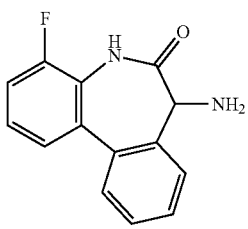

(5G)

To a solution of Preparation 5F (600 mg, 1.656 mmol) in TFA (12 mL) was added methanesulfonic acid (0.1 mL, 1.540 mmol). The reaction mixture was heated to 70° C. and stirred overnight. The reaction mixture was evaporated. The residue was basified using 10% NaHCO$_3$ and extracted with EtOAc. This material was combined with material from a second reaction run using 100 mg of Preparation 5F. The combined organic layers were evaporated to give Preparation 5G (500 mg, >99%), which was used in the next step without further purification: LCMS: RT=0.969 min ($H_2O$/MeOH with TFA, ZORBAX® C-18 5 μm (4.6×50) mm, gradient=3 min, wavelength=220 nm); MS(ES):m/z=243 [M+H$^+$]; $^1$H NMR (DMSO-d$_6$) δ 10.1 (s, 1H), 7.71 (d, J=8.0 Hz, 1H), 7.59 (dd, J=7.6, 1.2 Hz, 1H), 7.53 (td, J=7.6, 1.2 Hz, 1H), 7.49 (m, 1H), 7.44 (td, J=7.2, 1.2 Hz, 1H), 7.33-7.41 (m, 2H), 4.16 (s, 1H), 2.35 (br s, 2H).

Example 5

Example 5 was prepared from Preparation 3E and Preparation 5G using the general procedure given for Example 1.

HPLC: RT=1.847 (MeOH/H$_2$O/0.1% TFA, Waters SunFire C18 2.1×30 mm, 2 min gradient, wavelength=254 nm); MS(ES): m/z=492 [M+1]+; $^1$H NMR (400 MHz, DMSO-d$_6$) δ 10.25 (s, 1H), 9.12 (d, J=8.4 Hz, 1H), 7.66 (d, J=7.3 Hz, 1H), 7.59-7.54 (m, 5H), 7.54-7.36 (m, 4H), 6.95 (br. s., 1H), 5.26 (d, J=8.4 Hz, 1H), 2.90-2.81 (m, 1H), 2.47-2.42 (m, 1H), 2.39-2.13 (m, 2H), 1.66-1.55 (m, 2H), 0.93-0.82 (m, 1H), 0.59-0.47 (m, 1H), 0.38-0.22 (m, 2H), −0.05-−0.12 (m, 1H), −0.18-−0.25 (m, 1H).

Example 6

(2R,3R)-N-((7S)-6-Oxo-6,7-dihydro-5H-dibenzo[b,d]azepin-7-yl)-3-phenyl-2-(3,3,3-trifluoropropyl)succinamide

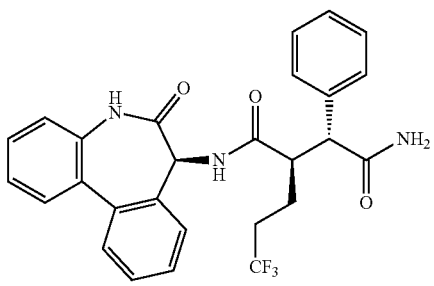

(6)

Preparation 6A: tert-Butyl 2-phenylacetate

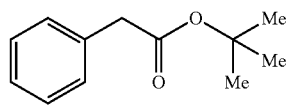

(6A)

A solution of 2-phenylacetic acid (12 g, 88 mmol) in tBuOAc (250 mL) was treated with perchloric acid (70% redistilled, 0.212 mL, 3.53 mmol) and stirred at room temperature for 20 hours. The solution was transferred very slowly to stirred mixture of saturated aqueous NaHCO$_3$ and Et$_2$O [Caution: Lots of bubbling]. The resulting layers were separated and the organic layer was washed with saturated aqueous NaHCO$_3$, dried over MgSO$_4$, filtered, and concentrated to give Preparation 6A (11.6 g, 68% yield). $^1$H NMR (500 MHz, CDCl$_3$) δ 7.34-7.29 (m, 2H), 7.28-7.22 (m, 3H), 3.52 (s, 2H), 1.44 (s, 9H).

Preparation 6B: (2R)-5,5,5-Trifluoro-2-hydroxypentanoic acid

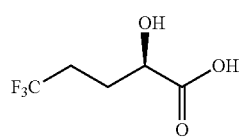

(6B)

To a cool (0° C.), stirred solution of (2R)-2-amino-5,5,5-trifluoropentanoic acid (4.09 g, 23.90 mmol), prepared according to the process disclosed in U.S. Publication No. 2009/0111858 A1, and H$_2$SO$_4$ (2.8 mL, 52.5 mmol) in water (95 mL) was added a solution of sodium nitrite (9.89 g, 143 mmol) in water (30 mL) dropwise via addition funnel over 60 min. The reaction mixture was allowed to slowly warm to room temperature and stirred overnight. The reaction mixture was diluted with Et$_2$O, the aqueous phase was separated and extracted with Et$_2$O (3×). The combined organics were dried (Na$_2$SO$_4$), filtered and concentrated under reduced pressure to provide Preparation 6B (4.1551 g, >99%) as an amber oil. $^1$H NMR (400 MHz, CDCl$_3$) δ 4.33 (1H, dd, J=8.03, 4.27 Hz), 2.09-2.42 (3H, m), 1.88-2.02 (1H, m).

Preparation 6C: Benzyl (2R)-5,5,5-trifluoro-2-hydroxypentanoate

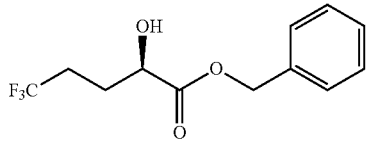

(6C)

To a stirred solution of Preparation 6B (4.1551 g, 24.14 mmol) and benzyl alcohol (3.2 mL, 30.8 mmol) in benzene (40 mL) was added H$_2$SO$_4$ (0.28 mL, 5.25 mmol). The reaction mixture was heated to 50° C. for 10 h. The reaction mixture was cooled to room temperature, cooled in ice/water bath, and then 0.5M NaOH (32 mL, 16.00 mmol) was added. The mixture was stirred for a few minutes, and was extracted with Et$_2$O, washed with brine, dried (Na$_2$SO$_4$), filtered and concentrated under reduced pressure. The residue was purified by flash chromatography (Teledyne ISCO CombiFlash Rf, 0% to 100% solvent CH$_2$Cl$_2$/EtOAc, REDISEP® SiO$_2$ 120 g). Concentration of appropriate fractions provided Preparation 6C (3.88 g, 61%) as a colorless oil: $^1$H NMR (400 MHz, CDCl$_3$) δ 7.33-7.44 (5H, m), 5.25 (2H, s), 4.28 (1H, dt, J=8.09, 4.11 Hz), 2.85 (1H, d, J=4.77 Hz), 2.07-2.34 (3H, m), 1.84-1.96 (1H, m).

Preparation 6D: Benzyl (2R)-5,5,5-trifluoro-2-{[(trifluoromethyl)sulfonyl]oxy}pentanoate

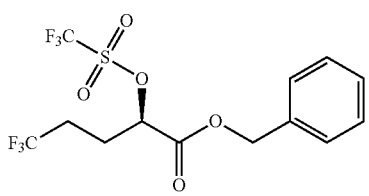

(6D)

To a cold (−25° C.), stirred solution of 2,6-lutidine (2.352 mL, 20.19 mmol) in CH$_2$Cl$_2$ (30 mL) was added triflic anhydride (3.18 mL, 18.85 mmol) slowly over 2 minutes. The reaction mixture was stirred at −25° C. and became light yellow/orange in color. After 10 min, Preparation 6C (3.53 g, 13.46 mmol) was added dropwise over 5 min and stirred at −25° C. for 30 minutes. The reaction mixture was warmed to room temperature and concentrated to a small volume. The residue was diluted with heptane and loaded directly onto a silica gel column (220 g), eluted with a gradient from 20% CH$_2$Cl$_2$/heptane to 50% CH$_2$Cl$_2$/heptane. Concentration of appropriate fractions provided Preparation 6D (3.476 g, 66%): $^1$H NMR (400 MHz, CDCl$_3$) δ 7.33-7.45 (5H, m), 5.29 (2H, d, J=5.50 Hz), 5.21 (1H, t, J=5.50 Hz), 2.04-2.37 (4H, m).

Preparation 6E: (2R,3R)-1-Benzyl 4-tert-butyl 3-phenyl-2-(3,3,3-trifluoropropyl)succinate

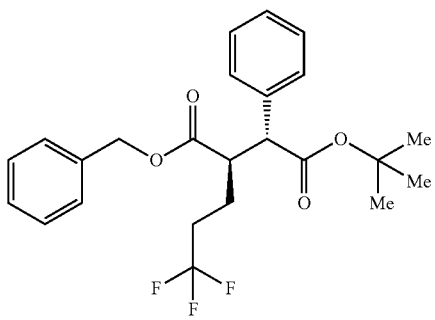

(6E)

A solution of Preparation 6A (8.5 g, 44.2 mmol) in THF (400 mL) was cooled in −78° C. bath and treated with a solution of KHMDS (0.5M in toluene, 97 mL, 48.6 mmol) via cannula over 10 minutes. After 10 minutes, the mixture was removed from the −78° C. bath and placed in a room temperature water bath, stirred for 15 minutes, and then again cooled in a −78° C. bath.

After 15 minutes, a solution of Preparation 6D (19.18 g, 48.6 mmol) in THF (50 mL) was added over 10 min via cannula with a 20 mL THF rinse. The reaction mixture was stirred at −78° C. for 1 hour and then quenched with saturated aqueous NH$_4$Cl. The mixture was removed from the −78° C. bath, diluted with 10% aqueous LiCl, and extracted with Et$_2$O. The organic layer was dried over MgSO$_4$, filtered and concentrated. The resulting light brown residue was dissolved in 100 mL CH$_2$Cl$_2$ and treated with charcoal and MgSO$_4$. The mixture was filtered to give an almost colorless solution. The CH$_2$Cl$_2$ solution was concentrated, diluted with hexane and cooled in a −20° C. freezer. The resulting solids were filtered, rinsed with cold hexane containing 5% MTBE and dried on fritted filter funnel under a stream of nitrogen to give a solid. The solid was triturated with 40 mL hexane and 4 mL MTBE stirring the white suspension at room temperature for 1 hour and then cooling at −20° C. for 3 hours before filtering the white solid and washing with cold solvent (10:1 hexane: MTBE) to give Preparation 6E (7.16 g, 37% yield) as a white solid. $^1$H NMR (500 MHz, chloroform-d) δ 7.32-7.23 (m, 8H), 7.05-6.97 (m, 2H), 4.89-4.76 (m, 2H), 3.69 (d, J=11.4 Hz, 1H), 3.23 (ddd, J=11.2, 9.9, 3.9 Hz, 1H), 2.19-2.04 (m, 2H), 2.03-1.88 (m, 2H), 1.40 (s, 9H).

Preparation 6F: (R)-2-((R)-2-(tert-Butoxy)-2-oxo-1-phenylethyl)-5,5,5-trifluoropentanoic acid

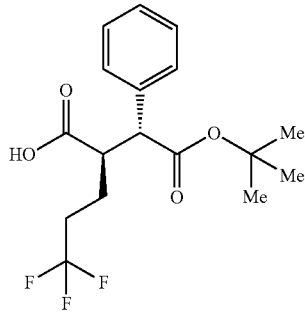

(6F)

A suspension of Preparation 6E (7.16 g, 16.40 mmol) and Pd/C, 10% (1.746 g, 1.640 mmol) in ethyl acetate (35 mL) and MeOH (35 mL) was hydrogenated using a hydrogen filled balloon while stirring at room temperature. When the reaction was complete by HPLC, the suspension was filtered through 0.45 μm membrane and rinsed with MeOH and EtOAc. The filtrate was concentrated and dried under vacuum to give Preparation 6F (5.65 g, 99% yield). LCMS [M−H]$^-$=345. $^1$H NMR (500 MHz, DMSO-d$_6$) δ 7.37-7.26 (m, 5H), 3.67 (d, J=10.5 Hz, 1H), 3.04 (td, J=10.3, 3.7 Hz, 1H), 2.38-2.20 (m, 2H), 1.88-1.70 (m, 2H), 1.37 (s, 9H).

Example 6

Example 6 was prepared from Preparation 6F and Preparation 1H according to the general procedure described for Example 1. HPLC: RT=9.55 min (H$_2$O/CH$_3$CN with TFA, SunFire C18 3.5 μm, 3.0×150 mm, gradient=15 min, wavelength=220 and 254 nm); MS(ES):m/z=496.15 [M+H$^+$]; $^1$H NMR (400 MHz, methanol-d$_4$) δ 7.69-7.56 (m, 1H), 7.56-7.41 (m, 4H), 7.41-7.28 (m, 5H), 7.23 (s, 1H), 7.14-6.93 (m, 1H), 6.11-5.97 (m, 1H), 5.09 (s, 1H), 3.78-3.64 (m, 1H), 3.62-3.46 (m, 1H), 2.48-2.06 (m, 2H), 2.06-1.68 (m, 2H).

Example 7

(2R,3S)-3-(3,3-Difluorocyclobutyl)methyl)-N-((7S)-6-oxo-6,7-dihydro-5H-dibenzo[b,d]azepin-7-yl)-2-(3,3,3-trifluoropropyl)succinamide

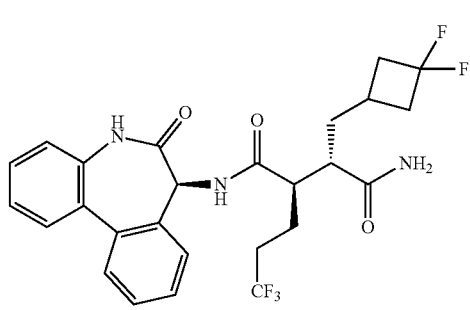

(7)

Preparation 7A: Diethyl 2-((2,2-dichloro-3-oxocyclobutyl)methyl)malonate

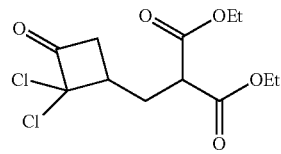

(7A)

To a stirred suspension of Cu.Zn (1.771 g, 13.73 mmol) and diethyl 2-allylmalonate (1.084 mL, 5.49 mmol) in anhydrous Et$_2$O (20 mL) at reflux was added a solution of phosphorus oxychloride (1.127 mL, 12.09 mmol) and 2,2,2-trichloroacetyl chloride (1.357 mL, 12.09 mmol) in Et$_2$O (10 mL) dropwise through an addition funnel over 2 h. The resulting mixture was then heated at reflux overnight. After cooling to room temperature, the mixture was filtered through CELITE® and washed with EtOAc. The filtrate was concentrated and the residue was purified by silica gel column chromatography (80 g, EtOAc/hexane=0-50%) to afford Preparation 7A (1.59 g, 93%).
$^1$H NMR (400 MHz, CDCl$_3$) δ 4.32-4.23 (m, 4H), 3.58 (dd, J=8.9, 6.1 Hz, 1H), 3.47-3.32 (m, 1H), 3.16-2.92 (m, 2H), 2.51 (ddd, J=14.3, 7.2, 6.1 Hz, 1H), 2.40-2.25 (m, 1H), 1.36-1.30 (m, 6H).

Preparation 7B: Diethyl 2-((3-oxocyclobutyl)methyl)malonate

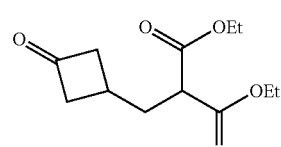

(7B)

To a vigorously stirred mixture of zinc (10.42 g, 159 mmol) in acetic acid (50 mL) at 0° C. was added a solution of Preparation 7A (12.4 g, 39.9 mmol) in acetic acid (50 mL) dropwise. The mixture was then heated to 60° C. overnight. After cooling to room temperature, the reaction mixture was poured into ice-water and extracted with EtOAc. The organic layer was washed with water, saturated aqueous NaHCO$_3$ and brine, and then dried and concentrated. The residue was purified by silica gel column chromatography (220 g column, EtOAc/hexane=0-40%) to afford Preparation 7B (6.91 g, 71.6%). $^1$H NMR (400 MHz, CDCl$_3$) δ 4.29-4.19 (m, 4H), 3.35 (t, J=7.5 Hz, 1H), 3.25-3.12 (m, 2H), 2.82-2.71 (m, 2H), 2.53-2.38 (m, 1H), 2.24 (t, J=7.6 Hz, 2H), 1.33-1.28 (m, 6H).

Preparation 7C: Diethyl 2-((3,3-difluorocyclobutyl)methyl)malonate

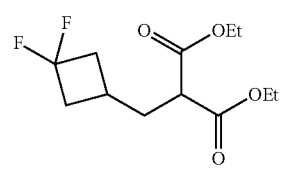

(7C)

To a solution of Preparation 7B (6.9 g, 28.5 mmol) in DCM (100 mL) at 0° C. was added DAST (12 mL, 91 mmol) dropwise. The mixture was stirred at room temperature overnight. After cooling to 0° C., saturated aqueous NaHCO₃ was carefully added. The mixture was stirred for 30 min until bubbles ceased. The organic layer was separated, dried and concentrated. The residue was purified by silica gel column chromatography (80 g column, EtOAc/hexane=0-20%) to afford Preparation 7C (6.48 g, 86%). ¹H NMR (400 MHz, CDCl₃) δ 4.27-4.16 (m, 4H), 3.28 (t, J=7.3 Hz, 1H), 2.79-2.61 (m, 2H), 2.30-2.07 (m, 5H), 1.33-1.26 (m, 6H).

Preparation 7D:
2-((3,3-Difluorocyclobutyl)methyl)malonic acid

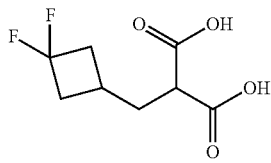

(7D)

To a solution of Preparation 7C (6.48 g, 24.52 mmol) in EtOH (25 mL) was added 4 N NaOH (25 mL, 100 mmol). The mixture was heated to reflux at 100° C. for 2 h. After cooling to room temperature, the mixture was concentrated to about half of the volume. The residue was then extracted with ether, and the ether layer was back extracted with some water. The combined aqueous layers were acidified with concentrated HCl and extracted with EtOAc. The combined extracts were dried over MgSO₄, filtered and concentrated. The crude residue was sonicated with hexane, and the solid precipitate was collected by filtration, rinsed with hexane, and dried to afford Preparation 7D (4.86 g, 95%). ¹H NMR (400 MHz, DMSO-d₆) δ 12.75 (br. s., 1H), 3.18 (t, J=7.4 Hz, 1H), 2.69-2.53 (m, 2H), 2.33-2.14 (m, 2H), 2.14-1.99 (m, 1H), 1.95-1.85 (m, 2H).

Preparation 7E: 3-(3,3-Difluorocyclobutyl)propanoic acid

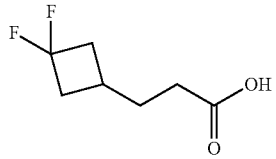

(7E)

Preparation 7D (4.86 g, 23.35 mmol) in a 30 mL closed vial equipped with a balloon was heated at 160° C. for 1 h. The reaction mixture was cooled to room temperature to afford Preparation 7E (3.8 g, 99%). MS(ES):m/z=163 [M−H⁺]; ¹H NMR (400 MHz, DMSO-d₆) δ 12.10 (br. s., 1H), 2.73-2.54 (m, 2H), 2.29-2.00 (m, 5H), 1.69 (q, J=7.5 Hz, 2H).

Preparation 7F: tert-Butyl 3-(3,3-difluorocyclobutyl)propanoate

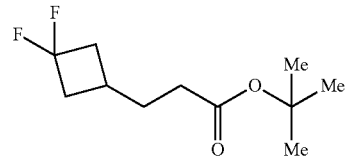

(7F)

To a cool (0° C.), stirred solution of Preparation 7E (3.8 g, 23.15 mmol) in hexane (20 mL) and THF (20 mL) under N₂ was added tert-butyl 2,2,2-trichloroacetimidate (8.29 mL, 46.3 mmol) portionwise over 5 min and the reaction mixture was stirred for 15 min. Boron trifluoride ether complex (0.293 mL, 2.315 mmol) was added at 0° C. and the reaction mixture was allowed to warm to room temperature as the bath warmed and stirred overnight. To the clear reaction mixture was added NaHCO₃ (5 g), and stirring was continued for 60 min. The suspension was filtered through MgSO₄, washed with 300 mL hexane and the resulting solution was allowed to sit for several hours. The resulting solid was filtered through the same MgSO₄ filter, and washed with hexane (100 mL). The filtrate was concentrated and the crude material was purified by ISCO (120 g) eluting with 100% hexane to 20% EtOAc in hexane to afford Preparation 7F (4.4 g, 19.98 mmol, 86% yield). ¹H NMR (400 MHz, CDCl₃) δ 2.85-2.53 (m, 2H), 2.31-2.08 (m, 5H), 1.80 (q, J=7.2 Hz, 2H), 1.47 (s, 9H).

Preparation 7G: (S)-4-Isopropyl-3-(5,5,5-trifluoropentanoyl)oxazolidin-2-one

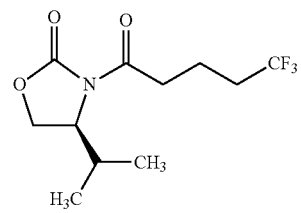

(7G)

To a stirred solution of 5,5,5-trifluoropentanoic acid (5.04 g, 32.3 mmol) in DCM (50 mL) and DMF (3 drops) was added oxalyl chloride (3.4 mL, 38.8 mmol) dropwise over 5 min. The solution was stirred until all bubbling subsided. The reaction mixture was concentrated under reduced pressure to give a pale yellow oil. To a separate flask charged with a solution of (4S)-4-(propan-2-yl)-1,3-oxazolidin-2-one (4.18 g, 32.4 mmol) in THF (100 mL) at −78° C. was added n-BuLi (13.0 mL, 32.5 mmol, 2.5M in hexane) dropwise via syringe over 5 min. After stirring for 10 min, the above acid chloride dissolved in THF (20 mL) was added via cannula over 15 min. The reaction mixture was warmed to 0° C., and was allowed to warm to room temperature as the bath warmed and stirred overnight. To the reaction mixture was added saturated NH₄Cl, and then extracted with EtOAc (2×). The combined organics were washed with brine, dried (Na₂SO₄), filtered and concentrated under reduced pressure. The crude material was purified by silica gel chromatography (hexanes/EtOAc) to provide Preparation 7G (7.39 g, 86%) as a colorless oil: ¹H NMR (400 MHz, CDCl₃) δ 4.44 (1H, dt, J=8.31, 3.53 Hz), 4.30 (1H, t, J=8.69 Hz), 4.23 (1H, dd, J=9.06, 3.02 Hz), 2.98-3.08 (2H, m), 2.32-2.44 (1H, m, J=13.91, 7.02, 7.02, 4.03 Hz), 2.13-2.25 (2H, m), 1.88-2.00 (2H, m), 0.93 (3H, d, J=7.05 Hz), 0.88 (3H, d, J=6.80 Hz).

Preparation 7H: (2S,3R)-tert-Butyl 2-((3,3-difluorocyclobutyl)methyl)-6,6,6-trifluoro-3-((S)-4-isopropyl-2-oxooxazolidine-3-carbonyl)hexanoate, and Preparation 7I: (2R,3R)-tert-Butyl 2-((3,3-difluorocyclobutyl)methyl)-6,6,6-trifluoro-3-((S)-4-isopropyl-2-oxooxazolidine-3-carbonyl)hexanoate

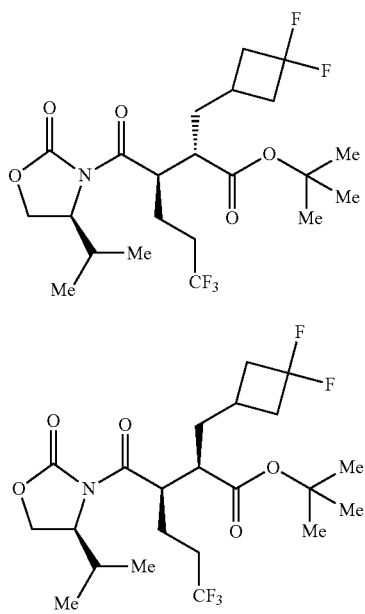

Diisopropylamine (3.01 mL, 21.11 mmol) was dissolved in 28.8 mL of THF and cooled to −78° C. BuLi (1.6 M in hexane) (13.10 mL, 20.95 mmol) was added dropwise over a period of 5 minutes. After 5 minutes, the ~0.5 M LDA solution was kept at 0° C. In a separate flask, lithium chloride (1.221 g, 28.8 mmol) was dried in an oven overnight, and then under high vacuum while heating with a heat gun and then cooled under nitrogen. Preparation 7G (1.4 g, 5.24 mmol), having been azeotroped once with toluene, was transferred (under nitrogen) with toluene (10 mL) to the flask containing LiCl, and then cooled to −78° C. Preparation 7F (2.077 g, 9.43 mmol), having been azeotroped once with toluene, was dissolved in toluene (10 mL) and cooled to −78° C. The solution of LDA (13.1 mL of a 0.5 M LDA solution) was added dropwise to the LiCl/oxazolidinone (1.4 g, 5.24 mmol) solution at −78° C. over a period of 5 minutes. The reaction mixture was stirred at −78° C. for 15 minutes, and then at 0° C. for 10 minutes and then cooled to −78° C. A solution of LDA (23.6 mL of a 0.5 M LDA solution) was added dropwise to the solution of Preparation 7F and stirred at −78° C. for 30 minutes. This solution was then added via cannula (fast negative pressure, all added within 30 seconds) to the LiCl/oxazolidinone solution at −78° C. After 1 minute following the transfer, solid bis((2-ethylhexanoyl)oxy)copper (5.50 g, 15.72 mmol), having been dried in an oven overnight, was added at −78° C., and the flask was transferred to a 40° C. water bath and swirled for 15 minutes. The reaction was quenched with 5% NH$_4$OH solution (30 mL saturated NH$_4$OH in 150 mL water), and extracted 2×100 mL with ethyl acetate. The combined extracts were washed with brine, dried and concentrated. The crude mixture was purified by ISCO (40 g, EtOAc/hexane, 0-35%) to give a mixture of Preparation 7H and Preparation 7I (1.196 g, 47%, as a mixture of isomers=1.3:1, 7H:7I).

Preparation 7J: (R)-2-((S)-1-(tert-Butoxy)-3-(3,3-difluorocyclobutyl)-1-oxopropan-2-yl)-5,5,5-trifluoropentanoic acid, and Preparation 7K: (R)-2-((R)-1-(tert-Butoxy)-3-(3,3-difluorocyclobutyl)-1-oxopropan-2-yl)-5,5,5-trifluoropentanoic acid

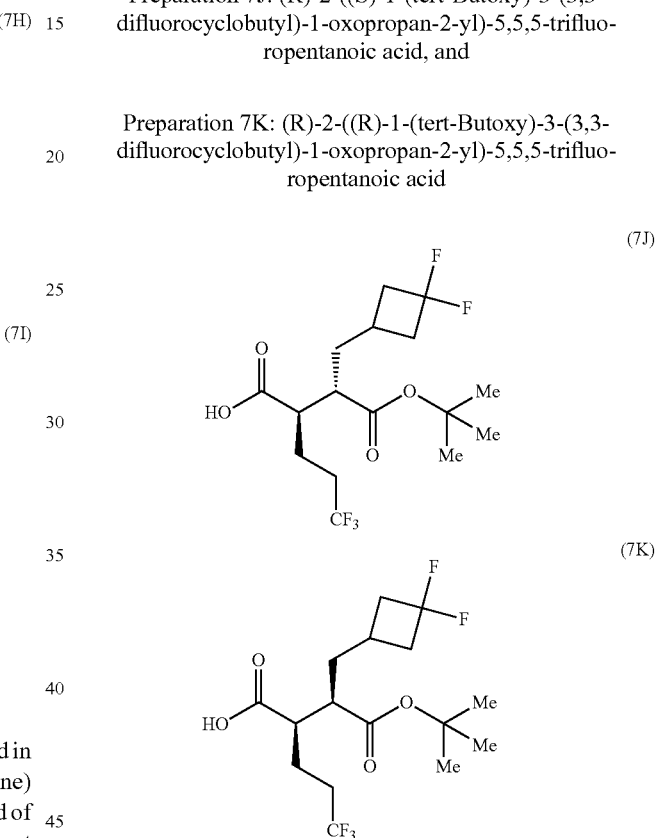

To an ice-water cooled solution of LiOH (0.176 g, 7.35 mmol) in water (7 mL) was added 50% H$_2$O$_2$ (1.502 mL, 24.51 mmol) dropwise. The resulting solution was added dropwise to a solution of al 0.3:1 mixture of Preparation 7H and Preparation 7I (1.85 g, 4.23 mmol) in THF (21 mL) at 0° C. The mixture was stirred at 0° C. and the warmed to room temperature over a weekend. The resulting mixture was treated with saturated aqueous NaHCO$_3$ (10 mL), followed by the slow addition of aqueous Na$_2$S$_2$O$_3$ (20 mL). The mixture was stirred for 1 h and then concentrated to remove the THF. To the aqueous layer was added 1N NaOH (4 mL), and the mixture was extracted with DCM. The aqueous layer was cooled in an ice-water bath and slowly acidified with concentrated HCl until pH 3. The resulting mixture was saturated with solid NaCl and extracted with EtOAc. The combine extracts were washed with saturated NaCl, dried with MgSO$_4$, filtered and concentrated to afford Preparation 7J and Preparation 7K (1.19 g, 130% yield, as a diastereomer mixture of 9K:9J=1:1.3). MS(ES):m/z=373 [M−H$^+$].

Preparation 7J: (R)-2-((S)-1-(tert-Butoxy)-3-(3,3-difluorocyclobutyl)-1-oxopropan-2-yl)-5,5,5-trifluoropentanoic acid, and Preparation 7K: (R)-2-((R)-1-(tert-Butoxy)-3-(3,3-difluorocyclobutyl)-1-oxopropan-2-yl)-5,5,5-trifluoropentanoic acid

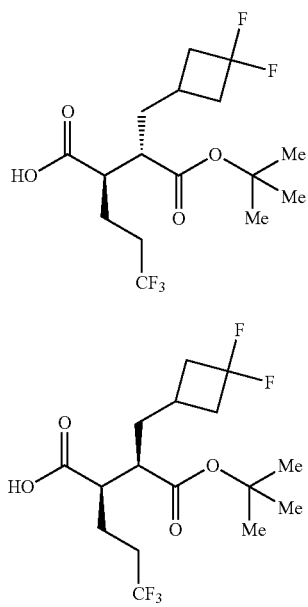

(7J)

(7K)

To a cold (−78° C.), stirred solution of a 1.3:1 mixture of Preparation 7J: Preparation 7K (1.08 g, 2.89 mmol) in THF (16 mL) was added LDA (2.0M in THF/hexane/ethyl benzene) (3.5 mL, 7.00 mmol) dropwise via syringe over 5 min (internal temperature never exceeded −64° C., J-KEM® probe in reaction solution). The reaction mixture was stirred for 15 min, and then warmed to room temperature (24° C. water bath) and stirred for 15 min. The mixture was then cooled to −78° C. for 15 min. To the reaction mixture was added Et$_2$AlCl (1M in hexane) (7.2 mL, 7.20 mmol) via syringe (internal temperature never exceeded −55° C.) and stirred for 10 min, and then warmed to room temperature (24° C. bath) for 15 min. The mixture was then cooled back to −78° C. for 15 min. The reaction mixture was transferred via cannula over 5 min to a 250 mL round bottom flask charged with MeOH (26 mL, 643 mmol), precooled to −78° C. with vigorous stirring. The flask was removed from the bath, ice was added followed by the slow addition of 1N HCl (26 mL, 26.0 mmol). The reaction mixture was allowed to warm to room temperature, during which the gas evolution subsided. The reaction mixture was diluted with EtOAc (250 mL), and the organic phase was separated. The organic phase was washed with a solution of potassium fluoride (1.51 g, 26.0 mmol) and 1N HCl (7.2 mL, 7.20 mmol) in water (50 mL, 2775 mmol), followed by brine, and then dried (Na$_2$SO$_4$) filtered and concentrated to dryness to afford a 12.3:1 (7J:7K) mixture of diastereomers. The crude material was used in the next step without further purification.

Preparation 7L: (2R,3S)-1-Benzyl 4-tert-butyl 3-((3,3-difluorocyclobutyl)methyl)-2-(3,3,3-trifluoropropyl)succinate

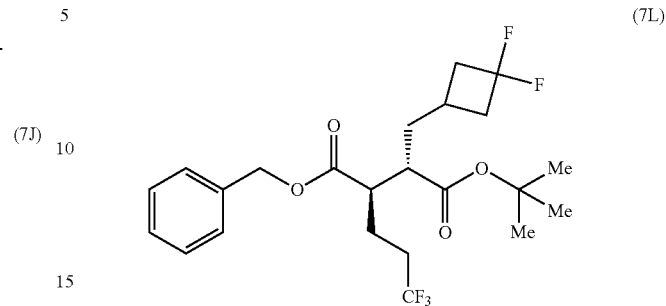

(7L)

To a solution of a mixture of Preparation 7J and Preparation 7K (1.1 g, 2.94 mmol) in DMF (10 mL) was added K$_2$CO$_3$ (0.690 g, 5.00 mmol) and benzyl bromide (0.524 mL, 4.41 mmol). The mixture was stirred at room temperature overnight. Water (100 mL) was added and the mixture was extracted with EtOAc (2×100 mL). The combined extracts were washed with 10% LiCl (2×100 mL), then brine (100 mL) and dried (Na$_2$SO$_4$), filtered and concentrated to dryness. The crude mixture of diastereomers were separated by silica gel chromatography (SiO$_2$, 120 g column, 0% toluene/hexanes to 80% toluene/hexanes, 15 min. gradient) to afford Preparation 7L (0.89, 65%). $^1$H NMR (400 MHz, CDCl$_3$) δ 7.43-7.35 (m, 5H), 5.24-5.15 (m, 2H), 2.72-2.55 (m, 3H), 2.48 (td, J=10.2, 3.5 Hz, 1H), 2.17-1.95 (m, 5H), 1.93-1.81 (m, 2H), 1.79-1.69 (m, 1H), 1.46 (s, 9H), 1.37-1.28 (m, 1H).

Preparation 7J: (R)-2-((S)-1-(tert-Butoxy)-3-(3,3-difluorocyclobutyl)-1-oxopropan-2-yl)-5,5,5-trifluoropentanoic acid

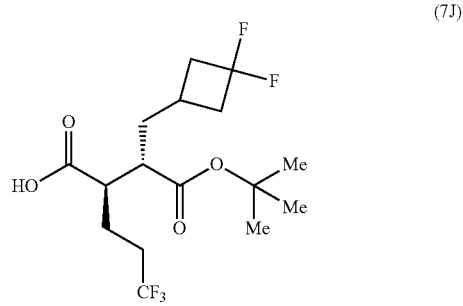 [SMILES: CC(C)(C)OC(=O)[C@@H](CC1CC(F)(F)C1)[C@@H](CCC(F)(F)F)C(=O)O]

(7J)

A solution of Preparation 7L (870 mg, 1.873 mmol) in MeOH (37.500 ml) was treated with 10% palladium on carbon (100 mg, 0.940 mmol) under a nitrogen atmosphere. The reaction mixture was purged with nitrogen and then with H$_2$ gas. The reaction mixture was stirred under a hydrogen atmosphere at room temperature. After 4 hours the reaction mixture was filtered through a pad of CELITE® and the cake was washed with MeOH. The filtrate was concentrated to dryness to afford Preparation 7J (660 mg, 94%). $^1$H NMR (400 MHz, CDCl$_3$) δ 2.77-2.63 (m, 3H), 2.56 (ddd, J=10.3, 8.6, 3.7 Hz, 1H), 2.36-2.06 (m, 5H), 2.05-1.87 (m, 2H), 1.84-1.72 (m, 1H), 1.61-1.52 (m, 1H), 1.49 (s, 9H).

Example 7

Example 7 was prepared from Preparation 1H and Preparation 7J using the general procedure given for Example 1.

Example 7: HPLC: RT=9.87 min (H₂O/CH₃CN with TFA, SunFire C18 3.5 μm, 4.6×150 mm, gradient=15 min, wavelength=220 and 254 nm); MS(ES):m/z=524.3 [M+H⁺]; 6 $^1$H NMR (400 MHz, DMSO-d$_6$) δ 10.40 (s, 1H), 9.17 (d, J=8.4 Hz, 1H), 7.73 (d, J=6.6 Hz, 1H), 7.65-7.61 (m, 1H), 7.58 (br. s., 2H), 7.56-7.46 (m, 4H), 7.40-7.34 (m, 1H), 7.27 (d, J=7.9 Hz, 1H), 7.02 (br. s., 1H), 5.26 (d, J=8.4 Hz, 1H), 2.95-2.84 (m, 1H), 2.58 (d, J=12.3 Hz, 2H), 2.41-2.30 (m, 2H), 2.25 (d, J=10.3 Hz, 1H), 2.14-1.87 (m, 3H), 1.85-1.74 (m, 1H), 1.66-1.55 (m, 2H), 1.30 (d, J=9.5 Hz, 1H).

Example 8

(2R,3S)-N-(4-Chloro-6-oxo-6,7-dihydro-5H-dibenzo[b,d]azepin-7-yl)-2,3-bis(3,3,3-trifluoropropyl)succinamide

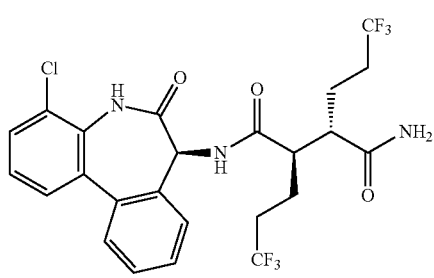

(8)

Preparation 8A: tert-Butyl (3-chloro-[1,1'-biphenyl]-2-yl)carbamate

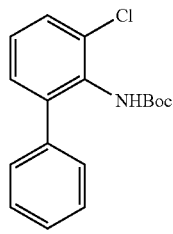

(8A)

To a solution of tert-butyl[1,1'-biphenyl]-2-ylcarbamate (synthesized according to Tsang et al., *J. Org. Chem.*, 7603 (2008)) (12.5 g, 46.4 mmol) in diethyl ether (125 mL) at −30° C. was added tert-butyllithium (1.6 M in pentane, 174 mL, 278 mmol) slowly over 15 minutes. The reaction mixture was stirred for 6 h, then a solution of perchloroethane (43.9 g, 186 mmol) in diethyl ether (125 mL) was added over 10 minutes. The reaction mixture was allowed to warm to room temperature and stirred overnight. The reaction was quenched with saturated aqueous ammonium chloride and extracted twice with EtOAc. The organic layers were washed with brine, dried with sodium sulfate, and concentrated. The residue was purified by silica gel chromatography (EtOAc/petroleum ether) to give Preparation 8A (8.5 g, 60%). HPLC: RT=2.432 min (H₂O/MeCN with TFA, SunFire C18 3.5 μm, 4.6×150 mm, gradient=30 min, wavelength=220 and 254 nm).

Preparation 8B: 3-Chloro-[1,1'-biphenyl]-2-amine

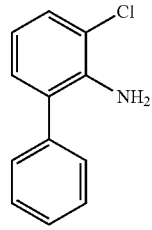

(8B)

To a solution of Preparation 8A (16 g, 52.7) mmol in DCM (160 mL) at 0° C. was added trifluoroacetic acid (28.4 mL, 369 mmol) in DCM (100 mL). The reaction mixture was warmed to room temperature and stirred for 2 hours. The reaction mixture was poured into 10% aqueous sodium bicarbonate, then extracted twice with DCM. The combined organic layers were washed with brine, dried with sodium sulfate, and evaporated to give Preparation 8B (10.5 g, 98%). $^1$H NMR (400 MHz, DMSO-d$_6$) δ 7.51-7.38 (m, 5H), 7.26 (dd, J=8, 1.6 Hz, 1H), 6.99 (dd, J=7.2, 1.6 Hz, 1H), 6.67 (t, J=8 Hz, 1H), 4.77 (br s, 2H).

Preparation 8C: 2-Chloro-N-(3-chloro-[1,1'-biphenyl]-2-yl)acetamide

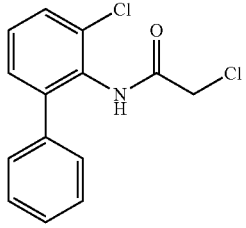

(8C)

To a solution of Preparation 8B (11.0 g, 54.0 mmol) in DCM (150 mL) at 0° C. was added 2-chloroacetyl chloride (9.15 g, 81 mmol). The reaction mixture was warmed to room temperature and stirred for 3 hours. The reaction mixture was diluted with DCM, then washed successively with saturated sodium bicarbonate (twice) and brine. The organic layer was dried with sodium sulfate and concentrated to give Preparation 8C (14.5 g, 96%). $^1$H NMR (400 MHz, chloroform-d) δ 9.94 (s, 1H), 7.58 (dd, J=8.0, 1.2 Hz, 1H), 7.46-7.35 (m, 7H), 4.09 (s, 2H).

Preparation 8D: 4-Chloro-5H-dibenzo[b,d]azepin-6(7H)-one

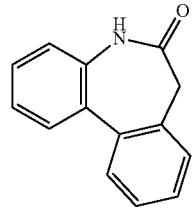

(8D)

To a solution of Preparation 8C (1.00 g, 3.57 mmol) in 1,2-dichlorobenzene (10 mL) was added aluminum chloride (1.90 g, 14.3 mmol). The solution was heated to 170° C. for 24 hours, then cooled to room temperature and diluted with DCM. The reaction mixture was washed with water and brine, then the organic layers were dried with sodium sulfate and evaporated. The residue was purified by silica gel chromatography (EtOAc/petroleum ether) to give Preparation 8D (0.750 g, 86%). HPLC: RT=0.87 min (H$_2$O/MeCN with NH$_4$OAc and HCOOH, AQUITY® BEH C18 1.7 μM, 2.1×50 mm, gradient=2 min, wavelength=220 nm); MS (GCMS): m/z=243.

Preparation 8E: 4-Chloro-5-(4-methoxybenzyl)-5H-dibenzo[b,d]azepin-6(7H)-one

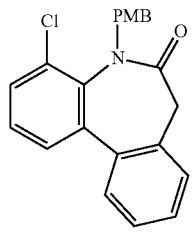

(8E)

To a solution of Preparation 8D (750 mg, 3.08 mmol) in THF (15 mL) was added tetrabutylammonium bromide (99 mg, 0.308 mmol), potassium hydroxide (207 mg, 3.69 mmol) and 4-methoxybenzyl chloride (0.459 mL, 3.39 mmol). The reaction mixture was stirred for 12 hours, then diluted with DCM and washed with brine. The organic layer was dried with sodium sulfate and concentrated. The residue was purified by silica gel chromatography (EtOAc/petroleum ether) to give Preparation 8E (1.5 g, 80%). $^1$H NMR (400 MHz, chloroform-d) δ 7.34 (dd, J=14, 2.8 Hz, 1H), 7.31-7.27 (m, 4H), 7.26-7.22 (m, 2H), 6.44-6.37 (m, 4H), 5.53 (d, J=14 Hz, 1H), 4.41 (d, J=14 Hz, 1H), 3.65 (s, 3H), 3.47 (dd, J=51, 12 Hz, 2H).

Preparation 8F: 7-Azido-4-chloro-5-(4-methoxybenzyl)-5H-dibenzo[b,d]azepin-6(7H)-one

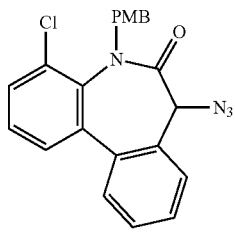

(8F)

To a solution of diisopropylamine (5.00 mL, 35.7 mmol) in THF (50 mL) at −78° C. was added n-butyllithium (2.5M in diethyl ether, 10 mL, 25 mmol). The solution was stirred at 0° C. for 45 min, then cooled to −78° C. A solution of Preparation 8E (5.00 g, 13.7 mmol) in THF (50 mL) was cooled to −78° C., then transferred to the first solution. A solution of 2,4,6-triisopropylbenzenesulfonyl azide (5.10 g, 16.5 mmol) in THF (50 mL) was added over 5 minutes. The reaction mixture was stirred for 1 hour, then acetic acid (15 mL) was added. The reaction mixture was stirred for 0.5 hours, then allowed to gradually warm to room temperature and stirred for 13 hours. The reaction was quenched with saturated aqueous sodium carbonate and extracted twice with EtOAc. The combined organic layers were washed with brine, dried with sodium sulfate, and concentrated. The residue was purified by silica gel chromatography (EtOAc/petroleum ether) to give Preparation 8F (3.90 g, 70%). $^1$H NMR (400 MHz, chloroform-d) δ 7.41-7.22 (m, 7H), 6.50-6.40 (m, 4H), 5.53 (d, J=19.2 Hz, 1H), 5.40 (s, 1H), 4.49 (d, J=19.6 Hz, 1H), 3.65 (s, 3H).

Preparation 8G: 7-Amino-4-chloro-5-(4-methoxybenzyl)-5H-dibenzo[b,d]azepin-6(7H)-one

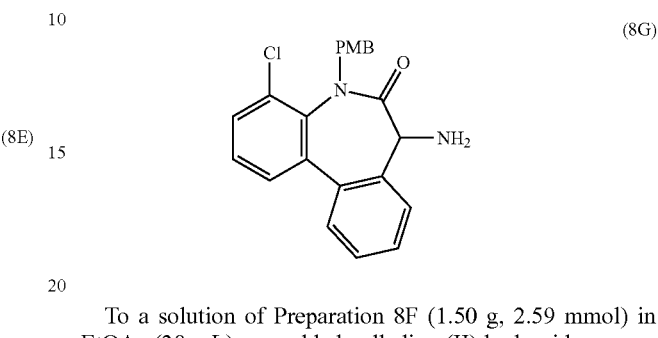

To a solution of Preparation 8F (1.50 g, 2.59 mmol) in EtOAc (30 mL) was added palladium(II) hydroxide on carbon (20% loading, contains 50% water, 150 mg). The atmosphere was exchanged for H$_2$ and the reaction mixture was stirred for 4 hours. The reaction mixture was filtered, washing with EtOAc, then the filtrate was concentrated. The residue was purified by silica gel chromatography (EtOAc/petroleum ether) to give Preparation 8G (800 mg, 81%). $^1$H NMR (400 MHz, chloroform-d) δ 7.37-7.36 (m, 1H), 7.36-7.27 (m, 4H), 7.22 (d, J=8 Hz, 1H), 6.50-6.38 (m, 4H), 5.56 (d, J=14.4 Hz, 1H), 4.88 (s, 1H), 4.48 (d, J=14.8 Hz, 1H), 3.65 (s, 3H).

Preparation 8H: 7-Amino-4-chloro-5H-dibenzo[b,d]azepin-6(7H)-one

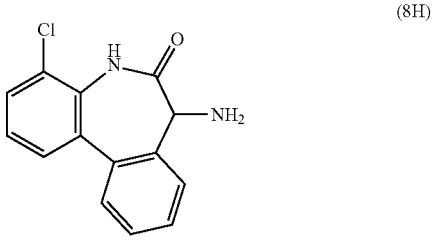 [SMILES: NC1C(=O)Nc2c(Cl)cccc2-c2ccccc21]

(8H)

To a solution of Preparation 8G (900 mg, 2.38 mmol) in TFA (20 mL) was added methanesulfonic acid (0.154 mL, 2.38 mmol). The reaction mixture was heated to 70° C. for 12 hours, then cooled to room temperature and evaporated. The resulting semisolid was added to saturated aqueous sodium bicarbonate and the aqueous layer was extracted twice with EtOAc. The combined organic layers were washed successively with water and brine, then dried with sodium sulfate and concentrated. The residue was purified by silica gel chromatography (EtOAc/petroleum ether) to give Preparation 8H (550 mg, 98%). $^1$H NMR (400 MHz, DMSO-d$_6$) δ 9.74 (s, 1H), 7.70 (d, J=10.4 Hz, 1H), 7.64-7.51 (m, 4H), 7.43 (t, J=8 Hz, 1H), 7.35 (t, J=10.6 Hz, 1H), 4.10 (s, 1H), 2.28 (br s, 2H).

Example 8

Example 8 was prepared from Preparation 8H and Preparation 1E by the same general procedure give for Example 1. HPLC: RT=8.81 min (H$_2$O/CH$_3$CN with TFA, SunFire C18 3.5 μm, 3.0×150 mm, gradient=15 min, wavelength=220 and 254 nm); MS(ES):m/z=550 [M+H$^+$]; $^1$H NMR (400 MHz, methanol-d₄) δ 7.74-7.58 (m, 3H), 7.49 (m, 3H), 7.43-7.32 (m, 1H), 5.41 (s, 1H), 2.91 (dd, J=16.0, 8.9 Hz, 1H), 2.53 (s, 1H), 2.28-2.01 (m, 4H), 1.84-1.61 (m, 4H).

Example 9

(2R,3S)-N-(4-Fluoro-6-oxo-6,7-dihydro-5H-dibenzo[b,d]azepin-7-yl)-3-propyl-2-(3,3,3-trifluoropropyl)succinamide

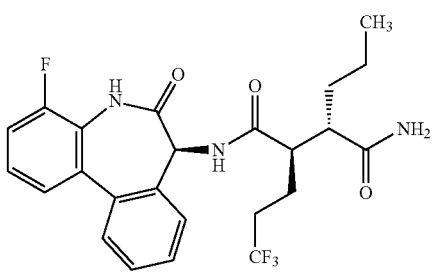

(9)

Example 9 was prepared from Preparation 2A (50.3 mg, 0.105 mmol) and Preparation 5G using the general procedure given for Example 1. Example 9: HPLC: RT=0.88 min (Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.11 mL/min); MS(ES):m/z=480.3 [M+H⁺]; ¹H NMR (400 MHz, DMSO-d₆) δ 10.24 (br. s., 1H), 9.15 (d, J=7.9 Hz, 1H), 7.67 (d, J=6.6 Hz, 1H), 7.63-7.47 (m, 5H), 7.46-7.35 (m, 2H), 6.92 (br. s., 1H), 5.29 (d, J=7.9 Hz, 1H), 2.89 (br. s., 1H), 2.35 (d, J=12.5 Hz, 2H), 2.23 (br. s., 1H), 1.60 (d, J=8.6 Hz, 2H), 1.51 (d, J=10.1 Hz, 1H), 1.24 (br. s., 1H), 1.09 (br. s., 2H), 0.79-0.71 (m, 3H).

Example 10

(2R,3S)-N-((7S)-9-Fluoro-4-methyl-6-oxo-6,7-dihydro-5H-dibenzo[b,d]azepin-7-yl)-2,3-bis(3,3,3-trifluoropropyl)succinamide

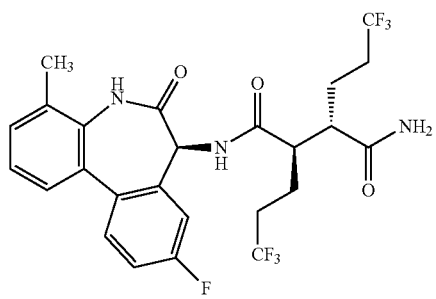

(10)

Preparation 10A: 4'-Fluoro-3-methyl-[1,1'-biphenyl]-2-amine

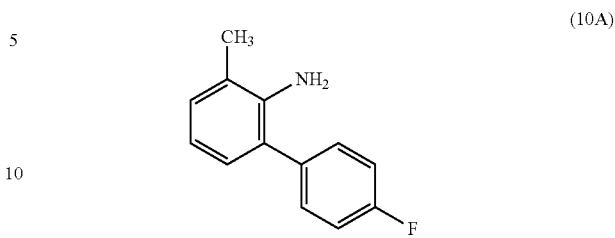

(10A)

A flask containing a mixture of 2-bromo-6-methylaniline (2 g, 10.75 mmol), (4-fluorophenyl)boronic acid (1.504 g, 10.75 mmol), and cesium carbonate (5.25 g, 16.12 mmol) in dioxane (28 mL) and water (7.00 mL) was degassed with nitrogen for 5 min, then PdCl₂(dppf)-CH₂Cl₂ adduct (0.439 g, 0.537 mmol) was added. The flask was quickly capped. The solution was heated at 85° C. for 16 h, then allowed to cool to room temperature. The reaction mixture was filtered through a pad of CELITE® and rinsed with EtOAc. After separating the layers, the aqueous layer was extracted with EtOAc three times. The combined organic extracts were washed with water, brine, dried over Na₂SO₄, filtered, and concentrated. The crude material was purified by ISCO (80 g REDISEP® silica column, gradient elution, 0-30% ethyl acetate in hexanes) to give Preparation 10A (2 g, 92% yield). LCMS: HPLC: RT=0.94 min (MeCN/H₂O with HCOONH₄, Ascentis Express C8 2.7 μm 5×2.1 mm, gradient=4 min, wavelength=220 nm); MS(ES): m/z=202 [M+H]⁺; ¹H NMR (400 MHz, chloroform-d) δ 7.55-7.43 (m, 2H), 7.25-7.12 (m, 3H), 7.04 (dd, J=7.5, 1.1 Hz, 1H), 6.92-6.76 (m, 1H), 3.72 (br. s., 2H), 2.29 (s, 3H).

Preparation 10B: 2-Bromo-N-(4'-fluoro-3-methyl-[1,1'-biphenyl]-2-yl)acetamide

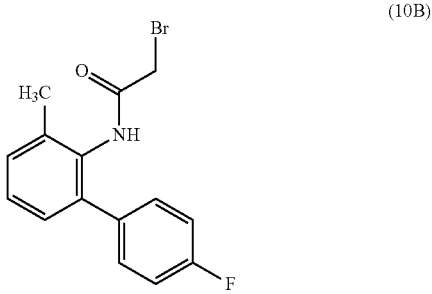 [SMILES: Cc1cccc(-c2ccc(F)cc2)c1NC(=O)CBr]

(10B)

A solution of Preparation 10A (1 g, 4.97 mmol) in DCM (5 mL) was cooled in an ice-water bath, then triethylamine (1.039 mL, 7.45 mmol) was added followed by 2-bromoacetyl bromide (0.647 mL, 7.45 mmol). After stirring in the cold bath for 30 min, the reaction mixture was then diluted with DCM and water. After separating the layers, the aqueous layer was extracted with DCM. The combined organic extracts were washed with sequentially with water and brine, then dried over MgSO₄, filtered and concentrated. The crude material was purified by ISCO (40 g REDISEP® column, gradient elution, 0-50% ethyl acetate in heptane) to give Preparation 10B (1.3 g, 81% yield). LCMS: HPLC: RT=0.94 min (MeCN/H₂O with HCOONH₄, Ascentis Express C8 2.7 μm (5×2.1) mm, gradient=4 min, wavelength=220 nm); MS(ES): m/z=324 [M+2H]⁺; ¹H NMR (400 MHz, chloroform-d) δ 7.62 (br. s., 1H), 7.39-7.24 (m, 3H), 7.24-7.05 (m, 3H), 3.87 (s, 2H), 2.33 (s, 3H).

Preparation 10C:
9-Fluoro-4-methyl-5H-dibenzo[b,d]azepin-6(7H)-one

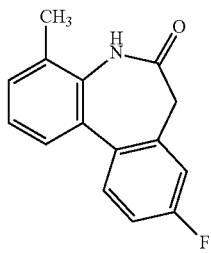

(10C)

To a solution of Preparation 10B (0.25 g, 0.776 mmol) in 1,2-dichlorobenzene (5 mL) was added aluminum chloride (0.517 g, 3.88 mmol). The reaction mixture was then heated in a microwave reactor at 200° C. for 10 min. The reaction was quenched with water, and the aqueous phase was extracted with DCM. The combined organic extracts were washed sequentially with water and brine, then dried over Na$_2$SO$_4$ and concentrated. Purification by ISCO (80 g REDISEP® column, gradient elution, 0-50% ethyl acetate in heptane) afforded Preparation 10C (75 mg, 40% yield). LCMS: HPLC: RT=0.90 min (MeCN/H$_2$O with HCOONH$_4$, Ascentis Express C8 2.7 μm (5×2.1) mm, gradient=4 min, wavelength=220 nm); MS(ES): m/z=242 [M+H]$^+$; $^1$H NMR (400 MHz, chloroform-d) δ 7.78 (br. s., 1H), 7.45 (d, J=7.7 Hz, 1H), 7.36-7.27 (m, 2H), 7.27-7.19 (m, 1H), 7.10 (td, J=8.4, 2.6 Hz, 1H), 3.60-3.50 (m, 1H), 3.43-3.33 (m, 1H), 2.40 (s, 3H).

Preparation 10D: 9-Fluoro-7-iodo-4-methyl-5H-dibenzo[b,d]azepin-6(7H)-one

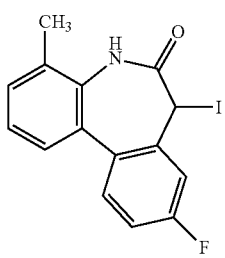

(10D)

To a solution of Preparation 10C (200 mg, 0.829 mmol) and triethylamine (0.462 mL, 3.32 mmol) in DCM (8 mL) at −20° C. was added iodotrimethylsilane (0.226 mL, 1.658 mmol). The reaction mixture turned into a clear yellow solution. After stirring for 15 min, iodine (316 mg, 1.243 mmol) was added. The reaction mixture was allowed to warm to −10° C. over 0.5 h. The reaction was quenched with saturated aqueous NaS$_2$O$_3$ and diluted with DCM. After separating the layers, the aqueous layer was further extracted with DCM two times. The combined organic extracts were washed sequentially with water and brine, then dried over MgSO$_4$, filtered and concentrated. The residue was purified by ISCO (12 g REDISEP® column, gradient elution, 0-60% ethyl acetate in hexanes) to afford Preparation 10D (160 mg, 52.6% yield). LCMS: HPLC: RT=0.99 min (MeCN/H$_2$O with HCOONH$_4$, Ascentis Express C8 2.7 μm (5×2.1) mm, gradient=4 min, wavelength=220 nm); MS(ES): m/z=368 [M+H]$^+$; $^1$H NMR (400 MHz, chloroform-d) δ 7.46 (d, J=7.9 Hz, 1H), 7.43-7.37 (m, 2H), 7.35-7.26 (m, 2H), 7.10 (td, J=8.3, 2.6 Hz, 1H), 5.79 (d, J=2.0 Hz, 1H), 2.44 (s, 3H).

Preparation 14E: 7-Amino-9-fluoro-4-methyl-5H-dibenzo[b,d]azepin-6(7H)-one

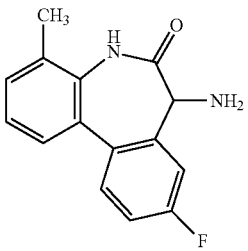

(10E)

To a solution of Preparation 10D (880 mg, 2.397 mmol) in toluene (20 mL) was added tetrabutylammonium azide (2046 mg, 7.19 mmol). After stirring at 60° C. for 1 h, the reaction mixture was cooled to room temperature. Then the reaction was quenched with water, and the aqueous phase was extracted with EtOAc. The combined organic extracts were washed sequentially with water and brine, then dried over Na$_2$SO$_4$ and concentrated. The residue was purified by ISCO (12 g REDISEP® column, gradient elution, 0-80% ethyl acetate in hexanes) to give 220 mg of impure azide product. To a solution of the above obtained azide (220 mg, 0.779 mmol) in THF (3 mL) was added water (1.500 mL) and triphenylphosphine (409 mg, 1.559 mmol). After stirring at 60° C. for 0.5 h, the reaction mixture was diluted with EtOAc and water. After separating the layers, the aqueous layer was further extracted with EtOAc. The combined organic extracts were washed sequentially with water and brine, then dried over MgSO$_4$, filtered and concentrated. The residue was purified by ISCO (12 g REDISEP® column, gradient elution, 0-60% EtOAc in hexane then 10% MeOH in DCM) to give Preparation 10E (50 mg, 55% yield over two steps). LCMS: RT=0.64 min (H$_2$O/MeCN with NH$_4$OAc, Xbridge BEH C18 2.5 μm (2.1×50) mm, gradient=2.5 min, wavelength=220 nm); MS(ES):m/z=257 [M+H$^+$], $^1$H NMR (400 MHz, chloroform-d) δ 7.69 (dd, J=8.4, 5.7 Hz, 1H), 7.62 (br. s., 1H), 7.46 (dd, J=7.7, 1.1 Hz, 1H), 7.38-7.31 (m, 1H), 7.30-7.16 (m, 2H), 5.32 (s, 1H), 4.35 (br. s., 2H), 2.41 (s, 3H).

Example 10

Example 10 was prepared from Preparation 1E and Preparation 10E using the general procedure described in Example 1. Example 10: LCMS: HPLC: RT=0.94 min (MeCN/H$_2$O with HCOONH$_4$, Ascentis Express C8 2.7 μm 5×2.1 mm, gradient=4 min, wavelength=220 nm); MS(ES): m/z=548 [M+H]$^+$; $^1$H NMR (400 MHz, DMSO-d$_6$) δ 9.71 (s, 1H), 9.23 (d, J=8.6 Hz, 1H), 7.64 (br. s., 1H), 7.57 (d, J=7.9 Hz, 1H), 7.54-7.45 (m, 2H), 7.41 (d, J=7.5 Hz, 1H), 7.35-7.20 (m, 2H), 7.12 (br. s., 1H), 5.21 (d, J=8.1 Hz, 1H), 3.03-2.83 (m, 1H), 2.44 (m, 1H), 2.40 (s, 3H), 2.36-2.00 (m, 4H), 1.81-1.54 (m, 3H), 1.43 (br. s., 1H).

Example 11

(2R,3S)-3-(Cyclopropylmethyl)-N-((7S)-9-fluoro-4-methyl-6-oxo-6,7-dihydro-5H-dibenzo[b,d]azepin-7-yl)-2-(3,3,3-trifluoropropyl)succinamide (11)

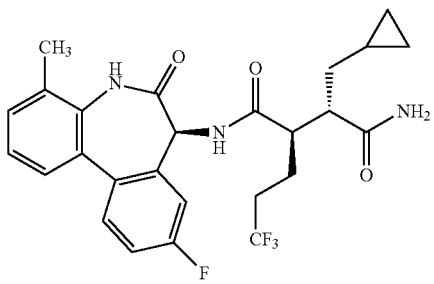

Example 11 was prepared from Preparation 10E and Preparation 3E using the general procedure disclosed for Example 1. Example 11: LCMS: HPLC: RT=0.93 min (MeCN/H$_2$O with HCOONH$_4$, Ascentis Express C8 2.7 μm 5×2.1 mm, gradient=4 min, wavelength=220 nm); MS(ES): m/z=506[M+H]$^+$; $^1$H NMR (400 MHz, DMSO-d$_6$) δ 9.71 (s, 1H), 9.09 (d, J=8.1 Hz, 1H), 7.70-7.22 (m, 7H), 6.97 (br. s., 1H), 5.19 (d, J=8.1 Hz, 1H), 2.89-2.75 (m, 1H), 2.44-2.33 (m, 3H), 1.74-1.50 (m, 3H), 1.36-1.06 (m, 3H), 0.97-0.69 (m, 3H), 0.61-0.43 (m, 1H), 0.41-0.22 (m, 2H).

Comparative Compounds 12 to 15

Comparative Compounds 12 to 15 can be prepared according to the procedures described in U.S. Pat. No. 7,053,084 for Examples 8, 12a, 38, and 45a, respectively.

TABLE 1

| Comparative Compound | U.S. Pat. No. 7,053,084 | Structure |
|---|---|---|
| 12 | Ex. 8 | 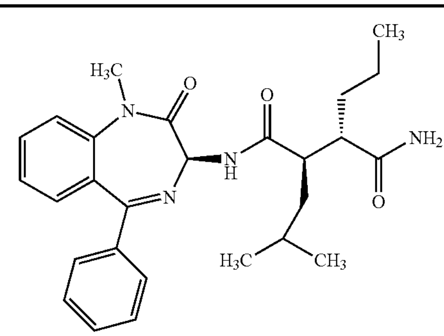 |
| 13 | Ex. 12a | 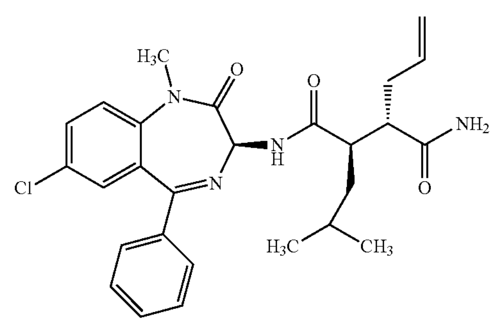 [SMILES: C=CC[C@H](C(N)=O)[C@@H](CC(C)C)C(=O)N[C@H]1N=C(c2ccccc2)c2cc(Cl)ccc2N(C)C1=O] |
| 14 | Ex. 38 | 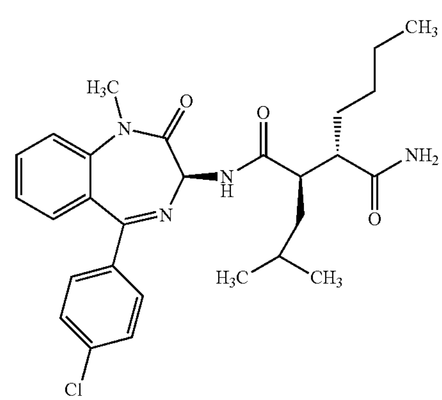 [SMILES: CCCC[C@H](C(N)=O)[C@@H](CC(C)C)C(=O)N[C@H]1N=C(c2ccc(Cl)cc2)c2ccccc2N(C)C1=O] |

TABLE 1-continued

| Comparative Compound | U.S. Pat. No. 7,053,084 | Structure |
|---|---|---|
| 15 | Ex. 45a | 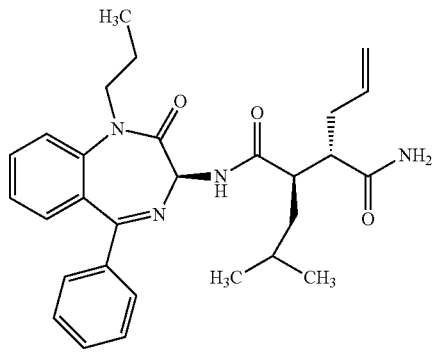 [SMILES: C=CC[C@H](C(N)=O)[C@@H](CC(C)C)C(=O)N[C@H]1N=C(c2ccccc2)c2ccccc2N(CCC)C1=O] |

BIOLOGICAL ASSAYS

The pharmacological properties of the compounds of this invention may be confirmed by a number of biological assays. The exemplified biological assays, which follow, have been carried out with compounds of the invention.

Notch-CBF1 Transactivation Assay

The Notch-CBF1 (C-promoter binding factor I) cell based transactivation assay is based on the ability of the released Notch intracellular domain fragments (NICDs) to function as transcription factors in conjunction with CBF1 and other nuclear factors. Luciferase assays were used to measure the antagonism of Notch-CBF1 transcriptional activity. HeLa cervical cancer cells are transiently co-transfected with pCDNA3.1/Hygro plasmids containing truncated Notch 1, Notch 2, Notch 3, or Notch 4 receptors and a PGL3 luciferase reporter vector containing 4 copies of CBF1 binding site. The cells were then tested for Notch-CBF1 activity in the absence or presence of test compounds. HeLa cells, maintained in DMEM (high glucose with HEPES), 1× glutamine/penicillin/streptomycin and 10% Fetal Bovine serum, were transiently transfected in a T175 Flask ($4.5 \times 10^6$ cells/flask) using the Monster Transfection Kit (Minis #MIR2906) according to manufacturers specifications. Table 2 denotes respective DNA quantity for the transfections.

TABLE 2

|  | DNA (µg) | CBF1 (µg) | Vector (µg) | Total DNA (µg) |
|---|---|---|---|---|
| human Notch 1 | 6 | 14.4 | 15.6 | 36.0 |
| human Notch 2 | 2 | 14.4 | 19.6 | 36.0 |
| human Notch 3 | 0.3 | 14.4 | 21.3 | 36.0 |
| human Notch 4 | 4 | 14.4 | 17.6 | 36.0 |

Six hours post-transfection, cells were trypsinized and plated into a 384-well black Poly-D-lysine coated tissue culture plate at a density of $5 \times 10^3$ cells/well in 95 µL assay media (DMEM (high glucose with HEPES), 1× glutamine/penicillin/streptomycin, 0.0125% BSA, 1× non-essential amino acids). Assay media (5 µL) containing test compounds in final concentrations ranging from 5 µM to $8.4 \times 10^{-5}$ µM (3 fold serial dilutions) were added to the cells and the cell plates were then incubated for 18 hours at 37° C. and 5% $CO_2$. Control wells contained DMSO vehicle (total counts) or 0.5 µM of an in-house small molecule inhibitor (background counts). Duplicates were used for each sample. Luciferase activity was measured after a 20-minute incubation with 50 µl STEADY-GLO® luciferase reagents according to manufacturer's specifications (Promega, Cat. #E2550) and analyzed by Envision plate reader (PerkinElmer, Boston, Mass.).

The antagonist effect of compounds was expressed as 100× [1-(average sample-average background)/(average total-average background)] where sample is the luciferase activity in the presence of test compound, background is equal to the luciferase activity in the presence of the small molecule inhibitor control and the total is signal induced in DMSO wells. Data was plotted using a four parameter logistic fit equation and the $IC_{50}$ value was defined as the concentration of compound that inhibited 50% of the luciferase activity.

Table 3 below lists the Notch 1 and Notch 3 $IC_{50}$ values for Examples 1-11 of this invention and Comparative Compounds 12-15 measured in the Notch-CBF1 Transactivation Assay hereinabove. In some instances, the value is an average of multiple experiments where N is the number of experiments conducted. The compounds of the present invention, as exemplified by the Examples 1-11 showed Notch 1 values of 25.9 nM or less and Notch 3 $IC_{50}$ values of 43.3 nM or less.

TABLE 3

| Example | Notch 1 ($IC_{50}$, nM) | N | Notch 3 ($IC_{50}$, nM) | N |
|---|---|---|---|---|
| 1 | 5.0 | 1 | 7.0 | 1 |
| 2 | 9.7 | 2 | 9.5 | 2 |
| 3 | 12.4 | 2 | 10.6 | 2 |
| 4 | 25.7 | 2 | 14.7 | 2 |
| 5 | 25.9 | 2 | 43.3 | 3 |
| 6 | 15.3 | 1 | 11.3 | 1 |
| 7 | 2.6 | 2 | 3.6 | 2 |
| 8 | 2.6 | 3 | 10.2 | 2 |
| 9 | 4.9 | 2 | 18.6 | 2 |
| 10 | 3.6 | 1 | 13.0 | 1 |
| 11 | 4.1 | 1 | 13.3 | 1 |
| Comparative Compound 12 | 64 |  | 48 |  |
| Comparative Compound 13 | 42 |  | 75 |  |
| Comparative Compound 14 | 5.1 |  | 13 |  |
| Comparative Compound 15 | 12 |  | 12 |  |

High Throughput (HT) Metabolic Stability Panel

Compounds administered parenterally enter the blood stream and undergo one or more passes through the liver. Compounds that are not readily metabolized by the liver can be administered at therapeutically effective plasma levels for therapeutically effective periods of time.

Orally administered compounds typically are absorbed through the intestinal walls into the blood stream and undergo a first pass through the liver. Compounds that are not readily metabolized in this first pass through the liver can be distributed to other areas of the body in therapeutically effective amounts.

The metabolic stability assay evaluated CYP-mediated metabolic stability in vitro using human, rat, mouse, dog, and/or monkey microsomes after a ten-minute incubation. Each compound was tested in duplicate.

The results of these assays were expressed as the fraction of parent compound remaining in the reaction mixture after a ten-minute incubation (Percent Remaining) In general, these results were used to evaluate only the extent of CYP-mediated, or NADPH-dependent, metabolism of the test compound. When the compound was significantly metabolized (<40-50% remaining), this indicated high clearance of the compound in vivo due to CYP-mediated metabolism. However, if the compound demonstrated moderate (50-80%) or low (>85%) metabolism in these in vitro assays, high clearance was still possible in vivo via other metabolism and elimination pathways.

The percent remaining results of these assays was predictive of compound clearance in vivo, assuming that CYP-mediated metabolism was a predominant elimination pathway. In different microsomal species, the ranges of results were approximately as shown in Table 4.

TABLE 4

Metabolic Stability - Result Interpretation Guidelines

| CYP-Mediated Clearance | Percent Remaining after 10 minutes | | | | |
|---|---|---|---|---|---|
| | Human | Rat | Mouse | Dog | Monkey |
| Low | >90 | >85 | >85 | >90 | >85 |
| Medium | 60-90 | 40-85 | 50-85 | 55-90 | 40-85 |
| High | <60 | <40 | <50 | <55 | <40 |

Methods and Materials
Incubation with Liver Microsomes

Test compound was received as a 3.5 mM stock solution in 100 percent DMSO. The test compound was diluted to create a 50 µM acetonitrile (ACN) solution containing 1.4% DMSO, which was then used as a 100× stock for incubation with microsomes. Each compound was tested in duplicate separately in each of three species in the Metabolic Stability-Human, Rat, and Mouse assay suite or as individual species in the Metabolic Stability-Dog or Metabolic Stability-Monkey suites. Compound, NADPH, and liver microsome solutions were combined for incubation in three steps:

1. 152 µl of liver microsome suspension, protein concentration of 1.1 mg/ml in 100 mM $NaP_i$, pH 7.4, 5 mM $MgCl_2$ buffer, was pre-warmed at 37° C.

2. 1.7 µl of 50 µM compound (98.6% ACN, 1.4% DMSO) was added to the same tube and pre-incubated at 37° C. for 5 minutes.

3. The reaction was initiated by the addition of 17 µl of pre-warmed 10 mM NADPH solution in 100 mM $NaP_i$, pH 7.4.

The reaction components were mixed well, and 75 µl of the reaction mixture was immediately transferred into 150 µl quench/stop solution (zero-time point, $T_0$). Reactions were incubated at 37° C. for 10 minutes and then an additional 75 µl aliquot was transferred into 150 µl quench solution. Acetonitrile containing 100 µM DMN (a UV standard for injection quality control), was used as the quench solution to terminate metabolic reactions.

Quenched mixtures were centrifuged at 1500 rpm (~500× g) in an ALLEGRA® X-12 centrifuge, SX4750 rotor (Beckman Coulter Inc., Fullerton, Calif.) for fifteen minutes to pellet denatured microsomes. A volume of 90 µl of supernatant extract, containing the mixture of parent compound and its metabolites, was then transferred to a separate 96-well plate for UV-LC/MS-MS analysis to determine the percent of parent compound that remained in the mixture.

TABLE 5

Metabolic Stability Assay - Reaction Components

| Reaction Components | Final Concentration in the Metabolic Stability Assay |
|---|---|
| Compound (Substrate) | 0.5 µM |
| NaPi Buffer, pH 7.4 | 100 mM |
| DMSO | 0.014% |
| Acetonitrile | 0.986% |
| Microsomes (human, rat, mouse) (BD/Gentest) | 1 mg/ml protein |
| NADPH | 1.0 mM |
| $MgCl_2$ | 5.0 mM |
| 37° C. Incubation time | 0 minutes and 10 minutes |
| Quench/Stop Solution (ACN+100 µM DMN) | 150 µl |
| Sample of Reaction | 75 µl |
| Sedimentation of Denatured Microsomes | 15 minutes |
| UV-LC/MS analysis of supernatant | 0.17 µM |

Sample Analysis—Instrumentation

HPLC: Pump—Thermo Surveyor; Autosampler—CTC/LEAP HTS; UV detector—Thermo Surveyor PDA plus; Column—VARIAN® C18, 3 µm, 2×20 mm with a 0.5 µm in-line filter; Mobile Phase for structural integrity pre-analysis: (A) 98% water, 2% acetonitrile with 10 mM ammonium acetate; (B) 10% water, 90% acetonitrile with 10 mM ammonium acetate; Mobile Phase for reaction sample analysis: (A) 98% water, 2% acetonitrile with 0.1% formic acid; (B) 2% water, 98% acetonitrile with 0.1% formic acid; (C) 0.1% ammonium hydroxide in water; (D) 0.1% ammonium hydroxide in acetonitrile.

Mass Spectrometer: Thermo TSQ QUANTUM® Ultra triple-quadrupole mass spectrometer.

Sample Analysis—Structural Integrity Pre-Analysis

The Metabolic Stability structural integrity pre-analysis was used to assess the purity of compounds being assayed. Compounds were received in 96-well plates as 57 µl of a 3.5 mM DMSO solution. The 3.5 mM compound DMSO stock solutions were diluted 18-fold with a solution containing equal volumes of acetonitrile, isopropanol, and MilliQ-$H_2O$. The resulting solutions (200 µM) were analyzed for structural integrity by LC-UV/MS on a Thermo LCQ Deca XP Plus ion trap mass spectrometer, using a Waters XBridge C18, 5 µm, 2×50 mm column with a Waters Sentry 2.1 mm guard column, and the LC conditions described in the table below, with a 5 µl injection and a flow rate of 1 ml/min. The acquired data reflected purity by UV absorbance at 220 nm. Only results for those compounds with purity greater than 50% were reported.

TABLE 6

Metabolic Stability - Structural Integrity Gradient

| Gradient Time (min) | A% | B% |
|---|---|---|
| 0.00 | 100 | 0 |
| 4.00 | 0 | 100 |
| 5.00 | 0 | 100 |
| 5.10 | 100 | 0 |
| 6.00 | 100 | 0 |

Sample Analysis—Incubated Samples

MS/MS condition optimization was conducted on a Thermo TSQ QUANTUM® triple-quadrupole mass spectrometer equipped with a heated-electrospray (H-ESI) source by automated infusion to obtain the SRM transitions and their corresponding collision energy values. Compound solutions at a concentration of 20 µM in 1:1 methanol:water were infused at a flow rate of 90 µL/min, then combined with the mobile phase at a flow rate of 50 µL/min before being introduced into the source. All compounds were optimized first using mobile phase A and B (50% A and 50% B), and if necessary, using mobile phase C and D (also with a 50:50 composition). The optimized parameters, including polarity, SRM transition and collision energy, were stored in a MICROSOFT ACCESS® database.

The mass spectrometric conditions obtained from automated infusion were used to analyze incubation samples from the Metabolic Stability assay. The injection volume was 5 µl and the flow rate was 0.8 ml/min. The gradient used was shown in the table below. All samples were injected with the gradient using mobile phase A and B first. If necessary (for instance, for chromatographic reasons), samples were re-injected with the same gradient, but using mobile phase C and D. All LC-MS/MS analysis parameters were captured electronically in the raw data files.

TABLE 7

Metabolic Stability - Sample Analysis Gradient

| Gradient Time (min) | A% (or C%) | B% (or D%) |
|---|---|---|
| 0.00 | 95 | 5 |
| 0.20 | 95 | 5 |
| 0.30 | 0 | 100 |
| 1.05 | 0 | 100 |
| 1.10 | 95 | 5 |
| 1.50 | 95 | 5 |

Data Analysis

Peak integration was performed with the XCALIBUR® software. The percent remaining calculation was performed by comparing the LC-MS/MS peak areas from the $T_{10\ minute}$ samples to those from the $T_{0\ minute}$ samples for each compound.

Quality Control

A set of three compounds was tested along with the test compound in each assay plate. Data was accepted and uploaded only if the results for these control compounds fall into the expected ranges shown below.

TABLE 8

Metabolic Stability Assay - Control Compound Values by Microsome Species

| | Average Percent Remaining ± SD | | | | |
|---|---|---|---|---|---|
| Compound | Human | Rat | Mouse | Dog | Monkey |
| Nefazodone | 0.4 ± 0.4 | 0.7 ± 0.6 | 0.4 ± 0.3 | 0.4 ± 0.4 | 0.6 ± 0.5 |
| Verapamil | 13.3 ± 3.5 | 4.4 ± 2.1 | 13.0 ± 4.2 | 5.6 ± 1.8 | 0.5 ± 0.5 |
| Carbamezepine | 96 ± 6 | 84 ± 9 | 90 ± 10 | 81 ± 7 | 89 ± 13 |

SD = Standard Deviation

Metabolic Stability Half-Life Panel

The rate of metabolism and half-life determined in vitro in human or animal liver microsomes was used to determine intrinsic clearance ($CL_{int}$) and hepatic clearance (CLh,b) of a compound. These parameters were useful for predicting in vivo human clearance, which defines the level of drug exposure in vivo (Obach et al, 1997, 1999).

The metabolic stability half-life assay panel evaluates the time-course and the rate of CYP-mediated (NADPH-dependent) metabolism in vitro in human, rat, mouse, dog and monkey microsomes. The time course spans a 45-minute incubation, and includes 0, 5, 10, 15, 30, and 45 minute time-points, at each of which the amount of test compound remaining in the mixture was measured.

Result Interpretation Guideline

The results of the metabolic stability half-life assay are expressed as a half-life ($T_{1/2}$, min). In general, these results should be used to evaluate only the extent of CYP-mediated, or NADPH-dependent, metabolism of the test compound. When the compound was significantly metabolized ($T_{1/2}$<14 minutes), this indicated high clearance in vivo due to CYP-mediated metabolism. However, if the compound demonstrated moderate (14-70 minutes) or low (>70 minutes) metabolism in these in vitro assays, high clearance was still possible in vivo via other metabolism and elimination pathways.

The results of these assays were predictive of compound clearance in vivo, assuming that CYP-mediated metabolism was a predominant elimination pathway. In human microsomes, the ranges of results were approximately as shown in the following table:

TABLE 9

Metabolic Stability Half-Life-Result Interpretation Guidelines

| CYP-Mediated Clearance | $T_{1/2}$, minutes Human |
|---|---|
| Low | >70 |
| Medium | 14-70 |
| High | <14 |

Methods and Materials

Liver microsomes were purchased from BD Biosciences (Woburn, Mass.) and NADPH from AppliChem Inc; all other reagents were obtained from Sigma.

Incubation with Liver Microsomes

Test compound was received as a 3.5 mM stock solution in 100 percent DMSO. The test compound was diluted to create a 50 µM acetonitrile (ACN) solution containing 1.4% DMSO, which was then used as a 100-fold stock for incubation with microsomes. Each compound was tested in human, rat, mouse, dog and monkey liver microsomes. Compound, NADPH and liver microsome solutions were combined for incubation in three steps:

1. 450 µl of liver microsome suspension, protein concentration of 1.1 mg/ml in 100 mM $NaP_i$, pH 7.4, 5 mM $MgCl_2$ buffer, was pre-warmed at 37° C.

2. 5 µl of 50 µM compound (98.6% ACN, 1.4% DMSO) was added to the same tube and pre-incubated at 37° C. for 5 minutes.

3. The reaction was initiated by the addition of 50 µl of pre-warmed 10 mM NADPH solution in 100 mM $NaP_i$, pH 7.4.

Reaction components were mixed well, and 65 µl were immediately transferred into 130 µl quench/stop solution (zero-time point, $T_0$). Reactions were incubated at 37° C. for 5, 10, 15, 30 and 45 minutes and at each time-point a 65 µl aliquot was transferred into 130 µl of quench solution. Acetonitrile containing Internal Standard (100 ng/ml), was used as the quench solution to terminate metabolic reactions.

Quenched mixtures were centrifuged at 1500 rpm (~500× g) in an ALLEGRA® X-12 centrifuge, SX4750 rotor (Beckman Coulter Inc., Fullerton, Calif.) for fifteen minutes to pellet denatured microsomes. A volume of 90 µl of supernatant extract, containing the mixture of parent compound and its metabolites, was then transferred to a separate 96-well plate for LC/MS-MS analysis to determine the per cent of parent compound that was remaining in the mixture.

TABLE 10

Metabolic Stability Half-Life Assays - Reaction Components

| Reaction Components | Final Concentration in the Metabolic Stability Assay |
|---|---|
| Compound (Substrate) | 0.5 µM |
| NaPi Buffer, pH 7.4 | 100 mM |
| DMSO | 0.014% |
| Acetonitrile | 0.986% |
| Microsomes (human, rat, mouse) (BD/Gentest) | 1 mg/ml protein |
| NADPH | 1.0 mM |
| MgCl$_2$ | 5.0 mM |
| 37° C. Incubation time | 0, 5, 10, 15, 30, and 45 minutes |
| Quench/Stop Solution (ACN+100 µM DMN) | 130 µl |
| Sample of Reaction | 65 µl |
| Sedimentation of Denatured Microsomes | 15 minutes |

Sample Analysis—Instrumentation

HPLC: Pump—Shimadzu LC-20 AD series binary pumps; Autosampler—CTC/LEAP HTS.

Table 11 below lists the CYP-mediated metabolic half life value for Examples 1-11 of this invention and Comparative Compounds 12-15 measured in the human metabolic stability half-life assay. In some instances, the value is an average of multiple experiments where N is the number of experiments conducted. The compounds of the present invention, as exemplified by Examples 1-11 had metabolic stability half life values of 40 minutes or longer. In contrast, Comparative Compounds 12-15 had metabolic stability half life values of 8 minutes or less.

TABLE 11

| Example | HLM (t$_{1/2}$, min.) | N |
|---|---|---|
| 1 | >120 | 2 |
| 2 | 50 | 3 |
| 3 | 59 | 4 |
| 4 | 59 | 3 |
| 5 | 59 | 1 |
| 6 | 49 | 1 |
| 7 | 76 | 1 |
| 8 | 77 | 1 |
| 9 | 46 | 1 |
| Comparative Compound 12 | 8 | 1 |
| Comparative Compound 13 | 6 | 1 |
| Comparative Compound 14 | 6 | 1 |
| Comparative Compound 15 | 3 | 1 |

The exemplified compounds of the invention showed the surprising advantage of low clearance due to CYP-mediated metabolism in the human metabolic stability half life assay. The compounds of the present invention, as exemplified by Examples 1-9, had metabolic half life values of 46 minutes or longer in the human metabolic stability half life assay. In contrast, Comparative Compounds 12-15 had metabolic half life values of 8 minutes or less in the human metabolic stability assay. Comparative Compounds 12-15 showed high clearance in the human metabolic stability assay, indicating that the compounds were removed by liver microsomes.

The compounds of the present invention (Examples 1-9) have been compared to the Comparative Compounds 12-15 disclosed in U.S. Pat. No. 7,456,172, and have been found to be especially advantageous. The compounds of the present invention (Examples 1-9) had the surprising advantage of the combination of activity as inhibitors of Notch 1 and Notch 3 and superior metabolic stability to liver microsomes. As shown in Tables 3 and 11, in the reported tests, Examples 1-9 of this invention had Notch 1 IC$_{50}$ values of 25.9 nM or less and Notch 3 IC$_{50}$ values of 43.3 nM or less; and human metabolic stability half lives of 46 minutes or longer in the human metabolic stability half life assay. In contrast, in similar tests, Comparative Compounds 12-15 had Notch 1 IC$_{50}$ values of in the range of from 5.1 nM to 64.1 nM and Notch 3 IC$_{50}$ values in the range of 12.5 nM to 74.5 nM; and human metabolic stability half lives of 8 minutes or less.

What is claimed is:
1. A compound of Formula (I):

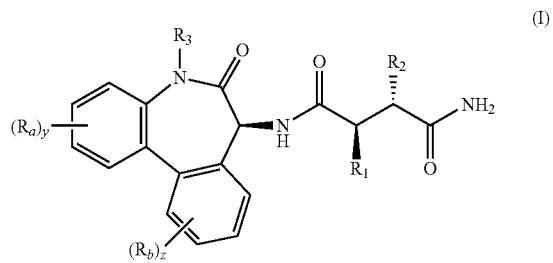

wherein:
R$_1$ is —CH$_2$CH$_2$CF$_3$ or —CH$_2$CH$_2$CH$_3$;
R$_2$ is —CH$_2$CH$_2$CF$_3$, —CH$_2$CH$_2$CH$_3$, —CH$_2$(cyclopropyl), phenyl, or

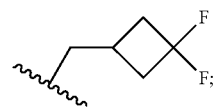 [SMILES: *CC1CC(F)(F)C1]

R$_3$ is H;
each R$_a$ is independently F, Cl, —CN, —OH, —CH$_3$, —CH$_2$OH, cyclopropyl, —CF$_3$, —CH$_2$CF$_3$, —OCH$_3$, —OCF$_3$, and/or —O(cyclopropyl);
each R$_b$ is independently F, Cl, —CH$_3$, —CF$_3$, —CN, and/or —OCH$_3$;
y is zero, 1, or 2; and
z is zero, 1, or 2;
with the proviso that R$_1$ and R$_2$ are not each —CH$_2$CH$_2$CH$_3$ simultaneously.
2. The compound according to claim 1 wherein R$_2$ is —CH$_2$CH$_2$CF$_3$.
3. The compound according to claim 1 wherein one of R$_1$ and R$_2$ is —CH$_2$CH$_2$CH$_3$.
4. The compound according to claim 1 wherein R$_2$ is —CH$_2$(cyclopropyl) or

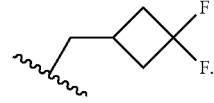 [SMILES: *CC1CC(F)(F)C1]

5. The compound according to claim 1 wherein $R_2$ is phenyl.

6. The compound according to claim 1 having the structure:

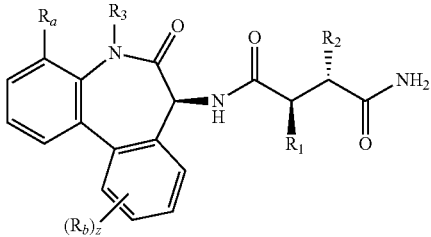

wherein:
$R_a$ is independently F, Cl, —CH$_3$, or —CH$_2$OH;
$R_b$ is F; and
z is zero or 1.

7. A compound according to claim 1 selected from: (2R,3S)-N-((7S)-6-oxo-6,7-dihydro-5h-dibenzo[b,d]azepin-7-yl)-2,3-bis(3,3,3-trifluoropropyl)succinamide (1); (2R,3S)-N-((7S)-6-oxo-6,7-dihydro-5H-dibenzo[b,d]azepin-7-yl)-3-propyl-2-(3,3,3-trifluoropropyl)succinamide (2); (2R,3S)-3-(cyclopropylmethyl)-N-((7S)-6-oxo-6,7-dihydro-5H-dibenzo[b,d]azepin-7-yl)-2-(3,3,3-trifluoropropyl) succinamide (3); (2R,3S)-N-((7S)-6-oxo-6,7-dihydro-5H-dibenzo[b,d]azepin-7-yl)-2-propyl-3-(3,3,3-trifluoropropyl) succinamide (4); (2R,3S)-3-(cyclopropylmethyl)-N-((7S)-4-fluoro-6-oxo-6,7-dihydro-5H-dibenzo[b,d]azepin-7-yl)-2-(3,3,3-trifluoropropyl)succinamide (5); (2R,3R)-N-((7S)-6-oxo-6,7-dihydro-5H-dibenzo[b,d]azepin-7-yl)-3-phenyl-2-(3,3,3-trifluoropropyl) succinamide (6); (2R,3S)-3-((3,3-difluorocyclobutyl)methyl)-N-((7S)-6-oxo-6,7-dihydro-5H-dibenzo[b,d]azepin-7-yl)-2-(3,3,3-trifluoropropyl) succinamide (7); (2R,3S)-N-(4-chloro-6-oxo-6,7-dihydro-5H-dibenzo[b,d]azepin-7-yl)-2,3-bis(3,3,3-trifluoropropyl) succinamide (8); (2R,3S)-N-(4-fluoro-6-oxo-6,7-dihydro-5H-dibenzo[b,d]azepin-7-yl)-3-propyl-2-(3,3,3-trifluoropropyl) succinamide (9); (2R,3S)-N-((7S)-9-fluoro-4-methyl-6-oxo-6,7-dihydro-5H-dibenzo[b,d]azepin-7-yl)-2,3-bis(3,3,3-trifluoropropyl)succinamide (10); and (2R,3S)-3-(cyclopropylmethyl)-N-((7S)-9-fluoro-4-methyl-6-oxo-6,7-dihydro-5H-dibenzo[b,d]azepin-7-yl)-2-(3,3,3-trifluoropropyl) succinamide (11).

8. A pharmaceutical composition comprising at least one compound according claim 1; and a pharmaceutically acceptable carrier.

* * * * *